US008628759B2

(12) United States Patent
Bodor

(10) Patent No.: US 8,628,759 B2
(45) Date of Patent: Jan. 14, 2014

(54) SOFT ANTICHOLINERGIC ESTERS

(75) Inventor: Nicholas S. Bodor, Bal Harbour, FL (US)

(73) Assignee: Bodor Laboratories, Inc., Miami, FL (US)

( * ) Notice: Subject to any disclaimer, the term of this patent is extended or adjusted under 35 U.S.C. 154(b) by 0 days.

(21) Appl. No.: 13/423,071

(22) Filed: Mar. 16, 2012

(65) Prior Publication Data
US 2012/0177590 A1 Jul. 12, 2012

Related U.S. Application Data

(60) Continuation of application No. 12/494,367, filed on Jun. 30, 2009, now Pat. No. 8,147,809, which is a division of application No. 12/138,013, filed on Jun. 12, 2008, now Pat. No. 7,576,210, which is a division of application No. 11/598,079, filed on Nov. 13, 2006, now Pat. No. 7,399,861.

(60) Provisional application No. 60/735,207, filed on Nov. 10, 2005.

(51) Int. Cl.
C07D 207/10 (2006.01)
C07D 451/10 (2006.01)
A61K 31/56 (2006.01)
A61K 31/4015 (2006.01)
A61K 8/40 (2006.01)
A61P 11/08 (2006.01)
A61P 11/06 (2006.01)
A61P 11/02 (2006.01)
A61P 13/10 (2006.01)
A61P 29/00 (2006.01)
A61P 27/08 (2006.01)
A61Q 15/00 (2006.01)

(52) U.S. Cl.
USPC .............................. 424/65; 514/171; 514/424

(58) Field of Classification Search
None
See application file for complete search history.

(56) References Cited

U.S. PATENT DOCUMENTS

2004/0101483 A1  5/2004  Muller-Walz et al.

FOREIGN PATENT DOCUMENTS

| CA | 2559699 A1 | 11/2005 |
| JP | 2004-525148 A | 8/2004 |
| WO | WO 02/078671 A1 | 10/2002 |
| WO | WO 2004/075896 A1 | 9/2004 |
| WO | 2005/000815 A2 | 1/2005 |
| WO | WO 2005/000317 A1 | 1/2005 |
| WO | WO 2005/074924 A1 | 8/2005 |
| WO | WO 2005/102349 A1 | 11/2005 |
| WO | 2006/066928 A1 | 6/2006 |

OTHER PUBLICATIONS

Ipratropium, 2013,http://en.wikipedia.org/wiki/Ipratropium_bromide.*
Darifenacin, 1997,http://www.ncbi.nlm.nih.gov/pubmed/9029489.*
Francois, 1967, Journal of the National Medical Association, vol. 59,p. 48-50.*
Ji et al., Journal of Pharmacy and Pharmacology, 2005, 57, 1427-1435.*
Ji-et-al-date, 2005, front cover of Journal of Pharmacy and Pharmacology, 1 page.*
Ji, F. et al: "Synthesis and pharmacological effects of new, N-substituted soft anticholinergics based on glycopyrrolate", Journal of Pharmacy and Pharmacology, vol. 57, No. 11, pp. 1427-1435, 2005, Pharmaceutical Press, England.
Wu, Whei-Mei et al.: "Pharmacokinetic and Pharmacodynamic Evaluations of the Zwitterionic Metabolite of a New Series of N-Substituted Soft Anticholinergics", Pharmaceutical Research, vol. 22, No. 12, pp. 2035-2044 Dec. 12, 2005 (available online Sep. 26, 2005), Springer.
Banholzer, Von R. et al.: "Synthesis of anticholinergically active N-alkylnorscopolamines and their quaternary salts with particular consideration of the bronchospasmolytic compound (−)-N-ethylnorscopolamine methobromide (Ba 253 BR)", Arzneimittel-Forschung, 35(1A), pp. 217-228, 1985.
Archer, et al. caplu an 1964:411286.
Chronic Obstructive Pulmonary Disease, htt://www.clevelandclinicmeded.com/medicalpubs/diseasemanagement/pulmonary/copd/copd.htm, 2005.

(Continued)

Primary Examiner — Sun Jae Loewe
(74) Attorney, Agent, or Firm — Dentons US LLP

(57) ABSTRACT

Soft anticholinergic esters of the formulas:

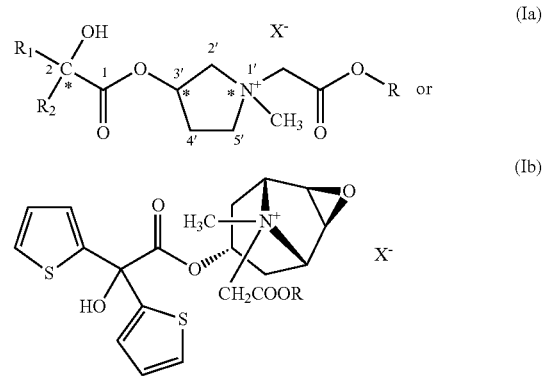

wherein $R_1$ and $R_2$ are both phenyl or one of $R_1$ and $R_2$ is phenyl and the other is cyclopentyl; R is $C_1$-$C_8$ alkyl, straight or branched chain; and $X^-$ is an anion with a single negative charge; and wherein each asterisk marks a chiral center; said compound having the R, S or RS stereoisomeric configuration at each chiral center unless specified otherwise, or being a mixture thereof.

18 Claims, 10 Drawing Sheets

(56) References Cited

OTHER PUBLICATIONS

Anticholinergics—Asthma Controller Medication, http://www.pamf.org/asthma/medications/inhaled/atrovent.html, 2005/2006.
Asthma, http://www.pamf.org/asthma/medications/inhaled/atrovent.html, 2005.
Bronchitis, http://www.chemocare.com/managing/bronchitis.asp, 2005.
Allergic Rhinitis, http://www.health.am/allergies/more/allergic_rhinitis, 2005/2007.
Allergies-NonAllergic Vasomotor Rhinitis, http://allergies.about.com/od/noseandsinusallergies/a/pnar.htm, 1998/2007.
Mydriasis, http://en.wikipedia.org/wiki/Mydriasis, 2008.
Herbison et al, BMJ vol. 326, 2003, 841-844.
Antiperspirant, http://www.medscape.com/viewarticle/427679_6, 2002.
International Search Report dated Jan. 6, 2007 for PCT/US2006/043858.
Written Opinion of the International Searching Authority dated Jan. 6, 2007 for PCT/US2006/043858.
Office Action dated Jun. 26, 2012 issued in corresponding application in Japan, with English language translation.

\* cited by examiner

| ATR | Atropine $10^{-8}$ (M) n = 6 |
| IPR | Ipratropium Br $10^{-8}$ (M) n = 6 |
| TIO | Tiotropium $7 \times 10^{-9}$ (M) n = 6 |
| Cpd (w) | Cpd (w) $3 \times 10^{-7}$ (M) n = 5 |
| Cpd (aa) | Cpd (aa) $3 \times 10^{-7}$ (M) n = 5 |
| Control | Vehicle treated preparations n = 10 |

| ATR | Atropine $10^{-8}$ (M) n = 6 |
| IPR | Ipratropium Br $10^{-8}$ (M) n = 6 |
| TIO | Tiotropium $7 \times 10^{-9}$ (M) n = 6 |
| Cpd (w) | Cpd (w) $3 \times 10^{-7}$ (M) n = 5 |
| Cpd (aa) | Cpd (aa) $3 \times 10^{-7}$ (M) n = 5 |
| Control | Vehicle treated preparations n = 10 |

SOFT ANTICHOLINERGIC ESTERS

CROSS-REFERENCE TO RELATED APPLICATIONS

This application is a continuation of U.S. patent application Ser. No. 12/494,367, filed Jun. 30, 2009, now U.S. Pat. No. 8,147,809, which is a divisional of U.S. patent application Ser. No. 12/138,013, filed Jun. 12, 2008, now U.S. Pat. No. 7,576,210, which is a divisional of U.S. patent application Ser. No. 11/598,079, filed Nov. 13, 2006, now U.S. Pat. No. 7,399,861, which claims benefit of U.S. Provisional Patent Application No. 60/735,207, filed Nov. 10, 2005, all incorporated by reference herein in their entireties and relied upon.

This application is also related to U.S. application Ser. No. 11/598,076 concurrently filed with prior application Ser. No. 11/598,079 on Nov. 13, 2006, by the present inventor and claiming benefit of U.S. Provisional Application No. 60/735,206, filed Nov. 10, 2006, now U.S. Pat. No. 7,417,174, as well as application Ser. No. 12/137,896, filed Jun. 12, 2008, as a divisional of application Ser. No. 11/598,076, now U.S. Pat. No. 7,538,219, and its divisional, application Ser. No. 12/418,939, filed Apr. 6, 2009, now U.S. Pat. No. 8,071,639, as well as the divisional thereof, application Ser. No. 13/286,020, filed Oct. 31, 2011, all incorporated by reference herein in their entireties and relied upon.

BACKGROUND

Various anticholinergic compounds have been previously described but are not optimal.

Muscarinic receptor antagonists are frequently used therapeutic agents that inhibit the effects of acetylcholine by blocking its binding to muscarinic cholinergic receptors at neuroeffector sites on smooth muscle, cardiac muscle, and gland cells as well as in peripherial ganglia and in the central nervous system (CNS). However, their side effects, which can include dry mouth, photophobia, blurred vision, urinary hesitancy and retention, decreased sweating, drowsiness, dizziness, restlessness, irritability, disorientation, hallucinations, tachycardia and cardiac arrhythmias, nausea, constipation, and severe allergic reactions, often limit their clinical use, and even topical anticholinergics can cause the same unwanted side effects. Glycopyrrolate and triotropium are among the quaternary ammonium anticholinergics, which have reduced CNS-related side effects as they cannot cross the blood-brain barrier, however, because glycopyrrolate (or, presumably, tiotropium) is eliminated mainly as unchanged drug or active metabolite in the urine, its administration is problematic in young or elderly patients and especially in uraemic patients. To increase the therapeutic index of anticholinergics, the soft drug approach has been applied in a number of different designs starting from various lead compounds over the past 20 years, but there is a need for yet other new soft anticholinergics. These novel muscarinic antagonists, just as all other soft drugs, are designed to elicit their intended pharmacological effect at the site of application, but to be quickly metabolized into their designed-in, inactive metabolite upon entering the systemic circulation and rapidly eliminated from the body, resulting in reduced systemic side effects and increased therapeutic index.

SUMMARY

New soft anticholinergic agents, pharmaceutical compositions containing them, processes for their preparation and methods for eliciting an anticholinergic response, especially for treating an obstructive disease of the respiratory tract or for treating overactive bladder, are provided.

In one exemplary embodiment, there is provided a compound having the formula

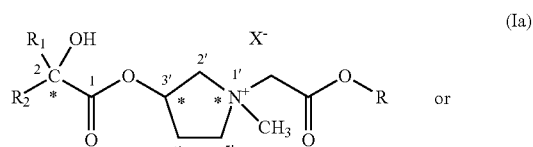

(Ia)

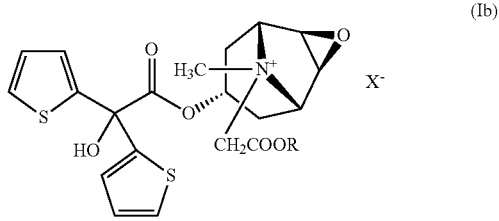

(Ib)

wherein $R_1$ and $R_2$ are both phenyl or one of $R_1$ and $R_2$ is phenyl and the other is cyclopentyl; R is $C_1$-$C_8$ alkyl, straight or branched chain; and $X^-$ is an anion with a single negative charge; and wherein each asterisk marks a chiral center; said compound having the R, S or RS stereoisomeric configuration at each chiral center unless otherwise specified, or being a mixture thereof.

In another exemplary embodiment, there is provided a compound having the formula

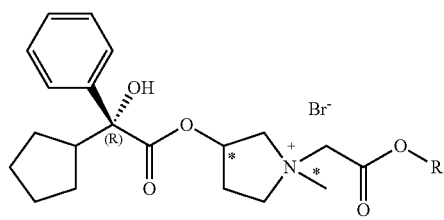

wherein R is methyl or ethyl.

In other exemplary embodiments, processes for preparing the compounds are provided.

In other exemplary embodiments, there arm provided pharmaceutical compositions comprising one or more of the compounds of the foregoing formulas and pharmaceutically acceptable carriers therefor; pharmaceutical combinations comprising one or more of the compounds of the foregoing formulas and an anti-inflammatory corticosteroid, a betamimetic agent or an antialleric agent; and methods of using the subject compositions and combinations.

DETAILED DESCRIPTION

Figure 1:
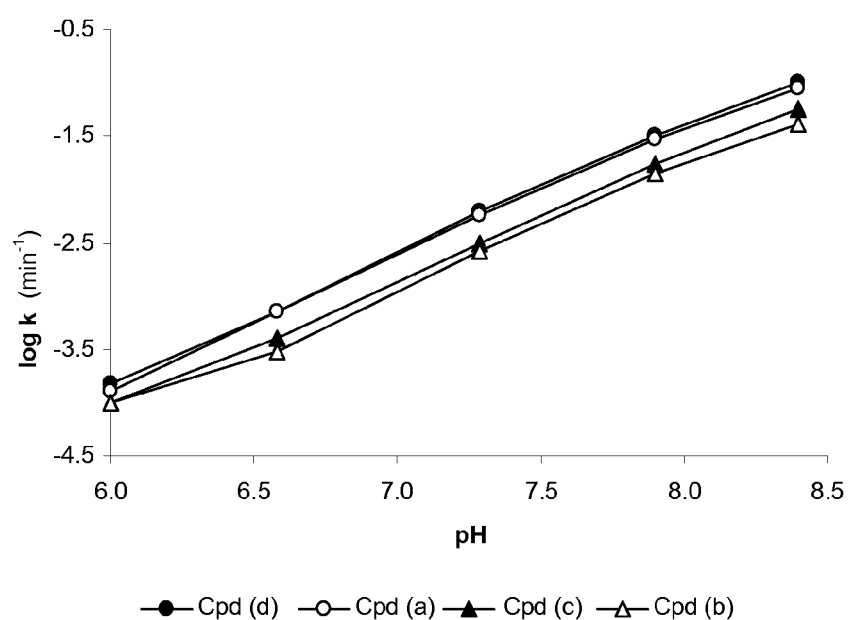
FIG. 1 depicts the pH profiles of four compounds of the invention: Compound (a), -○-; Compound (b), -Δ-; Compound (c), -▲-; and Compound (d), -•-.

Throughout this specification, the following definitions, general statements and illustrations are applicable:

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a composition, the term "comprising" means that the composition includes at least the recited features or components, but may also include additional features or components.

The terms "consists essentially of" or "consisting essentially of" have a partially closed meaning, that is, they do not permit inclusion of steps or features or components which would substantially change the essential characteristics of a process or composition; for example, steps or features or components which would significantly interfere with the desired properties of the compounds or compositions described herein, i.e., the process or composition is limited to the specified steps or materials and those which do not materially affect the basic and novel characteristics of the invention. The basic and novel features herein are the provision of compounds of formula (Ia) and (Ib) and combinations of those compounds with other drugs, particularly with anti-inflammatory steroids, especially loteprednol etabonate or etiprednol dichloracetate, and most especially in the case of loteprenol etabonate (LE) further including an inactive metabolite enhancing agent for the LE as further defined hereinafter.

The terms "consists of" and "consists" are closed terminology and allow only for the inclusion of the recited steps or features or components.

As used herein, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

As used herein, the recitation of a numerical range for a variable is intended to convey that the variable can be equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the specification and claims, the singular forms include plural referents unless the context clearly dictates otherwise. As used herein, unless specifically indicated otherwise, the word "or" is used in the "inclusive" sense of "and/or" and not the "exclusive" sense of "either/or."

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001).

As used herein, "treating" means reducing, preventing, hindering or inhibiting the development of, controlling, alleviating and/or reversing the symptoms in the individual to which a combination or composition comprising a compound of formula (Ia) or (Ib) has been administered, as compared to the symptoms of an individual not being so treated. A practitioner will appreciate that the combinations, compositions, dosage forms and methods described herein are to be used in concomitance with continuous clinical evaluations by a skilled practitioner (physician or veterinarian) to determine subsequent therapy. Such evaluation will aid and inform in evaluating whether to increase, reduce or continue a particular treatment dose, and/or to alter the mode of administration.

The methods described herein are intended for use with any subject/patient that may experience their benefits. Thus, the terms "subjects" as well as "patients," "individuals" and "warm-blooded animals" include humans as well as non-human subjects, particularly domesticated animals, particularly dogs, cats, horses and cows, as well as other farm animals, zoo animals and/or endangered species.

X⁻ denotes an anion with a single negative charge. This anion is an anion of a pharmaceutically acceptable acid. Preferably, X⁻ is chloride, bromide, iodide, sulfate, phosphate, methanesulfonate, nitrate, maleate, acetate, citrate, fumarate, tartrate, oxalate, succinate, benzoate or p-toluenesulfonate. More preferably, X⁻ is chloride, bromide, 4-toluenesulfonate or methanesulfonate. Most preferably X⁻ is bromide.

In formula (Ia), the compounds having the R configuration with respect to chiral center 2 are of particular interest.

The moiety R in formulas (Ia) and (Ib) can be methyl, ethyl, n-propyl, n-butyl, n-pentyl, n-hexyl, n-heptyl or n-octyl or their branched chain isomers.

In the compounds of formulas (Ia) and (Ib), R is preferably $C_1$-$C_6$ straight chain alkyl.

In the compounds of formula (Ia), compounds wherein one of $R_1$ and $R_2$ is phenyl and the other is cyclopentyl are of particular interest.

Also of particular interest are the compounds of the formula:

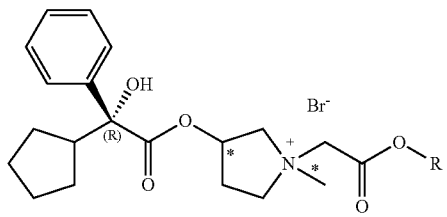

wherein R is methyl or ethyl.

The following specific compounds of formula (Ia) are of particular interest:
(a) 3-(2-cyclopentyl-2-phenyl-2-hydroxyacetoxy)-1-(methoxycarbonylmethyl)-1-methylpyrrolidinium bromide;
(b) 3-(2-cyclopentyl-2-phenyl-2-hydroxyacetoxy)-1-(ethoxycarbonylmethyl)-1-methylpyrrolidinium bromide;
(c) (2R) 3-(2-cyclopentyl-2-phenyl-2-hydroxyacetoxy)-1-(methoxycarbonylmethyl)-1-methylpyrrolidinium bromide;
(d) (2R) 3-(2-cyclopentyl-2-phenyl-2-hydroxyacetoxy)-1-(ethoxycarbonylmethyl)-1-methylpyrrolidinium bromide;
(e) (2R,3'R) 3-(2-cyclopentyl-2-phenyl-2-hydroxyacetoxy)-1-(methoxycarbonylmethyl)-1-methylpyrrolidinium bromide;
(f) (2R,3'S) 3-(2-cyclopentyl-2-phenyl-2-hydroxyacetoxy)-1-(methoxycarbonylmethyl)-1-methylpyrrolidinium bromide;
(g) (2R,3'S) 3-(2-cyclopentyl-2-phenyl-2-hydroxyacetoxy)-1-(ethoxycarbonylmethyl)-1-methylpyrrolidinium bromide;
(h) (2S,3'R) 3-(2-cyclopentyl-2-phenyl-2-hydroxyacetoxy)-1-(methoxycarbonylmethyl)-1-methylpyrrolidinium bromide;
(i) (2S,3'S) 3-(2-cyclopentyl-2-phenyl-2-hydroxyacetoxy)-1-(methoxycarbonylmethyl)-1-methylpyrrolidinium bromide;
(j) (2R,3'S) 3-(2-cyclopentyl-2-phenyl-2-hydroxyacetoxy)-1-(ethoxycarbonylmethyl)-1-methylpyrrolidinium bromide;
(k) (2R,1'R, 3'S) 3-(2-cyclopentyl-2-phenyl-2-hydroxyacetoxy)-1-(ethoxycarbonylmethyl)-1-methylpyrrolidinium bromide;
(l) (2R,1'S,3'S) 3-(2-cyclopentyl-2-phenyl-2-hydroxyacetoxy)-1-(ethoxycarbonylmethyl)-1-methylpyrrolidinium bromide;
(m) (2R,1'R,3'R) 3-(2-cyclopentyl-2-phenyl-2-hydroxyacetoxy)-1-(ethoxycarbonylmethyl)-1-methylpyrrolidinium bromide;
(n) (2R,1'S,3'R) 3-(2-cyclopentyl-2-phenyl-2-hydroxyacetoxy)-1-(ethoxycarbonylmethyl)-1-methylpyrrolidinium bromide;
(o) (2R,1'R,3'S) 3-(2-cyclopentyl-2-phenyl-2-hydroxyacetoxy)-1-(n-hexyloxycarbonylmethyl)-1-methylpyrrolidinium bromide;
(p) (2R,1'S,3'S) 3-(2-cyclopentyl-2-phenyl-2-hydroxyacetoxy)-1-(n-hexyloxycarbonylmethyl)-1-methylpyrrolidinium bromide;
(q) (2R,1'R, 3'R) 3-(2-cyclopentyl-2-phenyl-2-hydroxyacetoxy)-1-(n-hexyloxycarbonylmethyl)-1-methylpyrrolidinium bromide;
(r) (2R,1'S, 3'R) 3-(2-cyclopentyl-2-phenyl-2-hydroxyacetoxy)-1-(n-hexyloxycarbonylmethyl)-1-methylpyrrolidinium bromide;
(s) (2R,1'R, 3'S) 3-(2-cyclopentyl-2-phenyl-2-hydroxyacetoxy)-1-methyl-1-(n-octyloxycarbonylmethyl)pyrrolidinium bromide;
(t) (2R,1'S,3'S) 3-(2-cyclopentyl-2-phenyl-2-hydroxyacetoxy)-1-methyl-1-(n-octyloxycarbonylmethyl)pyrrolidinium bromide;
(u) (2R,1'R,3'R) 3-(2-cyclopentyl-2-phenyl-2-hydroxyacetoxy)-1-methyl-1-(n-octyloxycarbonylmethyl)pyrrolidinium bromide; or
(v) (2R,1'S,3'R) 3-(2-cyclopentyl-2-phenyl-2-hydroxyacetoxy)-1-methyl-1-(n-octyloxycarbonylmethyl)pyrrolidinium bromide.

Of these, particular mention may be made of:
(a) 3-(2-cyclopentyl-2-phenyl-2-hydroxyacetoxy)-1-(methoxycarbonylmethyl)-1-methylpyrrolidinium bromide;
(b) 3-(2-cyclopentyl-2-phenyl-2-hydroxyacetoxy)-1-(ethoxycarbonylmethyl)-1-methylpyrrolidinium bromide;
(c) (2R) 3-(2-cyclopentyl-2-phenyl-2-hydroxyacetoxy)-1-(methoxycarbonylmethyl)-1-methylpyrrolidinium bromide; or
(d) (2R) 3-(2-cyclopentyl-2-phenyl-2-hydroxyacetoxy)-1-(ethoxycarbonylmethyl)-1-methylpyrrolidinium bromide.

In formula (Ib), the compound wherein R is ethyl and X⁻ is Br⁻ is of special interest. The compounds of formula (Ib) wherein R is methyl, n-hexyl and n-octyl and X⁻ is Br⁻ can be made in analogous fashion to the R=ethyl compound and are also of particular interest.

Various methods of making the instant compounds are illustrated hereinafter. Generally speaking, the compounds of formula (Ia) can be prepared by reacting a bromoacetate of the formula

BrCH₂COOR wherein R is as defined above, with a compound of the formula

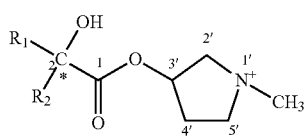

(IIa)

wherein $R_1$ and $R_2$, the asterisks and the stereoisomeric configurations are as defined above, and optionally separating the individual stereoisomers to afford a compound of formula (Ia) and, when desired, exchanging the bromine anion with a different X⁻ anion wherein X⁻ is as defined above but other than Br⁻.

In a particular embodiment, the compound of formula (IIa) has the R configuration with respect to chiral center 2.

In another particular embodiment, the compound of formula (IIa) has the configuration R or S with respect to chiral center 1' or with respect to chiral center 3'.

In another embodiment, the process includes separating the individual stereoisomers of the compound of formula (Ia) after their formation to the extent possible.

In one particular embodiment, the process comprises quaternmizing a compound of the formula

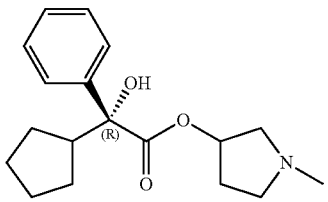

with an alkyl bromoacetate of the formula

wherein R is methyl or ethyl, to afford the desired product.

In analogous fashion, methods of making the compounds of formula (Ib) are illustrated hereinafter. Generally speaking, the process comprises reacting a bromocetate of the formula:

wherein R is as defined above, with a compound of the formula

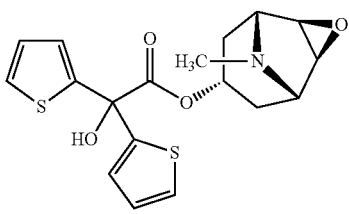

(IIb)

and optionally separating the individual stereoisomers to afford a compound of formula (Ib) and, when desired, exchanging the bromine anion with a different X⁻ anion wherein X⁻ is as defined above but other than Br⁻.

In the case of both the compounds of formula (Ia) and those of formula (Ib), use of ICH₂COOR or ClCH₂COOR in place of BRCH₂COOR can be employed in the above reaction schemes to afford the corresponding compounds in which X⁻ is I⁻ or Cl⁻. Alternatively, ion exchange columns can be used to replace the Br anion in the product of formula (Ia) or (Ib) with a different X⁻ anion.

The compounds of formulas (Ia) and (Ib) are of use as pharmaceutical agents because of their anticholinergic activity. An anticholinergically effective amount of such an agent inhibits the effect of acetycholine by blocking its binding to muscarinic cholinergic receptors at neuroeffector sites. Subjects in need of a method of eliciting an anticholinergic response are those suffering from conditions which respond to treatment with an anticholinergic agent. Such conditions include obstructive diseases of the respiratory tract, for example asthma and chronic obstructive pulmonary disease, vagally induced sinus bradycardia and heart rhythm disorders, spasms, for example in the gastrointestinal tract or urinary tract (including overactive bladder) and in menstrual disorders. The compounds of formulas (Ia) and (Ib) can also be used to induce short-acting mydriasis and thus can be used to dilate the pupils of the eyes in vision testing. Other uses of the compounds of formulas (Ia) and (Ib) include the treatment of ulcers as well as topical use as an antiperspirant in the treatment hyperhydrosis (sweating).

The compounds of formula (Ia) and (Ib) are particularly useful in the treatment of obstructive diseases of the respiratory tract. The expression "obstructive disease of the respiratory tract" includes breathing disorders such as asthma, bronchitis, chronic obstructive pulmonary disease (COPD), allergic rhinitis and infectious rhinitis.

"Asthma" refers to a chronic lung disease causing bronchoconstriction (narrowing of the airways) due to inflammation (swelling) and tightening of the muscles around the airways. The inflammation also causes an increase in mucus production, which causes coughing that may continue for extended periods. Asthma is generally characterized by recurrent episodes of breathlessness, wheezing, coughing, and chest tightness, termed exacerbations. The severity of exacerbations can range from mild to life threatening. The exacerbations can be a result of exposure to e.g. respiratory infections, dust, mold, pollen, cold air, exercise, stress, tobacco smoke, and air pollutants.

"COPD" refers to chronic obstructive pulmonary disease, primarily but not necessarily associated with past and present cigarette smoking. It involves airflow obstruction, mainly associated with emphysema and chronic bronchitis. Emphysema causes irreversible lung damage by weakening and breaking the air sacs within the lungs. Chronic bronchitis is an inflammatory disease, which increases mucus in the airways and bacterial infections in the bronchial tubes, resulting in obstructed airflow.

"Allergic rhinitis" refers to acute rhinitis or nasal rhinitis, including hay fever. It is caused by allergens such as pollen or dust. It may produce sneezing, congestion, runny nose, and itchiness in the nose, throat, eyes, and ears.

"Infectious rhinitis" refers to acute rhinitis or nasal rhinitis of infectious origin. It is caused by upper respiratory tract infection by infectious rhinoviruses, coronaviruses, influenza viruses, parainfluenza viruses, respiratory syncytical virus, adenoviruses, coxsackieviruses, echoviruses, or Group A beta-hemolytic Streptococci and is generically referred to as the common cold. It may produce sneezing, congestion, runny nose, and itchiness in the nose, throat, eyes, and ears.

The compounds of formula (Ia) and (Ib) are also particularly useful in the treatment of overactive bladder (OAB).

Overactive bladder is a treatable medical condition that is estimated to affect 17 to 20 million people in the United States. Symptoms of overactive bladder can include urinary frequency, urinary urgency, urinary urge incontinence (accidental loss of urine) due to a sudden and unstoppable need to urinate, nocturia (the disturbance of nighttime sleep because of the need to urinate) or enuresis resulting from overactivity of the detrusor muscle (the smooth muscle of the bladder which contracts and causes it to empty).

Neurogenic overactive bladder (or neurogenic bladder) is a type of overactive bladder which occurs as a result of detrusor muscle overactivity referred to as detrusor hyperreflexia, secondary to known neurologic disorders. Patients with neurologic disorders, such as stroke, Parkinson's disease, diabetes, multiple sclerosis, peripheral neuropathy, or spinal cord lesions often suffer from neurogenic overactive bladder. In contrast, non-neurogenic overactive bladder occurs as a result of detrusor muscle overactivity referred to as detrusor muscle instability. Detrusor muscle instability can arise from non-neurological abnormalities, such as bladder stones, muscle disease, urinary tract infection or drug side effects or can be idiopathic.

Due to the enormous complexity of micturition (the act of urination), an exact mechanism which causes overactive bladder is not known. Overactive bladder can result from hypersensitivity of sensory neurons of the urinary bladder, arising from various factors including inflammatory conditions, hormonal imbalances, and prostate hypertrophy. Destruction of the sensory nerve fibers, either from a crushing injury to the sacral region of the spinal cord, or from a disease that causes damage to the dorsal root fibers as they enter the spinal cord can also lead to overactive bladder. In addition, damage to the spinal cord or brain stem causing interruption of transmitted signals can lead to abnormalities in micturition. Therefore, both peripheral and central mechanisms can be involved in mediating the altered activity in overactive bladder.

Current treatments for overactive bladder include medication, diet modification, programs in bladder training, electrical stimulation, and surgery. Currently, antimuscarinics (which are members of the general class of anticholinergics) are the primary medication used for the treatment of overactive bladder. The antimuscarinic, oxybutynin, has been the mainstay of treatment for overactive bladder. However, treatment with known antimuscarinics suffers from limited efficacy and side effects such as dry mouth, dry eyes, dry vagina, blurred vision, cardiac side effects, such as palpitations and arrhythmia, drowsiness, urinary retention, weight gain, hypertension and constipation, which have proven difficult for some individuals to tolerate. Thus, the need for new anticholinergic agents is evident.

The compounds of formula (Ia) or (Ib) may be used on their own or combined with other active substances of formula (Ia) or (Ib) according to the invention.

The compounds of formula (Ia) or (Ib) may optionally also be combined with other pharmacologically active substances. These include, in particular, betamimetics, antiallergic agents, and corticosteroids (also termed "anti-inflammatory steroids", "anti-inflammatory corticosteroids" or simply "steroids") and combinations of these active substances. The combinations with betamimetics, antiallergics or corticosteroids are of interest in the treatment of obstructive diseases of the respiratory tract, especially COPD or asthma. Accordingly, they are intended for administration by oral inhalation, as powders or aerosols.

Examples of betamimetics which may be used in conjunction with the compounds of formula (Ia) or (Ib) include compounds selected from the group consisting of bambuterol, bitolterol, carbuterol, clenbuterol, fenoterol, formoterol, hexoprenaline, ibuterol, pirbuterol, procaterol, reproterol, salmeterol, sulfphonterol, terbutaline, tulobuterol, 4-hydroxy-7-[2-{[2-{[3-(2-phenylethoxy)propyl]sulfonyl}ethyl]amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-(4-[3-(4-methoxyphenyl)-1,2,4-triazol-3-yl]-2-methyl-2-butylamino ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol and 1-(4-ethoxycarbonylamino-3-cyano-5-fluorophenyl)-2-(tert.-butylamino)ethanol, optionally in the form of their racemates, their enantiomers, their diastereomers, as well as optionally their pharmacologically acceptable acid addition salts and hydrates. It is particularly preferable to use, as betamimetics, active substances of this kind, combined with the compounds of formula (Ia) or (Ib), selected from among fenoterol, formoterol, salmeterol, 1-[3-(4-methoxybenzylamino)-4-hydroxyphenyl]-2-[4-(1 benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of their racemates, their enantiomers, their diastereomers, as well as optionally their pharmacologically acceptable acid addition salts and hydrates. Of the betamimetics mentioned above, the compounds formoterol and salmeterol, optionally in the form of their racemates, their enantiomers, their diastereomers, as well as optionally their pharmacologically acceptable acid addition salts and hydrates, are particularly important.

The acid addition salts of the betamimetics selected from among the hydrochloride, hydrobromide, sulfate, phosphate, fumarate, methanesulfonate and xinafoate are preferred according to the invention. In the case of salmeterol, the salts selected from among the hydrochloride, sulfate and xinafoate are particularly preferred, especially the sulfates and xinafoates. In the case of formoterol, the salts selected from among the hydrochloride, sulfate and fumarate are particularly preferred, especially the hydrochloride and fumarate. Of outstanding importance is formoterol fumarate.

The corticosteroids which may optionally be used in conjunction with the compounds of formula (Ia) or (Ib), include compounds selected from among flunisolide, beclomethasone, triamcinolone, budesonide, fluticasone, mometasone, ciclesonide, rofleponide, GW 215864, KSR 592, ST-126, loteprednol etabonate, etiprednol dichloracetate and dexamethasone. The preferred corticosteroids are those selected from among flunisolide, beclomethasone, triamcinolone, loteprednol etabonate, etiprednol dichloracetate, budesonide, fluticasone, mometasone, ciclesonide and dexamethasone, while budesonide, fluticasone, loteprednol etabonate, etiprednol dichloracetate, mometasone and ciclesonide, especially budesonide, fluticasone, loteprednol etabonate and etiprednol dichloracetate, are of particular importance. Any reference to steroids herein also includes a reference to salts or derivatives which may be formed from the steroids. Examples of possible salts or derivatives include: sodium salts, sulfobenzoates, phosphates, isonicotinates, acetates, propionates, dihydrogen phosphates, palmitates, pivalates or furoates. The corticosteroids may optionally also be in the form of their hydrates.

When the corticosteroid is loteprednol etabonate, it may be advantageously combined with an enhancing agent selected from the group consisting of:

(a) 11β,17α-dihydroxyandrost-4-en-3-one-17β-carboxylic acid (cortienic acid, or CA);
(b) 11β,17α-dihydroxyandrosta-1,4-dien-3-one-17β-carboxylic acid ($\Delta^1$ cortienic acid or $\Delta^1$-CA);
(c) methyl 11β,17α-dihydroxyandrost-4-en-3-one-17β-carboxylate (cortienic acid methyl ester, or MeCA);
(d) ethyl 11β,17α-dihydroxyandrost-4-en-3-one-17β-carboxylate (cortienic acid ethyl ester, or EtCA);
(e) methyl 11β,17α-dihydroxyandrosta-1,4-dien-3-one-17β-carboxylate (($\Delta^1$ cortienic acid methyl ester, or $\Delta^1$-MeCA); and
(f) ethyl 11β,17α-dihydroxyandrosta-1,4-dien-3-one-17β-carboxylate ($\Delta^1$ cortienic acid ethyl ester, or $\Delta^1$-EtCA),
wherein the mole ratio of loteprednol etabonate to enhancing agent is from about 5:1 to about 0.5:1. Such combinations with these inactive metabolites are described in detail in WO 2005/000317 A1, incorporated by reference herein in its entirety and relied upon.

Examples of antiallergic agents which may be used as a combination with the compounds of formula (Ia) or (Ib) include epinastin, cetirizin, azelastin, fexofenadin, levocabastin, loratadine, mizolastin, ketotifen, emedastin, dimetinden, clemastine, bamipin, cexchloropheniramine, pheniramine, doxylamine, chlorophenoxamine, dimenhydrinate, diphenhydramine, promethazine, ebastin, desloratidine and meclizine. Preferred antiallergic agents which may be used in combination with the compounds of formula (Ia) or (Ib) are selected from among epinastin, cetirizin, azelastin, fexofenadin, levocabastin, loratadine, ebastin, desloratidine and mizolastin, epinastin and desloratidine being particularly preferred. Any reference to the abovementioned antiallergic agents also includes a reference to any pharmacologically acceptable acid addition salts thereof which may exist.

When the compounds of formula (Ia) or (Ib) are used in conjunction with other active substances, the combination with steroids or betamimetics is particularly preferred of the various categories of compounds mentioned above.

Whether or not the compounds of formula (Ia) or (Ib) are used in conjunction with other active substances as described above, they are typically administered in the form of a pharmaceutical composition comprising an anticholinergically effective amount of a compound of formula (Ia) or (Ib) and a non-toxic pharmaceutically acceptable carrier therefor. Pharmaceutically acceptable carriers, or diluents, are well-known in the art. The carriers may be any inert material, organic or inorganic, suitable for administration, such as: water, gelatin, gum arabic, lactose, microcrystalline cellulose, starch, sodium starch glycolate, calcium hydrogen phosphate, magnesium stearate, talcum, colloidal silicon dioxide, and the like. Such compositions may also contain other pharmaceutically active agents, as noted above, and/or conventional additives such as stabilizers, wetting agents, emulsifiers, flavoring agents, buffers, binders, disintegrants, lubricants, glidants, antiadherents, propellants, and the like. The carrier, e.g., non-active ingredient, can be just (sterile) water with the pH adjusted to where the active pharmaceutical agent is very soluble. It is preferred that the pH be at or near 7. Alternatively and preferably, the non-active carrier agent should be physiological saline with the pH adjusted appropriately.

The novel compounds of formula (Ia) or (Ib) can be administered in any suitable way. The compounds can be made up in solid or liquid form, such as tablets, capsules, powders, syrups, elixirs and the like, aerosols, sterile solutions, suspensions or emulsions, and the like.

The compounds of formula (Ia) or (Ib) can be brought into suitable dosage forms, such as compositions for administration through the oral, rectal, tranderrmal, parenteral, nasal, pulmonary (typically via oral inhalation) or topical (including ophthalmic) route in accordance with accepted pharmaceutical procedures. The route of administration and thus the dosage form will be chosen in light of the condition to be treated with the instant anticholinergic agents. By way of illustration only, when the compound of formula (Ia) or (Ib) is administered to treat COPD or asthma, or other serious obstructive disease of the respiratory tract, the compounds may be advantageously administered via inhalation or insufflation; for such purposes, the compounds are advantageously in the form of an aerosol or a powder for inhalation. When administered to treat less serious respiratory disorders such as rhinitis, a nasal spray, mist or gel may be advantageous. For inducing mydriasis, an ophthalmic formulation such as eye drops may be most appropriate. For OAB, a formulation for oral administration such as tablet or capsules or a transdermal preparation may be preferred. For treating hyperhydrosis, an topical preparation formulated as an antiperspirant stick, gel, spray, cream or the like would be preferred.

For purposes of illustration, dosages are expressed based on the inhalation of an aerosol solution, such as the product Atrovent Inhalation Aerosol (Boehringer Ingelheim). Adjustments in dosages for administration by other modes of inhaled administration are well known to those skilled in the art.

In general, a therapeutically effective or anticholinergically effective amount of compound of formula (Ia) or (Ib) is from about 1 μg to about 1,000 μg, e.g., from about 10 μg to about 1.000 μg or from about 100 μg to about 1000 μg. However, the exact dosage of the specific compound of formula (Ia) or (Ib) will vary depending on its potency, the mode of administration, the age and weight of the subject and the severity of the condition to be treated. The daily dosage may, for example, range from about 0.01 μg to about 10 μg per kg of body weight, administered singly or multiply in doses e.g. from about 1 μg to about 1,000 μg each. The compounds of formula (Ia) or (Ib) can be administered from one to four times daily, e.g., once or twice daily.

The dosage form for inhalation can be an aerosol. The minimum amount of an aerosol delivery is about 0.2 ml and the maximum aerosol delivery is about 5 ml. The concentration of the compounds of formula (Ia) or (Ib) may vary as long as the total amount of spray delivered is within the about 0.2 to about 5 ml amount and as long as it delivers an anticholinergically effective amount of the compound of formula (Ia) or (Ib). It is well known to those skilled in the art that if the concentration is higher, one gives a smaller dose to deliver the same effective amount.

The dosage form for inhalation can also be via intranasal spray. The minimum amount of an aerosol delivery is about 0.02 ml per nostril and the maximum aerosol delivery is about 0.2 ml per nostril. The concentration of the compounds of formula (Ia) or (Ib) may vary as long as the total amount of spray delivered is within about 0.02 ml per nostril to about 0.2 ml per nostril, e.g., between about 0.05 ml per nostril and about 0.08 ml per nostril, and it delivers an anticholinergically effective amount of the compound of formula (Ia) or (Ib).

Of course, the volume of aerosol or intranasal spray for delivering an anticholinergically effective amount of the compound of formula (Ia) or (Ib) depends upon the concentration of the compound in the aerosol or intranasal spray, i.e., higher concentrations of the compound of formula (Ia) or (Ib) require smaller dosage volumes to deliver a therapeutically effective amount and lower concentrations of the compound of formula (Ia) or (Ib) require larger dosage volumes to deliver the same anticholinergically effective amount.

Aerosols for inhalation of various pharmaceutical agents are well known to those skilled in the art, including many aerosols for treating asthma. Aerosols may be produced with a nebulizer. Typically, the nebulizer is charged with a carrier solution and the compound of formula (Ia) or (Ib) in an amount sufficient to effectively deliver an anticholinergically effective amount of the compound of formula (Ia) or (Ib). For instance, depending upon the nebulizer and its operating conditions, the nebulizer may be charged with several hundred mg of anticholinergic compound in order to deliver about 1 μg to about 1000 μg, e.g., from about 10 μg to about 1000 μg or from about 50 μg to about 500 μg, of the compound of formula (Ia) or (Ib).

The dosage form for inhalation may also be in powder form. Powders for inhalation of various pharmaceutical agents are well known to those skilled in the art, including many powders for treating asthma. When the dosage form is a powder, the compounds of formula (Ia) or (Ib) can be administered in pure form or diluted with an inert carrier. When an inert carrier is used, the compounds are compounded such that the total amount of powder delivered delivers an "effective amount" of the compounds according to the invention. The actual concentration of the active compound may vary. If the concentration is lower, then more powder must be delivered, if the concentration is higher, less total material must be delivered to provide an effective amount of the active compound according to the invention. Any of the foregoing pharmaceutical compositions may further comprise one or more additional active substances, particularly corticosteroids and/or betamimetics as discussed earlier.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Suitable preparations for administering the compounds of formula (Ia) or (Ib) include tablets, capsules, suppositories, solutions, etc. Of particular importance (particularly when treating asthma or COPD or other respiratory disorders) is the administration of the compounds by inhalation. The proportion of pharmaceutically active compound or compounds should be in the range from 0.05 to 90% by weight, preferably 0.1 to 50% by weight of the total composition. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatin, lubricants such as magnesium stearate or talc and/or agents for delaying release, such as carboxymethyl cellulose, cellulose acetate phthalate, or polyvinyl acetate. The tablets may also comprise several layers. Tablets and other solid oral formulations are of particular interest in the treatment of OAB or ulcers while opthalmic solutions, suspensions and gels are of special interest for inducing mydriasis and topical gels, solids and sprays are of particular use as antiperspirants.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances of formulas (Ia) or (Ib) or combinations thereof as described above may additionally contain a sweetener such as saccharin, cyclamate, aspartame, sucralose, glycerol or sugar and a flavor enhancer, e.g. a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates, or stabilizers such as alkali metal salts of ethylenediamine tetraacetic acid, optionally using emulsifiers and/or dispersants, while if water is used as the diluent, for example, organic solvents may optionally be used as solvating agents or dissolving aids, and transferred into injection vials or ampules or infusion bottles.

Capsules containing one or more active substances or combinations of active substances may for example be prepared by mixing the active substances with inert carriers such as lactose or sorbitol and packing them into gelatin capsules. Suitable suppositories may be made for example by mixing with carriers provided for this purpose, such as neutral fats or polyethyleneglycol or the derivatives thereof. Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulfite liquors, methylcellulose, starch and polyvinylpyrrolidone) and lubricants (e.g. magnesium stearate, talc, stearic acid and sodium lauryl sulphate).

The preparations are administered by the usual methods, preferably by inhalation in the treatment of asthma or COPD or other respiratory disorders. For oral administration the tablets may, of course, contain, apart from the above-mentioned carriers, additives such as sodium citrate, calcium carbonate and dicalcium phosphate together with various additives such as starch, preferably potato starch, gelatin and the like. Moreover, lubricants such as magnesium stearate, sodium lauryl sulfate and talc may be used at the same time for the tabletting process. In the case of aqueous suspensions the active substances may be combined with various flavor enhancers or colorings in addition to the excipients mentioned above.

The dosage of the compounds of formula (Ia) and (Ib) is naturally greatly dependent on the route of administration and the complaint to be treated. When administered by inhalation the compounds of formula (Ia) or (Ib) are characterized by high efficacy even at doses in the μg range. The compounds of formula (Ia) or (Ib) can also be used effectively above the μg range. The dosage may then be in the gram range, for example. Particularly when administered by a method other than inhalation, the compounds according to the invention may be given in higher doses (in the range from 1 to 1000 mg, for example, although this does not imply any limitation).

The compounds of formula (Ia) and (Ib), combinations of a compound of formula (Ia) or (Ib) with one or more other active agents, and compositions comprising a compound of formula (Ia) or (Ib), with or without one or more other active agents, as described hereinabove are thus useful in a method for eliciting an anticholinergic response in a subject in need of same, comprising administering to said subject an anticholinergically effective amount of said compound or composition. In particular embodiments, the method is for treating an obstructive disease of the respiratory tract, especially when the disease is chronic obstructive pulmonary disease or asthma, or for treating overactive bladder. In another embodiment, the method comprises inducing mydriasis in the eye(s) of a subject in need of such treatment, comprising topically applying to the eye(s) of said subject a mydriatically effective amount of a compound of formula (Ia) or (Ib) or combination or composition comprising it as described hereinabove. Use of compounds of formula (Ia) or (Ib) in the preparation of a medicament for treating a condition responsive to an anticholinergic agent (such as any of these conditions disclosed above) is likewise provided herein.

In particular embodiments there are provided combinations of the compound of formula (Ia) or (Ib) with other active agents, especially one or more antiinflammatory corticosteroids, betamimetic agents or antiallergic agents. In the combination products, the active agents are present in a combined amount effective to treat the target condition, especially to treat an obstructive disease of the respiratory tract, most especially to treat chronic obstructive pulmonary disease or asthma. In preferred embodiments, the other active agent is a betamimetic agent or an antiinflammatory corticosteroid. Of particular interest are combinations of a compound of formula (Ia) or (Ib) and a corticosteroid, especially loteprednol etabonate or etiprednol dichloracetate. When loteprednol etabonate is selected as the corticosteroid, its activity can be enhanced by combination with cortienic acid or $\Delta^1$-cortienic acid or a methyl or ethyl ester of cortienic acid or $\Delta^1$-cortienic acid, in a mole ratio of from about 5:1 to about 0.5:1. A molar ratio of about 1:1, which can be approximated by a 1:1 ratio by weight, is particularly convenient.

Initial Studies
Materials and Methods
Materials

Glycopyrrolate (glycopyrronium bromide) was kindly provided by Boehringer Ingelheim Chemicals, Inc. Carbamylcholine bromide (carbachol), atropine methylbromide (atropine MeBr), and scopolamine methylbromide (scopolamine MeBr) were obtained from Sigma Chemicals Co. (St. Louis, Mo.). N-[$^3$H]-Methyl-scopolamine (NMS) was obtained from Amersham Biosciences UK Limited (Buckinghamshire, UK). Cloned human muscarinic receptor subtypes $M_1$-$M_4$ were obtained from Applied Cell Science Inc. (Rockville, Md.). Scintiverse BD was from Fisher Scientific Co. (Pittsburgh, Pa.).

Chemicals used for synthesis were reagent or HPLC grade, and were obtained from Aldrich (Milwaukee, Wis.) and Fisher Scientific Co. Melting points were taken on Fisher-Johns melting apparatus. NMR spectra were recorded on a Bruker Advance 500 MHz NMR spectrometer and are reported in ppm relative to TMS. Elemental analyses were performed by Atlantic Microlab Inc (Atlanta, Ga.).

Synthesis

Racemic Cyclopentylmandelic Acid (1)

Cyclopentylmagnesium bromide ether solution (100 ml, 2M; 0.2 mol) was added drop-wise to benzoylformic acid (15 g, 0.1 mol) in 330 ml of anhydrous ethyl ether at 0° C. The mixture was stirred at 0° C. for 30 min and at room temperature for 24 h. The reaction mixture was treated with 1 N HCl, and the aqueous solution was extracted with ether. The combined ether solution was treated with $K_2CO_3$ solution. The potassium carbonate solution was acidified with HCl and extracted with ether twice. The ether solution was dried with anhydrous sodium sulfate and evaporated to give a crude product. The crude product was washed with water to get pure racemic cyclopentylmandelic acid 1 (8.0 g, 36.4%). Needle-like crystals, m.p.: 153-154° C. $^1$H NMR (CDCl$_3$, 500 MHz): 1.28-1.39, 1.42-1.50, 1.51-1.61, 1.63-1.72 [8H, m, (CH$_2$)$_4$], 2.93 [1H, p, CHC(OH)], 7.26-7.30, 7.33-7.36, 7.65-7.67 (5H, m, Ph) ppm.

Methyl cyclopentylmandelate (2)

To a mixture of racemic cyclopentylmandelic acid R/S(±)1 (4.47 g, 20 mmol) and potassium carbonate (7.01 g, 50 mmol) in DMF (50 ml), methyl iodide (8.64 g, 60 mmol) was added at room temperature. The mixture was stirred at room temperature for 2 h, and then poured into water and extracted with hexanes three times. Evaporation of the dried hexanes extract gave a crude product. Flash chromatography of the crude product on silica gel with 1.5:1 hexanes:methylene chloride gave the pure product 2 (3.02 g, 64%). $^1$H NMR (CDCl$_3$, 300 MHz): 1.32-1.37, 1.43-1.69 [8H, m, (CH$_2$)$_4$], 2.90 [1H, p, CHC(OH)], 3.74 (1H, s, OH), 3.77 (3H, s, CH$_3$), 7.25-7.37, 7.63-7.65 (5H, m, Ph) ppm.

N-Methyl-3-pyrrolidinyl cyclopentylmandelate (4)

A solution of 2 (2.20 g, 9.4 mmol) and N-methyl-3-pyrrolidinol (0.3, 1.30 g, 13 mmol) in 40 ml of n-heptane was heated until 20 ml of heptane had been distilled. About 0.003 g of sodium was added, and the solution was stirred and heated for 2 h as the distillation was continued. More heptane was added at such a rate as to keep the reaction volume constant. Additional sodium was added at the end of an hour. The solution was then cooled and extracted with 3N HCl. The acid extract was made alkaline with concentrated NaOH and extracted three times with ether. Removal of the dried ether solution gave a crude oil. Flash chromatography of the crude product on silica gel with 8:1 EtOAc:EtOH gave pure product 4 (2.053 g, 72%). Analysis for C$_{18}$H$_{25}$NO$_3$. Calcd: C, 71.26; H, 8.31; N, 4.62. Found: C, 71.55; H, 8.44; N, 4.68. $^1$H NMR (CDCl$_3$, 500 MHz): 1.27-1.35, 1.40-1.47, 1.54-1.60, 1.75-1.90 [8H, m, (CH$_2$)$_4$], 2.12-2.30, 2.52-2.57, 2.64-2.81 (6H, m CH$_2$NCH$_2$CH$_2$), 2.33, 2.36 (3H, 2s, NCH$_3$), 2.93 [(1H, p, CHC(OH)], 3.83 (1H, bs, OH), 5.23 (1H, m, CO$_2$CH), 7.23-7.36, 7.64-7.67 (5H, m, Ph) ppm.

3-(2-Cyclopentyl-2-phenyl-2-hydroxyacetoxy)-1-(methoxycarbonylmethyl)-1-methylpyrrolidinium bromide, Compound (a)

To compound 4 (0.8235 g, 2.71 mmol) in 30 ml of dry acetonitrile, methyl bromoacetate (1.08 g, 7.06 mmol) was added at room temperature. The mixture was stirred for 2 h. Evaporation of acetonitrile gave a crude product. The crude product was dissolved in a small volume of methylene chloride and then poured into 100 ml of dry ethyl ether to precipitate. This procedure was repeated three times to obtain Compound (a) as pure product (0.9912 g, 80%). White powder, m.p.: 192-194° C. Analysis for C$_{21}$H$_{30}$BrNOs. Calcd: C, 55.27; H, 6.63; N, 3.07. Found: C, 55.11; H, 6.59; N, 3.03. $^1$H NMR (CDCl$_3$, 500 MHz): 1.23-1.29, 1.31-1.37, 1.41-1.47, 1.53-1.67 [8H, m, (CH$_2$)], 2.18-2.23, 2.73-2.80, 4.04-4.16, 4.21-4.25 (6H, m, CH$_2$NCH$_2$CH$_2$), 2.85 [1H, p, CHC(OH)], 3.57 (3H, s, NCH$_3$), 3.80 (3H, s, CO$_2$CH), 4.66, 4.85 (2H, 2dd, CH$_2$CO$_2$), 5.27 (1H, s, OH), 5.52 (1H, m, CO$_2$CH), 7.25-728, 7.32-7.35, 7.57-7.59 (5H, m, Ph) ppm.

3-(2-Cyclopentyl-2-phenyl-2-hydroxyacetoxy)-1-(ethoxycarbonylmethyl)-1-methylpyrrolidinium bromide, Compound (b)

To compound 4 (0.369 g, 122 mmol) in 10 ml of dry acetonitrile, ethyl bromoacetate (0.377 g, 2.25 mmol) was added at room temperature. The mixture was stirred for 2 h. Evaporation of acetonitrile gave a crude product. The crude product was dissolved in a small volume of ethylene chloride and then poured into 50 ml of dry ethyl ether to precipitate. This procedure was repeated three times to obtain Compound (b) as pure product (0.45 g, 79%). White powder, m.p.: 192-194° C.

Analysis for $C_{22}H_{32}BrNO_5$. Calcd: C, 56.17; H, 6.86; N, 2.98. Found: C, 56.14; H, 6.89; N, 2.94. $^1$H NMR (CDCl$_3$, 500 MHz): 1.35 (3H, t, CH$_3$CH$_2$), 1.26-1.33, 1.42-1.47, 1.55-1.67 [8H, m, (CH$_2$)$_4$], 2.14-2.21, 2.73-2.79, 4.12-4.17, 4.22-4.29 (6H, m, CH$_2$NCH$_2$CH$_2$), 2.86 [1H, p, CHC(OH)], 3.62 (3H, s, NCH$_3$), 4.25 (2H, q, CH$_3$CH$_2$), 4.67, 4.83 (2H, dd, CH$_2$CO$_2$), 4.91 (1H, s, OH), 5.53 (1H, m, CO$_2$CH), 7.25-7.27, 7.32-7.34, 7.57-7.59 (5H, m, Ph) ppm.

Resolution of racemic cyclopentylmandelic acid (1)

(−)-Strychnine (6.10 g) in 50 ml of methanol (suspension) was added to racemic cyclopentylmandelic acid 1. (3.96 g) in methanol (20 ml) at room temperature. The reaction solution was let to stand for overnight. The crystals were removed by filtration and crystallized again with hot methanol. The second crop of crystals was collected by filtration and treated with sodium hydroxide solution. The basic solution was extracted with methylene chloride twice (methylene chloride solution discarded), and then acidified with hydrochloric acid to recover the resolved cyclopentylmandelic acid. To this resolved acid (20.6 mg in 0.1 ml of ethyl acetate), 13 µL of (+)-α-phenylethylamine was added. The precipitate which formed was washed with hexane three times and dried under vacuum. The precipitate was identified by NMR as optically pure cyclopentylmandelic acid, R(−)1, (1.49 g, 37.6%). M.p.: 121-122° C. $[\alpha]^{25}_D$=−22.5° (c=1 g/100 ml, CHCl$_3$). $^1$H NMR (CDCl$_3$, 500 MHz): 1.28-1.39, 1.42-1.50, 1.51-1.61, 1.64-1.73 [8H, m, (CH$_2$)$_4$], 2.93 [1H, p, CHC(OH)], 7.25-7.28, 7.32-7.35, 7.64-7.65 (5H, m, Ph) ppm.

Methyl (−)-cyclopenylmandelate, R(−)$_2$

To a mixture of (−)-cyclopentylmandelic acid, R(−)1, (1.83 g, 8.3 mmol) and potassium carbonate (2.87 g, 21 mmol) in DMF (21 ml), methyl iodide (3.53 g, 25 mmol) was added at room temperature. The mixture was stirred at room temperature for 2 h, and then poured into water and extracted with hexanes three times. Evaporation of the dried hexanes extract gave a crude product. Flash chromatography of the crude product on silica gel with 1.5:1 hexanes:methylene chloride gave pure product R(−)$_2$ (1.95 g, 100%). Analysis for $C_{18}H_{18}O_3$. Calcd: C, 71.77; H, 7.74. Found: C, 71.88; H, 7.80. $^1$H NMR (CDCl$_3$, 500 MHz): 1.32-1.36, 1.43-1.61 [8H, m, (CH$_2$)$_4$], 2.90 [1H, p, CHC(OH)], 3.71 (1H, s, OH), 3.79 (3H, s, CH$_3$), 7.25-7.28, 7.31-7.35, 7.63-7.65 (5H, m, Ph) ppm.

N-Methyl-3-pyrrolidinyl (−)-cyclopentylmandelate, 2R-4

A solution of R(−)$_2$ (1.85 g, 7.9 mmol) and N-methyl-3-pyrrolidinol (3, 1.05 g, 10.4 mmol) in 40 ml of n-heptane was heated until 20 ml of heptane had distilled. Approximately 0.003 g of sodium was added, and the solution was stirred and heated for 2 h as the distillation was continued. More heptane was added at such a rate as to keep the reaction volume constant. Additional sodium was added at the end of an hour. The solution was then cooled and extracted with 3N HCl. The acid extract was made alkaline with concentrated NaOH and extracted three times with ether. Removal of dried ether solution gave a crude oil. Flash chromatography of the crude product on silica gel with 8:1 EtOAc:EtOH gave 2R-4 as a mixture of two diastereoisomers in an NMR-estimated ratio of 1:1, (1.68 g, 70%). Analysis for $C_{18}H_{25}NO_3 \cdot 0.2H_2O$. Calcd: C, 70.42; H, 8.34; N, 4.5. Found: C, 70.60; H, 8.26; N, 4.63. $^1$H NMR (CDCl$_3$, 500 MHz): 1.28-1.37, 1.40-1.47, 1.51-1.70, 1.73-1.80, 1.83-1.90 [8H, m, (CH$_2$)$_4$], 2.14-2.21, 2.27-2.35, 2.36-2.42, 2.52-2.55, 2.64-2.81 (6H, m, CH$_2$NCH$_2$CH$_2$), 2.33, 2.37 (3H, 2s, NCH$_3$), 2.93 [1H, p, CHC(OH)], 3.78 (1H, bs, OH), 5.22 (1H, m CO$_2$CH), 7.24-7.27, 7.31-7.35, 7.64-7.66 (5H, m, Ph) ppm.

(2R) 3-(2-Cyclopentyl-2-phenyl-2-hydroxyacetoxy)-1-(methoxycarbonylmethyl)-1-methylpyrrolidinium bromide, Compound (c)

To compound 2R-4 (0.15 g, 0.49 mmol) in 6 ml of dry acetonitrile, methyl bromoacetate (0.194 g, 1.27 mmol) was added at room temperature. The mixture was stirred for 6 h. Evaporation of acetonitrile gave a crude product. The crude product was dissolved in a small volume of methylene chloride and then poured into 50 ml of dry ethyl ether to precipitate. This procedure was repeated three times to obtain the product, Compound (c) (0.1879 g, 83%), as a mixture of four diastereoisomers in an NMR-estimated ratio of 1:1:2:2. White powder, m.p.: 153-155° C. $[\alpha]^{25}_D$=+0.5° (c=1 g/100 ml CHCl$_3$). Analysis for $C_{21}H_{30}BrNO_5 \cdot 0.2H_2O$. Calcd: C, 54.86; H, 6.62; N, 3.05. Found: C, 54.75; H, 6.66; N, 3.01. $^1$H NMR (CDCl$_3$, 500 MHz): 130-1.37, 1.41-1.50, 1.55-1.73 [8H, m, (CH$_2$)$_4$], 1.93-2.00, 2.12-2.26, 2.75-2.95, 3.00-3.03, 4.30-4.50, 4.57-4.61 [7H, m, CHC(OH) and CH$_2$NCH$_2$CH$_2$], 3.09, 3.30 (1H, 2s, OH), 3.64, 3.66, 3.84, 3.95, 3.97 (3H, is, NCH$_3$), 3.74, 3.77, 3.79, 3.81 (3H, 4s, CO$_2$CH$_3$), 4.78, 4.83; 4.90, 4.97; 5.30, 5.35; 5.37, 5.41 (2H, 4 groups of 2dd, CH$_2$CO$_2$), 5.53 (1H, m, CO$_2$CH), 7.23-7.29, 7.31-7.38, 7.56-7.60 (5H, m, Ph) ppm.

(2R) 3-(2-Cyclopentyl-2-phenyl-2-hydroxyacetoxy)-1-(ethoxycarbonylmethyl)-1-methylpyrrolidinium bromide, Compound (d)

To compound 2R-4 (0.22 g, 0.73 mmol) in 10 ml of dry acetonitrile, ethyl bromoacetate (0.21 ml, 0.316 g, 1.89 mmol) was added at room temperature. The mixture was stirred for 22 hours. Removal of acetonitrile gave a crude product. The crude product was dissolved in small volume of ethylene chloride and then poured into 50 ml of dry ethyl ether to precipitate. This procedure repeated three times to obtain the product, Compound (d) (0.3085 g, 90%) as a mixture of four diastereoisomers in an NMR-estimated ratio of 1:1:2:2. White powder, m.p.:143-145° C. $[\alpha]^{25}_D$=+5.6° (c=1 g/100 ml CHCl$_3$). Analysis for $C_{22}H_{32}BrNO_5 \cdot 0.3H_2O$. Calcd: C, 55.53; H, 6.91; N, 2.94. Found: C, 55.46; H, 6.85; N, 2.97. $^1$H NMR (CDCl$_3$, 500 MHz): 1.26, 1.28, 1.32, 1.35 (3H, 4t, CH$_3$CH$_2$), 1.44-1.50, 1.53-1.63, 1.65-1.70 [8H, m, (CH$_2$)$_4$], 1.93-2.00, 2.04-2.11, 2.18-2.25, 2.76-2.96, 3.01-3.04, 4.09-4.26 [7H, m, CHC(OH) and CH$_2$NCH$_2$CH$_2$], 3.06, 3.28 (1H, 2s, 01-1), 3.66, 3.69, 3.81, 3.82, 3.94, 3.96 (3H, 6s, NCH$_3$), 4.61, 4.69; 4.76, 4.85; 5.17, 5.22; 5.26, 5.30 (2H, 4 set of dd, $CH_2CO_2$), 4.26-4.52 (2H, m, $CH_3CH_2$), 5.53 (1H, m, $CO_2CH$), 7.24-7.29, 7.31-7.38, 7.56-7.60 (5H, m, Ph) ppm.

pH Profile

The stabilities of the soft glycopyrrolates in standard phosphate buffers (0.05 M) of various pH (pH 6.00-8.40) were investigated at 37'C. Aliquots of 4.4 mM of the compounds in water solution were added to the buffer solutions to give a final concentration of 0.44 mM. At appropriate time intervals, samples were taken and analyzed by HPLC to monitor the disappearance of the soft analogs and the formation of its hydrolysis products. The pseudo-first-order rate constant (k, $min^{-1}$) and half-life ($t_{1/2}$, min) of the disappearance of the compound in the buffer were calculated.

In Vitro Studies

The stability of soft glycopyrrolates in biological media in vitro was determined by measuring the pseudo-first-order rate constants (k, $min^{-1}$) and half-lives ($t_{1/2}$, min) of the disappearance of the compound in rat blood and plasma. Aliquots of 22 mM were added to the biological medium at 37° C. to yield a final concentration of 0.7 mM. At appropriate time intervals, samples (0.15 ml) were withdrawn and mixed with 0.3 ml of 5% dimethylsulfoxide in acetonitrile solution. The mixtures were centrifuged, and the supernatants were analyzed by HPLC. Experiments were performed in triplicates.

Analytical Method

The HPLC system used for the analysis of the compounds of formula (I) and their hydrolysis products was as follows: A Supelcosil LC-8 column (25 cm×4.6 mm) was used with a mobile phase of acetonitrile (42%) and aqueous solution (58%) containing sodium phosphate (10 mM), acetic acid (0.1%), and triethylamine (0.1%). At a flow rate of 1 ml/min, the retention times were 6.02 min for Compounds (a) and (c), 7.27 min for Compounds (b) and (d) and 4.14 min (hydrolysis product), respectively. With an injection volume of 10 μl, the detection limit was 1 μg/ml.

Receptor Binding Affinity

Receptor binding studies were performed with N-[$^3$H]-methylscopolamine (NMS) in assay buffer (phosphate-buffered saline, PBS, without $Ca^{++}$ or $Mg^{++}$, pH 7.4) following the protocol obtained from Applied Cell Science Inc. (Rockville, Md.). A 10 mM NaF solution was added to the buffer as an esterase inhibitor. The assay mixture (0.2 ml) contained 20 μl diluted membranes (receptor proteins, final concentration: $M_1$, 38 μg/ml; $M_2$, 55 μg/ml; $M_3$, 27 μg/ml; and $M_4$, 84 μg/ml). The final concentration of NMS for the binding studies was 0.5 nM. Specific binding was defined as the difference in [$^3$H]NMS binding in the absence and presence of 5 μM atropine for $M_1$ and $M_2$ or 1 μM atrophic for $M_3$ and $M_4$. Incubation was carried out at room temperature for 120 min. The assay was terminated by filtration through a Whatman GF/C filter (presoaked with 0.5% polyethyleneimine). The filter was then washed six times with 1 ml ice cold buffer (50 mM Tris-HCl, pH 7.8, 0.9% NaCl), transferred to vials, and 5 ml of Scintiverse was added. Final detection was performed on a Packard 31800 liquid scintillation analyzer (Packard Instrument Inc., Downer Grove, Ill.). Data obtained from the binding experiments were fitted to the %[$^3$H] NMS bound $100-[100x^n/k/(1+x^n/k)]$ equation, to obtain the Hill coefficient n, and then to %[$^3$H] NMS bound=$100-[100x^n/IC_{50}/(1+x^n/IC_{50})]$, to obtain $IC_{50}$s (x being the concentration of the tested compound). Based on the method of Cheng and Prusoff (Cheng & Prusoff 1973), $K_i$ was derived from the equation $K_i=IC_{50}/(1+L/K_d)$, where L is the concentration of the radioligand. $IC_{50}$ represents the concentration of the drug causing 50% inhibition of specific radioligand binding, and $K_d$ represents the dissociation constant of the radioligand receptor complex. Experiments were performed in triplicates. Data were analyzed by a non-linear least-square curve-fitting procedure using Scientist software (MicroMath Inc., Salt Lake City, Utah).

$pA_2$ Values

Male guinea pigs obtained from Harlan Sprague Dawley Inc. (Indianapolis, Ind.) and weighing about 400 g were used after overnight fasting. Animals were sacrificed by decapitation, and the ileum (the region of 5 cm upward of the cecum) was isolated and removed. The ileum was cut into 2.5 cm pieces and suspended in an organ bath containing 30 ml of mixture of Tyrode's solution and 0.1 mM hexamethonium bromide. The organ bath was constantly aerated with oxygen and kept at 37° C. One end of the ileum strip was attached to a fixed support at the bottom of the organ bath, and the other end to an isometric force transducer (Model TRN001, Kent Scientific Corp., Conn.) operated at 2-10 g range. The ileum strip was kept at a 2 g tension, and carbachol was used as antagonist. The ileum contracted cumulatively upon the addition of consecutive doses of carbachol (10-20 μl of $2\times10^{-4}$–$2\times10^{-3}$ M in water solution). Contractions were recorded on a physiograph (Kipp & Zonen Flarbed Recorder, Holland). After the maximum response was achieved, the ileum was washed three times, and a fresh Tyrode's solution containing appropriate concentration of the antagonist [Compound (a), (b), (c) or (d), glycopyrrolate, or scopolamine] was replaced. An equilibration time of 10 min was allowed for the antagonists before the addition of carbachol. Four to six trials were performed for each antagonist.

Pharmacological Activities of Soft Glycopyrrolates

The mydriatic effects of the soft drugs (a), (b), (c) and (d) in rabbit eyes have been compared with that of glycopyrrolate. Four healthy male New-Zealand white rabbits weighting about 3.5 kg were used. To investigate the dose-mydriatic-response relationships, 100 μl of various concentrations of the compounds (0, 0.5, and 1% for the soft drugs and 0, 0.05, 0.1, and 0.2% for glycopyrrolate) were administered in the eyes to determine the pharmacodynamically equivalent doses, the lowest doses that induce the maximum pupil dilations. Drug solutions were applied to one eye; only water was applied to the other eye that served as control. Experiments were carried out in a light- and temperature-controlled room. At appropriate time intervals, the pupil diameters of both eyes were recorded. Difference in pupil diameters between each time-point and zero time-point were calculated for both treated and control eyes and reported as mydriatic responses [(treated-control)/control in %]. Control eye dilations were monitored to determine whether systemic absorption had occurred or not. For each compound, four trials have been conducted. Animal studies were performed in accordance with the Guide for the Care and Use of Laboratory Animals adopted by the National Institute of Health, USA. Institutional animal care and use committee (IACUC) approval was obtained prior to the initiation of this research and during its execution.

Statistical Analysis

Stability, receptor binding, and $pA_2$ activities were compared using both t-tests and nonparametric Mann-Whitney U tests for the compound-pairs of interest. Pharmacological activities (maximum response $R_{max}$ % and area under the effect curves $AUC^{eff}$) were compared using ANOVA followed by Tukey-Kramer multiple comparison tests as a parametric post hoc test (Jones 2002), A significance level of $p<0.05$ was used in all cases. All statistical analyses were performed using NCSS (Number Cruncher Statistical Systems, Kaysville, Utah, USA).

Results and Discussion
Synthesis

The new soft glycopyrrolate derivatives, compounds (a) and (b) [3-(2-cyclopentyl-2-phenyl-2-hydroxyacetoxy)-1-(alkoxycarbonylmethyl)-1-methylpyrrolidinium bromide; alkoxy being methoxy and ethoxy for (a) and (b), respectively], have been synthesized as shown in Scheme 1 except for the second, resolution step. This involved (i) Grignard reaction of cyclopentylmagnesium bromide with benzoylformic acid in anhydrous ether to give the racemic cyclopentylmandelic acid 1; (ii) methylation of 1 with methyl iodide and potassium carbonate in DMF at room temperature to yield methyl cyclopentylmandelate 2; (iii) transesterification of 2 with 1-methyl-3-pyrrolidinol 3 in heptane to give N-methyl-3-pyrrolidinyl cyclopentylmandelate 4; and (iv) quaternization of 4 with alkyl bromoacetate in acetonitrile to give the final product 5 [Compound (a) or Compound (b)]. These are racemic soft glycopyrrolate derivatives, and they have been characterized by NMR and elemental analysis.

with sodium hydroxide solution followed by acidification with hydrochloric acid. The obtained left rotatory)(−22.5° optically pure R(−)1 was characterized by NMR. Grover and coworkers reported the highly stereoselective synthesis of S)-cyclopentyl-phenylglycoxilic acid using (S)-mandelic acid in 2000, and they found (S)-cyclopentyl-phenylglycoxilic acid to have positive optical rotation, Accordingly, R(−)1, which was found to have an optical rotation of $[\alpha]=-22.5°$, is the R form. The NMR of the salt formed by the resolved cyclopentylmandelic acid R(−)1 and (+)-α-phenylethylamine gave a single pentaplet for the CHC(OH) group; whereas the salt of the unresolved 1 and (+)-α-phenylethylamine gave two pentaplets for CHC(OH).

The soft glycopyrrolate Compounds (c) and (d) having 2R configurations have been synthesized from R(−)cyclopentylmandelic acid R(−)1 by the route shown in Scheme 1, and they were also characterized by NMR and elemental analysis. The optical rotations of Compound (c) and Compound (d) were +0.5° and +5.6°, respectively.

Scheme 1

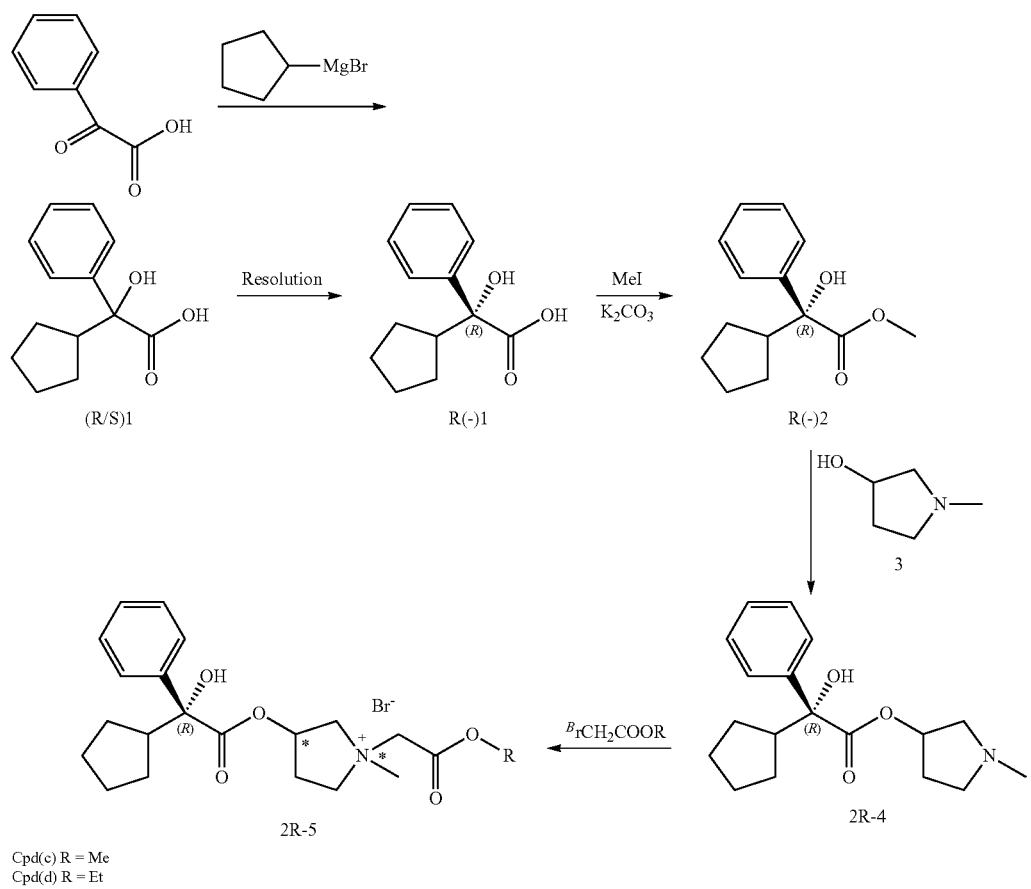

Because stereospecificity is known to be important at muscarinic receptors, improved anticholinergic activity being obtained with the 2R configuration of glycopyrrolate-type substances, these soft drug candidates have also been prepared starting with optically pure cyclopentylmandelic acid, R(−)1. Racemic 1 was resolved by repeated crystallization of the salts produced between acid 1 and (−)-strychnine. Optically pure free acid was recovered by basification of the salts The racemic Compound (a) and Compound (b) had much simpler NMR spectra than the corresponding resolved compounds, Compound (c) and Compound (d). These molecules have a total of three chiral centers as shown in Scheme 1. In Compound (c) and Compound (d), one of the chiral centers was resolved, but two others remained; hence, they both are mixture of four diastereoisomers complicating their NMR spectra. For example, the $CH_3CH_2$ methyl group showed only one triplet at 1.35 ppm in Compound (b), where it is not subject to unequal chemical environments; however, it showed four triplets at 1.26, 1.28, 1.32, and 1.35 ppm, respectively in Compound (d), which has one resolved and two unresolved chiral centers and is a mixture of four diastereoisomers (RPR, RSR, RRS, RSS). Also, the AB system of Compound (b)'s $CH_2CO_2$ group showed one set of double-doublet signals at 4.67 and 4.83 ppm, but the same system in Compound (d) showed four sets of double-doublet signals at 4.61, 4.69; 4.76, 4.85; 5.17, 5.22; and 5.26, 5.30 ppm.

pH Profile

Figure 2:
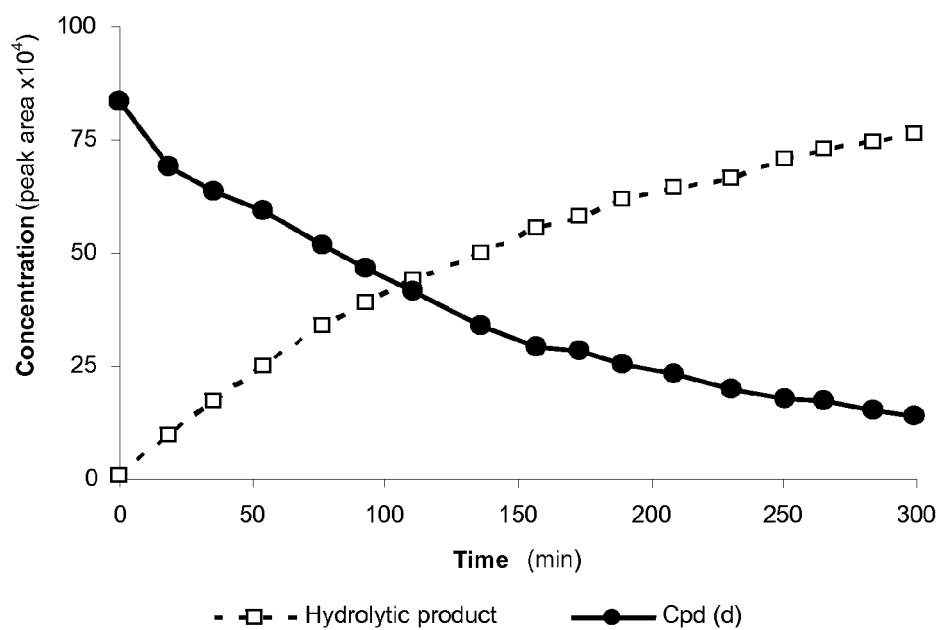
FIG. 2 is a representative time-profile of a chemical hydrolysis with formation of the corresponding acid as hydrolytic product [Compound (d), pH 7.3, 37° C.].

In the pH range of 6.00-8.40 and at 37° C., the chemical hydrolysis of the present soft glycopyrrolate compounds was significantly pH-dependent. As shown in FIG. 1, they are more stable under acidic condition, and the ethyl derivatives are more stable than the corresponding methyl derivatives. The half-lives of Compounds (a), (c), (b) and (d) in aqueous solutions at pH 6.0 were 91, 77, 155, and 134 h, respectively. However, at pH 8.4, the corresponding half-lives decreased to 8, 7, 16, and 12 min, respectively. The pH profiles are displayed in FIG. 1, and the results indicate a base-catalyzed hydrolysis of the compounds with a correlation coefficient of 0997-0.998. For illustrative purposes, the time-profile of the disappearance of Compound (c) and the concurrent formation of the corresponding acid at pH 7.4 is shown in FIG. 2.

In Vitro Stability

In vitro stability studies have been performed using rat blood and plasma by measuring the pseudo-first-order rate constant (k, min$^{-1}$) and half-life ($t_{1/2}$, min) of the disappearance of the parent compounds (Table 1). At 37'C and pH 7.4, the hydrolysis of soil glycopyrrolate analogs was relatively fast in plasma with half-lives of 19.5, 20, 44, and 34 min for Compounds (a), (c), (b) and (d), respectively, and significantly slower in blood (57, 57, 97, and 86 min, respectively; p<0.05 for all compounds, t-test or nonparametric Mann-Whitney U test), indicating that blood cell binding is significant enough to slow the hydrolytic degradation of these esters. The ethyl esters were more stable than the methyl derivatives (p<0.05, t-test or nonparametric Mann-Whitney U test).

TABLE 1

Pseudo-first-order rate constant (k, min$^{-1}$) and half-life ($t_{1/2}$, min) for the disappearance of soft analogs in rat plasma and blood. Data represent mean ± SD of three experiments.

| Compound | Medium | k × 10$^{-3}$, min$^{-1}$ | $t_{1/2}$, min | r$^2$ |
|---|---|---|---|---|
| (a) | plasma | 36.4 ± 5.0 | 19.5 ± 2.7 | 0.998 |
|     | blood  | 12.3 ± 1.3 | 57.0 ± 5.8 | 0.998 |
| (b) | plasma | 15.8 ± 0.2 | 44.0 ± 0.4 | 0.997 |
|     | blood  | 7.2 ± 0.2  | 96.6 ± 2.9 | 0.996 |
| (c) | plasma | 34.5 ± 3.2 | 20.0 ± 2.1 | 0.993 |
|     | blood  | 12.4 ± 1.4 | 56.7 ± 6.1 | 0.997 |
| (d) | plasma | 20.9 ± 3.0 | 33.8 ± 4.8 | 0.998 |
|     | blood  | 8.0 ± 0.1  | 86.4 ± 1.2 | 0.998 |

In vitro Pharmacodynamic Evaluation

To evaluate the relative potency of the newly synthesized soft analogs, receptor binding affinities, $pK_i$, and guinea pig ileum contraction ability, $pA_2$, were determined.

Receptor Binding Studies

The receptor binding affinities of the compounds determined by radioligand binding assays using human cloned muscarinic receptor subtypes, $M_1$-$M_4$, are presented in Table 2. The 2R isomers, Compounds (c) and (d), had $pK_i$ values that are in the 8.7-9.5 range; somewhat less, but close to those observed for the known highly active antagonists that served as lead for the present design, N-methylscopolamine and glycopyrrolate (9.2-9.9 and 8.7-9.9, respectively). As expected, the racemic forms, Compounds (a) and (b), showed lower receptor binding affinities than their corresponding 2R isomers (differences significant at p<0.05 level for $M_3$, t-test or nonparametric Mann-Whitney U test), confirming that stereospecificity is important at these receptors.

TABLE 2

Receptor binding affinities and $pA_2$ values.

| Compound | Subtypes of cloned muscarinic receptors [a] | | | | $pA_2$ [b] |
| | $M_1$ | $M_2$ | $M_3$ | $M_4$ | |
|---|---|---|---|---|---|
| (c) | 8.89 ± 0.04 | 8.87 ± 0.05 | 9.00 ± 0.06 | 9.52 ± 0.01 | 8.31 ± 0.05 |
|     | (0.83 ± 0.11) | (1.10 ± 0.11) | (0.83 ± 0.01) | (0.83 ± 0.01) | |
| (a) | 7.91 ± 0.05 | 7.79 ± 0.11 | 7.80 ± 0.10 | 8.29 ± 0.19 | 7.90 ± 0.13 |
|     | (1.02 ± 0.12) | (1.25 ± 0.01) | (1.17 ± 0.18) | (1.12 ± 0.05) | |
| (d) | 8.67 ± 0.16 | 8.84 ± 0.34 | 8.74 ± 0.02 | 8.85 ± 0.13 | 8.55 ± 0.16 |
|     | (0.86 ± 0.08) | (0.92 ± 0.01) | (1.09 ± 0.15) | (0.89 ± 0.02) | |
| (b) | 7.51 ± 0.17 | 7.32 ± 0.07 | 7.54 ± 0.15 | 7.94 ± 0.09 | 7.36 ± 0.34 |
|     | (0.91 ± 0.09) | (1.23 ± 0.06) | (1.18 ± 0.08) | (1.18 ± 0.09) | |
| glycopyrrolate | 9.76 ± 0.05 | 9.19 ± 0.18 | 8.73 ± 0.05 | 9.90 ± 0.08 | 8.57 ± 0.12 |
|     | (1.37 ± 0.20) | (0.99 ± 0.11) | (1.14 ± 0.25) | (1.02 ± 0.01) | |
| scopolamine methyl bromide | 9.69 ± 0.01 | 9.18 ± 0.21 | 9.29 ± 0.12 | 9.92 ± 0.21 | 9.16 ± 0.19 |
|     | (0.92 ± 0.10) | (1.02 ± 0.02) | (1.07 ± 0.01) | (0.90 ± 0.04) | |

[a] Data of the receptor binding experiments represent mean ± S.D. of 3 experiments. The numbers in parentheses denote Hill slopes.
[b] $pA_2$ values were determined on 4-6 ileum strips obtained from different animals. Data represent mean ± SD.

$pA_2$ Studies

The $pA_2$ values determined from guinea pig ileum contraction assays, which represent the negative logarithm of the molar concentration of the antagonist that produces a two-fold shift to the right in an agonist's concentration-response curve, are a classical functional study of anticholinergic affinity (at $M_3$ muscarinic receptors). For the soft anticholinergics of the present study, the $pA_2$ values obtained from ileum longitudinal contractions by using carbachol as agonists with the method of van Rossum (Table 2) were, in general, comparable to the $pK_i$ values obtained in the $M_3$ receptor binding studies. The 2R isomers were again significantly more active than the corresponding racemates, and the most active soft analog [Compound (d), $pA_2=8.55_{\pm 0.16}$] showed activity similar to glycopyrrolate ($pA_2=8.57_{\pm 0.12}$).

Mydriatic Activities of Soft Analogs

Figure 3:
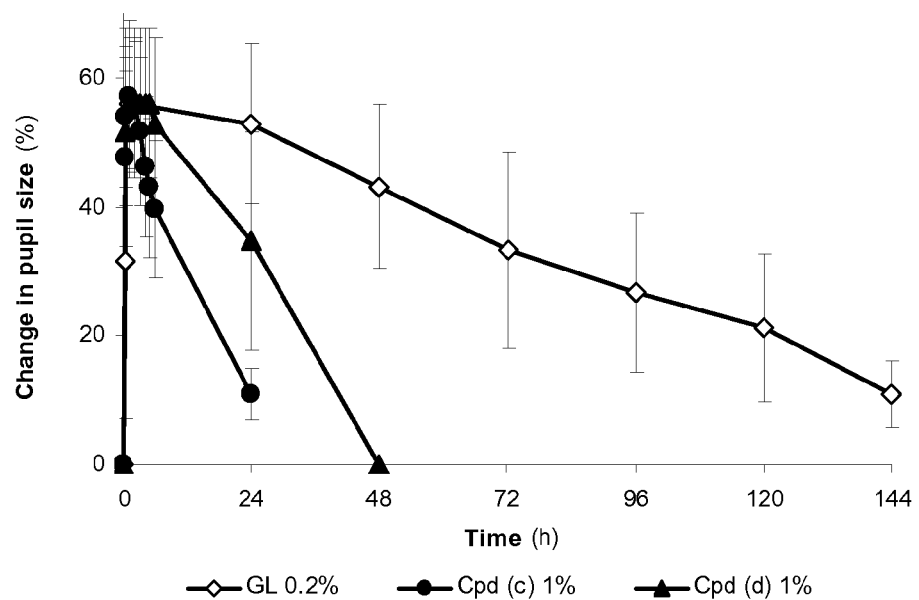
FIG. 3A is a graph of mydriatic activities of glycopyrrolate and soft analogs Compound (c) and Compound (d) at pharmacologically equipotent doses (mean±SD shown) showing data for up to 144 hours.
FIG. 3B is a graph of mydriatic activities of glycopyrrolate and soft analogs Compounds (c) and (d) at pharmacologically equipotent doses (mean±SD shown) showing data for the first 24 hours only.
Figure 3:
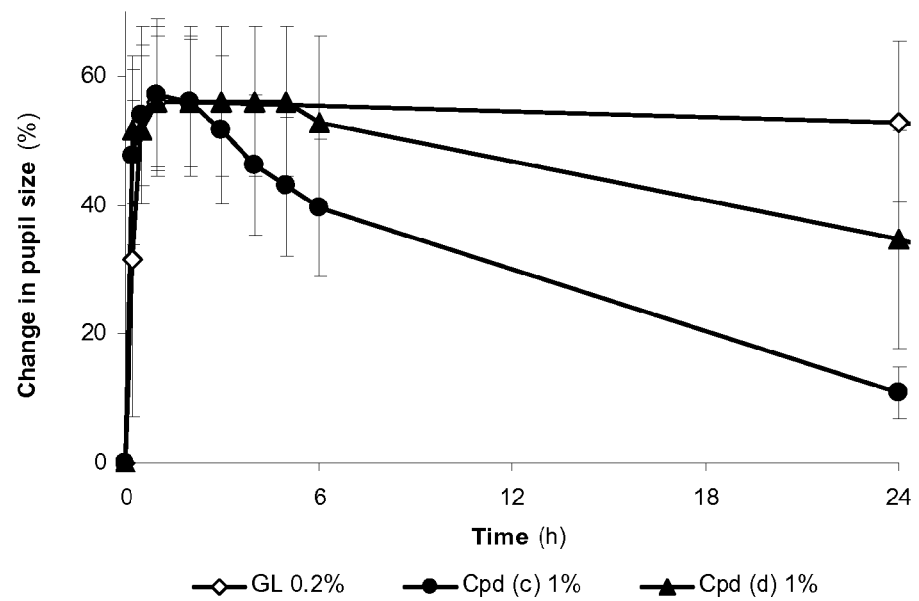

The mydriatic effects of the new soft derivatives. Compounds (a) and (b), were compared to those of glycopyrrolate in rabbits. Mydriatic responses were recorded at appropriate time-intervals after the administration of the drugs as % changes in pupil size. Maximum response ($R_{max}$, % change in pupil size at 1 h after administration) and area under the response-time curve ($AUC^{eff}$) are shown in Table 3. Whereas, there are no significant differences among the $R_{max}$ maximum responses among all treatments considered (compounds and concentrations of Table 3), there dearly are among the $AUC^{eff}$s ($p<0.05$, ANOVA followed by Tukey-Kramer multiple comparison test). Glycopyrrolate (0.1%, 0.2%) gave significantly longer-lasting effects (larger $AUC^{eff}$s) than any of the soft drugs. The soft ethyl compounds seem somewhat more potent than corresponding methyl analogs, and the 2R isomers seem more potent than the isomeric mixtures, In agreement with soft drug design principles, their duration of action is much shorter than that of the "hard" glycopyrrolate as illustrated in FIG. 3A and FIG. 3B for pharmacodynamically equipotent doses. The mydriatic activity of Compound (c), Compound (d), and glycopyrrolate lasted for 24, <48, and 144 h, respectively, indicating that the soft drugs are easily hydrolyzed and rapidly eliminated from the body after the desired pharmacological effect is achieved. In agreement with this and unlike other traditional anticholinergics, these soft drugs did not induce dilation of the pupil in the contralateral (water-treated) eye, indicating no or just low systemic side-effects. Therefore, these compounds are safe, promising short acting anticholinergics with the possibility of largely reduced unwanted side effects.

TABLE 3

Maximum response ($R_{max}$, % change in pupil size at 1 h after administration) and area under the response-time curve ($AUC^{eff}$). Data indicate mean ± SD of four trials.

| Compound | Conc. (%) | $R_{max}$ (%) | $AUC^{eff}_{(0-144\,h)}$ |
|---|---|---|---|
| (a) | 0.5 | 45.83 ± 4.81 | 185 ± 35 |
|  | 1 | 59.58 ± 15.72 | 467 ± 114 |
| (b) | 0.5 | 44.65 ± 13.99 | 596 ± 274 |
|  | 1 | 58.33 ± 12.27 | 645 ± 409 |
| (c) | 0.5 | 52.92 ± 13.41 | 752 ± 342 |
|  | 1 | 57.08 ± 11.66 | 875 ± 197 |
| (d) | 0.5 | 53.96 ± 13.27 | 1170 ± 308 |
|  | 1 | 56.04 ± 11.69 | 1532 ± 526 |
| glycopyrrolate | 0.05 | 51.46 ± 7.71 | 2779 ± 443 |
|  | 0.1 | 55.83 ± 6.42 | 4074 ± 459 |
|  | 0.2 | 56.04 ± 10.10 | 5047 ± 1631 |

In conclusion, a set of new glycopyrrolate-based soft anticholinergics has been designed, synthesized, and tested. They were found to have receptor binding affinities comparable to those of glycopyrrolate or N-methylscopolamine, and good, but short-lasting mydriatic activity with no or just minimal systemic effects due to their soft nature that allows easy, one-step metabolism into a designed-in metabolite after exerting their desired pharmacological activity.

Further Studies

Purpose. Because stereospecificity is known to be important at muscarinic receptors, isomers of both N-substituted soft anticholinergics based on glycopyrrolate, (2R) 3-(2-cyclopentyl-2-phenyl-2-hydroxyacetoxy)-1-(alkoxycarbonylmethyl)-1-methylpyrrolidinium bromide methyl and ethyl esters, Compounds (c) and (d), and their zwitterionic metabolite, (2R) 3-(2-cyclopentyl-2-phenyl-2-hydroxyacetoxy)-1-methyl-1-carboxymethylpyrrolidinium inner salt, were synthesized and their pharmacological activities were evaluated in vitro and in vivo.

Methods. The isomers of Compounds (c) and (d) were synthesized with both optically pure methyl-cyclopentyl-mandelate and 3-hydroxy-N-methylpyrrolidine. Trans-esterification followed by quarternization with alkyl bromoacetate gave four isomers of the methyl or ethyl ester with the nitrogen chiral center unresolved. The hydrolysis of these four isomers followed by HPLC separation resulted in eight fully resolved isomers of the corresponding acid. The pharmacological activities were assessed using the in vitro receptor-binding assay, guinea pig ileum $pA_2$-assay, and in vivo rabbit mydriatic effect. The results were compared with that of conventional anticholinergic agents such as glycopyrrolate, N-meythylscopolamine, and tropicamide as well as that of previously prepared racemates and 2R isomers.

Results. The receptor binding at cloned human muscarinic receptors ($M_1$-$M_4$ subtypes), $pK_i$ values, of these newly synthesized methyl and ethyl ester isomers were in the 6.0-9.5 range, and zwitterion isomers in 5.0-8.6 range. In both cases. 2R isomers were found significantly more active than 2S isomers (27-447 times for methyl ester isomers, and 6 to 4467 times for zwitterion isomers). Among four isomers of the methyl ester Compound (c) (with chiral center 1' unresolved), the 3'R isomers were more active than the corresponding 3'S isomers (1.5-12.9 times). However, in the case of zwitterion isomers, the 3'S isomers were not always more active than the corresponding 3'R isomers, indicating that activity determined based on chiral center 3' is significantly affected by the configuration of other two chiral centers, 2 and 1'. In the completely resolved 8 zwitterion isomers (all the three chiral centers resolved), it was found that 1'S isomers were more active than the corresponding 1'R isomers in all cases (1.8-22.4 times). The results also indicate that some isomers showed good $M_3/M_2$ muscarinic-receptor subtype-selectivities (about 3-5 times), and 2R and 3'S were the determining configurations for this property. Guinea pig ileum assays and rabbit mydriasis test on zwitterion isomers double confirmed the stereospecificity. In rabbit eyes, some 2R-zwitterion isomers showed mydriatic potencies similar to glycopyrrolate and exceeded tropicamide, but their mydriatic effects lasted considerably less time, and they did not induce dilation of the pupil in the contralateral, water-treated eyes. These results indicate that, in agreement with their soft nature, they are locally active, but safe and have a low potential to cause systemic side effects. The pharmacological potency of eight zwitterion isomers was concluded to be (2R1'S3'S, 2R1'S3'R and 2R1'R3'S)>2R1'R3'R>2S1S3'R>(2S1'S3'S and 2S1'R3'R)>2S1'R3'S.

Conclusions. The stereospecificity and $M_3 1 M_2$ muscarinic-receptor subtype-selectivity of soft anti-cholinergics, Compounds (c) and (d) and their zwitterionic metabolite, have been demonstrated. Adding to the previous results, safe use of these soft drugs has been confirmed.

Introduction

Stereospecificity of anticholinergics is important at muscarinic receptors, Compounds (c) and (d), (2R) 3-(2-cyclopentyl-2-phenyl-2-hydroxyacetoxy)-1-(alkoxycarbonylmethyl)-1-methylpyrrolidinium bromide, and their common zwitterionic metabolite, (2R) 3-(2-cyclopentyl-2-phenyl-2-hydroxyacetoxy)-1-methyl-1-carboxymethylpyrrolidinium inner salt, have shown promising activity and safety in animal studies. These compounds indeed exhibited stereospecificity toward muscarinic receptors, and the anticholinergic activity has been improved with the 2R configuration. In addition, the zwitterionic metabolite also showed a moderate $M_3/M_2$ muscarinic-receptor subtype-selectivity that indicates a reduced systemic cardiac side effect. However, the molecules of this type of soft analogs possess three chiral centers, so that each racemic compound may contains up to eight different isomers, that is 2R1'R3'R, 2R1'R3'S, 2R1'S3'R, 2R1'S3'S, 2S1'R3'R, 2S1'R3'S, 2S1'S3'R, and 2S1'S3'S as displayed below:

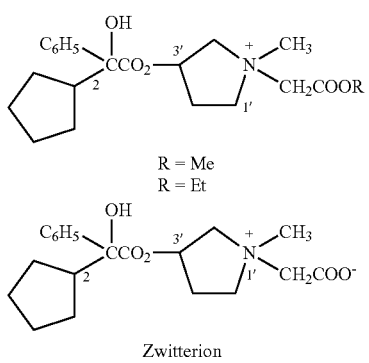

Zwitterion

Thus, the above-described investigations in the soft glycopyrrolate isomers based on one resolved chiral center (2R or 2S) only expressed that 2R enantiomers (a mixture of four diastereoisomers 2R1'3'R, 2R1'R3'S, 2R1'S3'R, 2R1'S3'S) were more active than 2S enantiomers (a mixture of 2S1'R3'R, 2S1'R3'S, 2S1'S3'R, 2S1'S3'S). In this section, further investigations in the stereospecificity of these soft glycopyrrolates are reported using five partially-resolved soft anticholinergics isomers and eight fully resolved zwitterion metabolite, isomers (as described for 2R and 2S enantiomers). The compounds were systematically synthesized and isomers were separated. The relative pharmacological activities and $M_3/M_2$ muscarinic-receptor subtype-selectivities were investigated by in vitro receptor-binding assay, in vitro guinea pig ileum $pA_2$-assay, and in vivo mydriatic effect in rabbits.

Materials and Methods

Materials

Glycopyrrolate (glycopyrronium bromide) was kindly provided by Boehringer Ingelheim Chemicals, Inc. Carbamylcholine bromide (carbachol), atropine methylbromide (atropine MeBr), and scopolamine methylbromide (scopolamine MeBr) were obtained from Sigma Chemicals Co. (St. Louis, Mo.), and tropicamide (1%) was obtained from Bausch & Lomb Pharmaceutical (Tampa, Fla.). N-[$^3$H]-Methyl-scopolamine (NMS) was obtained from Amersham Biosciences UK Limited (Buckinghamshire, UK). Cloned human muscarinic receptor subtypes $M_1$-$M_4$ were obtained from Applied Cell Science Inc. (Rockville, Md.). Scintiverse BD was from Fisher Scientific Co, (Pittsburgh, Pa.), (R)-3-hydroxy pyrrolidine hydrochloride and (S)-3-hydroxy pyrrolidine hydrochloride were from Astatech Inc. (Monmouth Junction. NJ), N-[$^3$H]-Methyl-scopolamine (NMS) was from Amersham Biosciences UK Limited (Buckinghamshire, UK). Cloned human muscarinic receptor subtypes $M_1$-$M_4$ were from Applied Cell Science Inc, (Rockville, Md.). Scintiverse BD was from Fisher Scientific Co. (Pittsburgh, Pa.). Other chemicals used for synthesis were reagent or HPLC grade, and were obtained from Aldrich (Milwaukee, Wis.) and Fisher Scientific Co. Melting points were taken on Fisher-Johns melting apparatus. NMR spectra were recorded on Bruker Advance 300, 400 and 500 MHz NMR spectrometers, and are reported in ppm relative to TMS. NOESY was performed using 2D NMR spectrometer, Mercury-300BB, Animal studies were performed in accordance with the Guide for the Care and Use of Laboratory Animals adopted by the National Institute of Health, USA. Institutional animal care and use committee (IACUC) approval was obtained prior to the initiation of this research and during its execution.

Synthesis of 2R-Isomers

Racemic Cyclopentylmandelic Acid, 1

Cyclopentylmagnesium bromide ether solution (100 ml, 2M; 0.2 mol) was added drop-wise to benzoylformic acid (15 g, 0.1 mol) in 330 ml of anhydrous ethyl ether at 0° C. The mixture was stirred at 0° C. for 30 min and at room temperature for 24 h. The reaction mixture was treated with 1 N HCl, and the aqueous solution was extracted with ether. The combined ether solution was treated with $K_2CO_3$ solution. The potassium carbonate solution was acidified with HCl and extracted with ether twice. The ether solution was dried with anhydrous sodium sulfate and evaporated to give a crude product. The crude product was washed with water to get pure racemic cyclopentylmandelic acid 1 (8.0 g, 36.4%). Needle-like crystal, m.p.: 153-154° C. $^1$H NMR ($CDCl_3$, 300 MHz): 1.28-1.39, 1.42-1.50, 1.51-1.61, 1.63-1.72 [8H, m, $(CH_2)_4$], 2.93 [1H, p, CHC(OH)], 7.26-7.30, 7.33-7.36, 7.65-7.67 (5H, m, Ph) ppm.

Resolution of Racemic Cyclopentylmandelic Acid, R(−)1

(−)-Strychnine (11.4 g) in 100 ml of methanol (suspension) was added to racemic cyclopentylmandelic acid 1 (7.5 g) in methanol (20 ml) at room temperature. The reaction solution was allowed to stand overnight. The crystals were filtered and crystallized again with hot methanol. The second crop of crystals was collected by filtration and treated with sodium hydroxide solution. The basic solution was extracted with methylene chloride twice (methylene chloride solution discarded), and then acidified with hydrochloric acid to recover the resolved cyclopentylmandelic acid. To this resolved acid (20.6 mg in 0.1 ml of ethyl acetate), 13 µL of (+)-α-phenyl-ethylamine was added. The precipitate which formed was washed with hexane three times and dried under vacuum. The precipitate was identified by NMR as optically pure cyclopentylmandelic acid, R(−)1, (2.5 g, 33.3%). M.p.: 121-122° C. $[\alpha]^{25}_D$=−22.5° (c=1 g/100 ml, $CHCl_3$). $^1$H NMR($CDCl_3$, 300 MHz): 1.28-1.39, 1.42-1.50, 1.51-1.61, 1.64-1.73 [8H, m, $(CH_2)_4$], 2.93 [1H, p, CHC(OH)], 7.25-7.28, 7.32-7.35, 7.64-7.65 (5H, m, Ph) ppm.

Methyl (−)-cyclopentylmandelate, R(−)2

To a mixture of (−)-cyclopentylmandelic acid, R(−)1, (1.83 g, 8.3 mmol) and potassium carbonate (2.87 g, 21 mmol) in DMF (21 ml), methyl iodide (3.53 g, 25 mmol) was added at room temperature. The mixture was stirred at room temperature for 2 h, and then poured into water and extracted with hexane three times. Evaporation of dried hexane extract gave a crude product. Flash chromatography of the crude product on silica gel with 1.5:1 hexane:methylene chloride gave pure product R(−)2 (1.90 g, 95%), $^1$H NMR ($CDCl_3$, 300 MHz):

1.32-1.36, 1.43-1.61 [8H, m, (CH$_2$)$_4$], 2.90 [1H, p, CHC(OH)], 3.71 (1H, s, OH), 3.79 (3H, s, CH$_3$), 7.25-7.28, 7.31-7.35, 7.63-7.65 (5H, m, Ph) ppm.

(R)-3-Hydroxy-N-Methyl pyrrolidine, (R)3

In a 100 ml flask, 2 g (R)-3-Hydroxy pyrrolidine, 25 ml THE, 0.49 g paraformaldehyde and 1.5 g formic acid (90%) were added. The mixture was stirred under reflux for 5 hours (until all solid disappeared), then cooled at 0° C. and added with 10 nil of NaOH solution (10 N) to adjust the pH to about 10. The organic layer was separated and dried over MgSO$_4$. After filtering the dried solution and removing the solvent (THF), an oily product (1.5 g, 92%) of (R)3 was obtained. $^1$H NMR (CDCl$_3$, 300 MHz): 1.50-1.60 (m, 1H), 1.98-2.10 (m, 1H), 2.25 (s, 3H), 2.25-2.40 (m, 2H), 2.50-2.60 (m, 1H), 2.61-2.70 (m, 1H), 3.80 (brs, 1H), 4.20-4.30 (m, 1H).

(S)-3-Hydroxy-N-Methyl pyrrolidine, (S)3

Synthesis of (S)3 was the same as for (R)3, except that the starting material was (S)-Hydroxy pyrrolidine. The resultant product (S)3 (1.5 g, 92%) was also an oil. $^1$H NMR (DMSO-D6 300 MHz): 1.50-1.60 (m, 1H), 1.98-2.05 (m, 1H), 2.15 (s, 3H), 2.15-2.35 (m, 2H), 2.45-2.52 (m, 1H), 2.61-2.70 (m, 1H), 4.20 (brs, 1H), 4.60-4.70 (m, 1H).

3(R)—N-Methyl-3-pyrrolidinyl-2(R)-cyclopentyl-mandelate, 4

A solution of R(−)2 (0.7 g, 3 mmol) and (R)3 (0.7 g, 7 mmol) in 40 nil of toluene was heated until 20 ml of toluene had distilled, Approximately 0.003 g of sodium was added, and the solution was stirred and heated for 2 h as the distillation was continued. More toluene was added at such a rate as to keep the reaction volume constant. Additional sodium was added at the end of an hour. The solution was then cooled and extracted with 3N HCl. The acid extract was made alkaline with concentrated NaOH and extracted three times with ether. Removal of dried ether solution gave a crude oil. Flash chromatography of the crude product on silica gel with 8:1 of EtOAc and EtOH gave an oil product of 4 (0.4 g, 44%). $^1$H NMR (CDCl$_3$, 300 MHz): 1.28-1.37, 1.51-1.70, 1.83-1.90 [8H, m, (CH$_2$)$_4$], 2.27-2.40 (m, 3H), 2.52-2.55 (m, 1H), 2.64-2.72 (m, 1H), 2.74-2.81 (m, 1H), 2.33 (3H, s, NCH$_3$), 2.93 [1H, p, CHC(OH)], 3.85 (1H, bs, OH), 5.22 (m, 1H), 7.24-7.27, 7.31-7.35, 7.64-7.66 (5H, m, Ph) ppm.

3(S)—N-Methyl-3-pyrrolidinyl-2(R)-cyclopentyl-mandelate, 5

Synthesis of 5 was the same as for 4, except (S)3 was used instead of (R)3. The resultant product 5 (0.35 g, 39%) was also an oil. NMR (CDCl$_3$, 400 MHz): 1.28-1.37, 1.51-1.70, 1.75-1.82[8H, m, (CH$_2$)4], 2.15-2.22 (m, 1H), 2.30-2.40 (m, 2H), 2.65-2.70 (m, 1H), 2.70-2.82 (m, 2H, 2.35 (3H, s, NCH$_3$), 2.95 [1H, p, CHC(OH)], 3.82 (1H, bs, OH), 5.22 (m, 1H), 7.24-7.27, 7.31-7.35, 7.64-7.66 (5H, m, Ph) ppm.

(2R,3'R) 3-(2-Cyclopentyl-2-phenyl-2-hydroxyacetoxy)-1-(methoxycarbonylmethyl)-1-methylpyrrolidinium bromide, 6 [Compound (e)]

To Compound 4 (0.3 g, 0.98 mmol) in 12 ml of dry acetonitrile, methyl bromoacetate (0.5 g, 3.2 mmol) was added at room temperature. The mixture was stirred for 6 h. Evaporation of acetonitrile gave a crude product. The crude product was dissolved in a small volume of methylene chloride and then poured into 50 ml of dry ethyl ether to precipitate. This step was repeated three times to obtain the pure product 6, or Compound (e), (0.3 g, 70%) as a white powder that was a mixture of two diastereoisomers in a NMR-estimated ratio of 2:1, $^1$H NMR (CDCl$_3$, 400 MHz): 1.30-1.37, 1.41-1.50, 1.55-1.70 [8H, m, (CH$_2$)$_4$], 2.10-2.27 (m, 1H), 2.79-195 (m, 2H), 3.05, 3.60 (2s, total 3H, N—CH3), 3.75, 3.79 (2s, total 3H, O-Me), 3.95-4.40 (m, 4H), 4.68, 5.16 (2AB, total 2H, N—CH2-COOMe), 5.52-5.58 (m, 1H), 7.23-7.29, 7.31-7.38, 7.56-7.60 (5H, m, Ph) ppm,

(2R,3'S) 3-(2-Cyclopentyl-2-phenyl-2-hydroxyacetoxy)-1-(methoxycarbonylmethyl)-1-methylpyrrolidinium bromide, 7a [Compound (f)]

To Compound 5 (0.16 g, 0.52 mmol) in 8 ml of thy acetonitrile, methyl bromoacetate (0.3 g, 1.9 mmol) was added at room temperature. Following the same procedure for 6 [Compound (e)] the pure product 7a [Compound (f)] (0.16 g, 80%) was obtained. Compound (f) was also a white powder and a mixture of two diastereoisomers in a NMR-estimated ratio of 2:1. $^1$H NMR (CDCl$_3$, 400 MHz): 1.30-1.70 [8H, m, (CH$_2$)$_4$], 1.95-2.00, 2.10-2.20 (m, 1H), 2.75-2.95 (m, 2H), 3.30, 3.70 (2s, total 3H, N—CH3), 3.78, 3.82 (2s, total 3H, 0-Me), 4.00-4.42 (m, 4H), 4.90, 5.38 (2AB, total 2H, N—CH2-COOMe), 5.52-5.58 (m, 1H), 7.23-7.29, 7.31-7.38, 7.56-7.60 (5H, m, Ph) ppm.

(2R,3'S) 3-(2-Cyclopentyl-2-phenyl-2-hydroxyacetoxy)-1-(ethoxycarbonylmethyl)-1-methylpyrrolidinium bromide, 7b [Compound (g)]

To Compound 5 (0.16 g, 0.52 mmol) in 10 nil of dry acetonitrile, ethyl bromoacetate (0.32 g, 1.9 mmol) was added at room temperature. The mixture was stirred for 22 hours, and the removal of acetonitrile gave a crude product. The crude product was dissolved in small volume of ethylene chloride, and then poured into a 50 ml of dry ethyl ether to afford a precipitate. This procedure was repeated three times, and the pure product 7b, or Compound (g) (0.16 g, 80%) was obtained. Compound (g) was also a white powder and a mixture of two diastereoisomers in a NMR-estimated ratio of 2:1. $^1$H NMR (CDCl$_3$, 400 MHz): 1.32, 1.35 (2t, 3H, CH$_3$CH$_2$), 1.40-1.50, 1.53-1.63, 1.65-1.80 [8H, m, (CH$_2$)$_4$], 1.93-2.11 (m 2H), 2.80-2.96 M, 2H), 3.30, 3.70 (2s, 3H, N—CH3), 4.10-4.60 (m, 6H), 4.79, 5.30 (2H, 2 set of dd, CH$_2$CO$_2$), 5.53 (1H, m), 7.24-7.29, 7.31-7.38, 7.56-7.60 (5H, m, Ph) ppm.

Hydrolysis of Esters

Compounds (e) and (f) were combined with equimolar ratios of 0.1 N NaOH. The mixtures were stirred at room temperature for 3 hours to obtain the corresponding racemic zwitterionic products, 8 and 9 in aqueous solution (colorless, pH about 6.5). Compound 8 is (2R,3'R) 3-(2-cyclopentyl-2-phenyl-2-hydroxyacetoxy)-1-(carboxymethyl)-1-methylpyrrolidinium inner salt. Compound 9 is (2R,3'S) 3-(2-cyclopentyl-2-phenyl-2-hydroxyacetoxy)-1-(carboxymethyl)-1-methylpyrrolidinium inner salt.

HPLC Separations for 8a, 8b, and 9a, 9b

The solutions of 8 and 9 each contained two isomers, 8a, 8b and 9a, 9b, at a ratio of 2:1 that could be separated by HPLC. The HPLC system consisted of a Spectra Physics (San Jose, Calif.) SP 8810 isocratic pump, a SP 8450 UV/Vis detector (wavelength set to 230 nm), a SP 4290 integrator, and a Supelco Discovery RP Amide C16 column. The mobile phase consisted of acetonitrile and water at a ratio of 30:70. With 100 µl injection at a flow rate of 1 ml/min, the retention times were 7.2 min for 8a and 9a, and 8.5 min for 8b and 9b. The effluence corresponding to each isomer was collected, and the solvent was evaporated to obtain the final zwitterionic isomers, 8a, 8b, and 9a, 9b as following:

(2R,1'R,3'R) 3-(2-cyclopentyl-2-phenyl-2-hydroxy-acetoxy)-1-(carboxymethyl)-1-methylpyrrolidinium inner salt, 8a white powder $^1$H NMR (CDCl$_3$, 300 MHz):1.30-1.65 (m, 8H), 2.02-2.12 (m, 1H), 2.20-2.60 (brs, 1H), 2.60-2.80 (m, 1H), 2.82-2.92 (m, 1H), 3.30 (s, 3H), 3.55-3.65 (m, 1H), 3.72-3.82 (m, 1H), 3.90-4.05 (m, 2H), 4.10-4.15 (m, 1H), 5.38-5.45 (m, 1H), 7.15-7.20 (m, 1H), 7.32-7.38 (m, 2H), 7.55-7.62 (m, 2H).

(2R,1'R,3'S) 3-(2-cyclopentyl-2-phenyl-2-hydroxy-acetoxy)-1-(carboxymethyl)-1-methylpyrrolidinium inner salt, 8b $^1$H NMR (CDCl$_3$, 300 MHz):1.30-1.75 (m, 8H), 2.02-2.10 (m, 1H), 2.10-2.40 (brs, 2H), 2.70-2.80 (m, 1H), 2.80-2.90 (m, 1H), 2.95 (s, 3H), 3.55-3.65 (m, 2H), 3.85-4.0 (m, 3H), 4.05-4.10 (m, 1H), 5.38-5.45 (m, 1H), 7.15-7.20 (m, 1H), 7.25-7.30 (m, 2H), 7.50-7.60 (m, 2H).

(2R,1'R,3'S) 3-(2-cyclopentyl-2-phenyl-2-hydroxy-acetoxy)-1-(carboxymethyl-1-methylpyrrolidinium inner salt, 9a white powder, $^1$H NMR (CDCl$_3$, 500 MHz): 1.30-1.65 (n, 8H), 2.02-2.12 (m, 1H), 2.50-2.60 (m, III), 2.78-2.88 (m, 1H), 3.25 (s, 31-1), 3.65-4.05 (m, 411), 4.15-4.30 (brs, 211), 5.30-5.40 (m, 1H), 7.13-7.23 (m, 1H), 7.26-7.32 (m, 2H), 7.55-7.60 (m, 2H).

(2R,1'S,3'S) 3-(2-cyclopentyl-2-phenyl-2-hydroxyac-etoxy)-1-(carboxymethyl)-1-methylpyrrolidinium inner salt, 9b white powder, $^1$H NMR (CDCl$_3$, 500 MHz):1.30-1.70 (m, 8H), 1.90-1.98 (m, 1H), 2.65-2.70 (m, 1H), 2.85-2.90 (m, 1H), 3.15 (s, 3H), 3.65-3.90 (m, 4H), 4.05-4.10 (M, 1H), 4.15-4.22 (brs, 1H), 5.35-5.42 (m, 1H), 7.18-7.23 (m, 1H), 7.27-7.32 (m, 2H), 7.53-7.58 (m, 2H).

Determination of Absolute Configurations

Nuclear overhauser effect (NOE) has been used to identify the absolute configuration of the product 8b. Compound was dissolved in CDCl$_3$, and the 2D $^1$H—$^1$H spectrum was taken by Mercury-300BB.

Synthesis of 2S-isomers

Cis-(2S,5S)-2-(tert-butyl)-5-phenyl-1,3-dioxolan-4-one, 10

S(+)-mandelic acid in hexane suspension (50 g, 328 mmol) was added with pivaldehyde (42.7 ml, 396 mmol) then trifluoromethanesulfonic acid (1.23 ml, 14 mmol) at room temperature. The mixture was warmed to 36 and the reaction was followed by TLC for 5 hr until no starting material could be detected. The mixture was then cooled to room temperature and added with 8% aqueous NaHCO$_3$. The water layer was removed and the organic layer was dried over Na$_2$SO$_4$. After filtration and removal of the solvent, 62.17 g of the crude product was obtained. Recrystallization of the crude product gave 44.71 g of pure cis-(2S,5S)-2-(tert-butyl)-5-phenyl-1,3-dioxolan-4-one in 88% yield as a needle-like crystal. $^1$H NMR (CDCl$_3$, 300 MHz): 1.08 (s, 9H), 5.24 (s, 1H), 5.33 (s, 1H), 7.40-7.46 (m, 5H) ppm. $^{13}$C NMR (CDCl$_3$, 300 MHz): 23.6, 34.4, 77.0, 109.3, 127.0, 128.7, 129.2, 133.4, 147.2.

Cis-(2S,5S)-2-(tert-butyl)-5-phenyl-5-cyclopentyl-1,3-dioxolon-4-one, 11

At −78'C, a lithium bis-(trimethylsilyl)amide in hexane solution (120 ml, 120 mmol, 1.0M in hexane) was added to compound 10 (25 g, 113.5 mmol, dissolved in 100 ml of dried THF), stirred for 1 hr, followed by addition of cyclopentyl bromide (25 g, 168 mmol). This reaction was kept at −78° C. for 4 hr, then slowly warmed up to room temperature and continued for overnight. The completion of the reaction was followed by TLC. With stirring, a solution of 10% of NH$_4$Cl (25 ml) was added in the mixture. Then, the mixture was poured into a separation funnel containing 10% NH$_4$Cl solution (200 ml), The aqueous layer was discarded, and the organic layer was dried over Na$_2$SO$_4$. The solvent was removed to give a crude product, which was then re-crystallized in hexane to give a pure product, 11 (20.36 g, yield 63%, white crystal). $^1$H NMR (CDCl$_3$, 300 MHz): 1.15 (s, 9H), 1.55-1.95 (m, 8H), 2.74 (m, 1H), 5.62 (s, 1H), 7.44-7.56 (m, 3H), 7.88-7.91 (n, 2H) ppm. $^{13}$C NMR (CDCl$_3$, 300 MHz): 23.5, 24.5, 25.3, 26.6, 35.6, 50.9, 83.2, 110.6, 124.9, 127.5, 127.9, 138.9, 173.7.

S(+)-Cyclopentylmandelic Acid, 12

To a solution of cis-(2S,5S)-2-(tert-butyl)-5-cyclopentyl-5-phenyl-1,3-dioxolan-4-one (14.35 g, 50 mmol) in 100 ml methanol and 50 ml water, 15 g of KOH was added slowly. The mixture was stirred and heated (65° C.) to reflux for 3-4 hr, then cooled down to the room temperature, and methanol was removed. To the aqueous solution, 100 ml of ethyl acetate was added, then acidified to pH 1 with 3N HCl. The mixture was poured into a separation funnel, and the organic layer was separated. The aqueous layer was extracted two times with ethyl acetate (50 ml). The combined organic layers were dried over Na$_2$SO$_4$, filtered, and the solvent was removed to provide 13.44 g of yellowish crude product, which was re-crystallized to give a pure product of S(+)-cyclopentylmandelic acid, 12 (6.89 g, yield 62%, white crystal). $^1$H NMR (CDCl$_3$, 300 MHz): 1.28-1.75 (m, 8H), 2.94 (m, 1H), 7.24-7.34 (m, 3H), 7.62-7.68 (m, 2H). $^{13}$C NMR (CDCl$_3$, 300 MHz): 25.9, 26.3, 26.4, 26.9, 47.1, 79.2, 125.8, 127.7, 128.2, 140.8, 180.9.

Methyl S(+)-cyclopentylmandelate, 13

S(+)-cyclopentylmandelic acid, 12 (5.5 g, 25 mmol), and potassium carbonate (8.61 g, 63 mmol) in DMF (60 ml) solution was added with methyl iodide (10.6 g, 75 mmol). The mixture was stirred at room temperature for 3 hr. poured into water, and extracted with hexane for three times. Evaporation of dried hexane extract gave a pure product of S(+)-cyclopentylmandelate, 13 (5.85 g, too %, clear oil). $^1$H NMR (CDCl$_3$, 300 MHz): 1.32-1.61 [8H, m, (CH$_2$)$_4$], 2.90 [1H, p, CHC (OH)], 3.76 (s, 3H), 3.78 (s, 1H), 7.25-7.35 (m, 3H), 7.63-7.65 (m, 2H). $^{13}$C NMR (CDCl$_3$, 300 MHz): 25.9, 26.2, 26.3, 26.8, 47.1, 53.2, 79.1, 125.8, 127.3, 128.0, 141.6, 176.0.

(R)-3-Hydroxy-N-Methylpyrrolidine, (R)3

In a 100 ml flask, 4 g (R)-3-Hydroxy pyrrolidine hydrochloride salt, 50 ml THE and 1.3 g NaOH were added and stirred for 20 min. Then, 1.1 g paraformaldehyde and 4.8 g formic acid (90%) were added. The mixture was heated (60° C.) and stirred at reflux for 2 hr until all solid disappeared. The mixture was cooled to 0° C., combined with 6.5 ml of 10 N NaOH solution (pH about 10), and extracted twice by ethyl ether (50 ml). The combined organic layer was dried over $Na_2SO_4$. Evaporation of the dried organic layer gave a yellowish, oily product of (R)3 (3.0 g, 92%). $^1$H NMR ($CDCl_3$, 300 MHz): 1.65-1.75 (m, 1H), 2.15-2.36 (m, 2H), 2.33 (s, 3H), 2.55-2.59 (m, 2H), 2.76-2.85 (m, 1), 4.30-4.40 (m, 1H), 4.8-5.10 (brs, 1H). $^{13}$C NMR ($CDCl_3$, 300 MHz): 35.4, 41.9, 54.7, 64.9, 70.9.

(S)-3-Hydroxy-N-Methylpyrrolidine, (S)3

Synthesis of (S)3 was the same as for (R)3, except the starting material was (S)-3-Hydroxypyrrolidine hydrochloride salt. The resultant product (S)3 (3.10 g, 95%) was also an oil. $^1$H NMR ($CDCl_3$, 300 MHz): 1.50-1.60 (m, 1H), 2.05-2.30 On, 2H), 2.28 (s, 3H), 2.40-2.50 (m, 2H), 2.70-2.80 (m, 1H), 4.25-4.30 (m, 1H), 4.80 (brs, 1H). $^{13}$C NMR ($CDCl_3$, 300 MHz):35.4, 41.9, 54.7, 64.9, 70.9.

(3R) N-Methyl-3-pyrrolidinyl-(S)-cyclopentylmandelate, 14

In a 250 ml 3-neck flask equipped with Dean-Stark condenser, a mixture of methyl S(+)-cyclopentylmandelate, 13 (2 g, 8.8 mmol), (R)-3-hydroxy-N-methylpyrrolidine, (R)-3 (2 g, 20 mmol), and 100 ml of heptane was stirred and heated (110° C.) until 20 ml of heptane had been distilled. The temperature was reduced to 25"C, and approximately 0.003 g of sodium was added. The mixture was stirred and heated to 110° C. again for 3 hr as the distillation was continued. An additional piece of sodium (0.002 g) was added at the 1 hr point. More heptane was added at such a rate as to keep the reaction volume constant. The mixture was cooled to 0° C., mixed with 5 ml of water, and the organic layer was separated. The organic layer was extracted with 3N HCl. The acid extract was made alkaline (pH 10) with 5N NaOH and extracted three times with ether. Removal of dried ether solution (over $Na_2SO_4$) gave a clear, oily product 14 (1.6 g, 61.5%). $^1$H NMR ($CDCl_3$, 300 MHz): 1.28-1.80 [m, 9H], 2.15-2.25 (m, 1H), 2.30-2.40 (m, 1H), 2.37 (s, 3H), 2.65-2.80 (m, 3H), 2.90-3.00 (m, 1H), 3.85 (1H, brs, OH), 5.22 (m, 1H), 7.20-7.35 (m, 3H), 7.64-7.70 (m, 2H). $^{13}$C NMR ($CDCl_3$, 300 MHz):26.0, 26.4, 26.5, 26.7, 32.1, 42.0, 47.1, 54.8, 62.0, 76.5, 79.1, 125.8, 127.3, 128.0, 141.7, 175.3.

(3S) N-Methyl-3-pyrrolidinyl-(S)-cyclopentylmandelate, 15

Following the same procedure as for 14, except (S)-3 was used instead of (R)-3, a clear, oily product of 15 (2.33 g, 89.6%) was obtained. $^1$H NMR ($CDCl_3$, 300 MHz): 1.24-1.70 (m, 9H), 1.80-1.88 (m, 1H), 2.25-2.40 (m, 2H), 2.35 (s, 3H), 2.55-2.70 (m, 2H), 2.75-2.82 (m, 1H), 2.90-3.00 (m, 1H), 3.95 (1H, m, OH), 5.22 (m, 1H), 7.24-7.40 (m, 2H), 7.64-7.69 (m, 5H). $^{13}$C NMR ($CDCl_3$, 300 MHz):26.0, 26.3, 26.4, 26.7, 32.6, 42.0, 47.1, 54.9, 61.6, 76.4, 79.2, 125.8, 127.3, 128.0, 141.7, 175.2.

(2S,3'R) 3-(2-Cyclopentyl-2-phenyl-2-hydroxyacetoxy)-1-(methoxycarbonylmethyl)-1-methylpyrrolidinium bromide, 16 [Compound (h)]

Compound 14 (0.6 g, 1.96 mmol) in 30 ml of dry acetonitrile was combined with methyl bromoacetate (1.0 g, 6.4 mmol) at room temperature. The mixture was stirred for 3 hr. Evaporation of acetonitrile gave a crude product. The crude product was dissolved in a small volume of methylene chloride and poured into a 100 ml of dry ethyl ether to obtain a precipitate. This procedure was repeated three times and gave compound (h) as the product (0.81 g, 89%, white powder). $^1$H NMR ($CDCl_3$, 300 MHz): 1.30-1.70 (m, 8H), 1.82-1.95 (brs, 1H), 2.10-2.20 (m, 1H), 2.75-2.90 (m, 2H), 3.25, 3.60 (2s, total 3H, N—CH3), 3.75, 3.79 (2s, total 3H, O-Me), 4.10-4.60 (m, 4H), 4.92, 5.35 (2AB, total 2H, N—CH2-COOMe), 5.52-5.58 (m, 1H), 7.23-7.38 (m, 3H), 7.56-7.60 (m, 2H). $^{13}$C NMR ($CDCl_3$, 300 MHz); 25.8, 25.9; 26.3, 26.4; 26.4, 26.5; 27.0, 27.0; 29.8, 30.1; 45.9, 46.8; 50.2, 51.4; 53.2, 53.2; 62.2, 63.2; 64.6, 64.7; 69.6, 69.7; 72.8, 73.1; 79.4, 79.6; 125.7, 125.7; 127.6, 127.9; 128.2, 128.4; 141.0, 141.2; 165.3, 165.5; 173.9, 174.2.

(2S,3'S) 3-(2-Cyclopentyl-2-phenyl-2-hydroxyacetoxy)-1-methoxycarbonylmethyl-1-methylpyrrolidinium bromide, 17 [Compound (i)]

Following the same procedure as for Compound (h), except compound 15 was used instead of compound 14, the product Compound (i) (0.8 g, 88%, white powder) was obtained. $^1$H NMR ($CDCl_3$, 300 MHz): 1.30-1.75 (m, 8H), 1.80-1.90 (brs, 1H), 2.15-2.30 (m, 1H), 2.78-2.95 (m, 2H), 3.10, 3.65 (2s, total 3H, N—CH3), 3.75, 3.78 (2s, total 3H, O-Me), 4.15-4.52 (m, 4H), 4.85, 5.38 (2AB, total 2H, N—CH2-COOMe), 5.50-5.58 (m, 1H), 7.23-7.38 (m, 3H), 7.56-7.66 (m, 2H). $^{13}$C NMR ($CDCl_3$, 300 MHz): 25.8, 25.9; 26.2, 26.3; 26.3, 26.4; 26.8, 26.9; 29.4, 29.6; 45.6, 46.9; 50.1, 51.4; 53.1, 53.1; 62.2, 63.3; 64.8, 64.8; 69.5, 69.8; 72.8, 73.2; 79.4, 79.6; 125.6, 125.9; 127.6, 127.9; 128.2, 128.4; 140.7, 141.1; 165.2, 165.5; 173.9, 174.2.

Hydrolysis of Esters & HPLC Separations

The procedures used for obtaining the 2S-isomers 18a, 18b, 19a and 19b (white powder) were the same as thr 2R-isomers 8a, 8b, 9a and 9b.

(2S,1R,3'R) 3-(2-cyclopentyl-2-phenyl-2-hydroxyacetoxy)-1-(carboxymethyl)-1-methylpyrrolidinium inner salt. 18a $^1$H NMR ($CDCl_3$, 300 MHz):1.30-1.65 (m, 8H), 2.02-2.45 (m, 2H), 2.82-2.90 (m, 1H), 3.10-3.18 (m, 1H), 3.25 (s, 3H), 3.50-4.05 (m, 6H), 5.34-5.40 (m, 1H), 7.23-7.38 (m, 3H), 7.50-7.68 (m, 2H).

(2S,1'S,3'R) 3-(2-cyclopentyl-2-phenyl-2-hydroxyacetoxy)-1-(carboxymethy)-1-methylpyrrolidinium inner salt, 18b $^1$H NMR (CDCl3, 300 MHz):1.45-1.85 (m, 911), 2.05-2.15 (m, 1H), 2.80-2.90 (m, 1H), 3.00-3.10 (m, 1H), 3.35 (s, 3H), 3.70-3.80 (m, 1H), 3.90-4.10 (m, 4H), 4.22-4.35 (m, 1H), 5.50-5.60 (m, 1H), 7.36-7.55 (m, 311), 7.72-7.80 (m, 2H).

(2S,1'R,3'S) 3-(2-cyclopentyl-2-phenyl-2-hydroxyacetoxy)-1-(carboxymethyl)-1-methylpyrrolidinium inner salt, 19a $^1$H NMR (CDCl3, 300 MHz): 1.20-1.65 (m, 8H), 1.95-2.10 (m, 1H), 2.20 (brs, 1H), 2.40-2.50 (m, 1H), 2.78-2.90 (m, 1H), 3.15 (s, 3H), 3.70-3.90 (m, 2H), 3.96-4.20 (m, 4H), 5.38-5.50 (m, 1H), 7.20-7.38 (m, 3H), 7.55-7.65 (m, 2H).

(2S,1'S,3'S) 3-(2-cyclopentyl-2-phenyl-2-hydroxyacetoxy)-1-(carboxymethyl)-1-methylpyrrolidinium inner salt, 19b $^1$H NMR (CDCl3, 300 MHz): 1.35-1.70 (m, 8H), 2.00-2.15 (m, 1H), 2.70-2.90 (m, 2H), 3.00 (s, 3H), 3.42 (brs, 1H), 3.58-3.68 (m, 2H), 3.80-3.95 (m, 3H), 4.08-4.18 (m, 1H), 5.38-5.48 (m, 1H), 7.20-7.40 (m, 3H), 7.55-7.62 (m, 2H).

Receptor Binding Affinity

Receptor binding studies on soft anticholinergics isomers and their zwitterionic metabolite isomers, as well as glycopyrrolate, and N-methylscopolamine were performed with N-[$^3$H]-methyl-scopolamine (NMS) in assay buffer (phosphate-buffered saline, PBS, without $Ca^{++}$ or $Mg^{++}$, pH 7.4), following the protocol from Applied Cell Science Inc. (Rockville, Md.). A 10 mM NaF solution was added to the buffer as an esterase inhibitor. The assay mixture (0.2 mL) contained 20 µL diluted receptor membranes (receptor proteins: $M_1$, 38 µg/mL; $M_2$, 55 µg/mL; $M_3$, 27 µg/mL; $M_4$, 84 µg/mL). The final concentration of NMS for the binding studies was 0.5 nM. Specific binding was defined as the difference in [$^3$H] NMS binding in the absence and presence of 5 µM atropine for $M_1$ and $M_2$ or 1 µM atropine for $M_3$ and $M_4$. Incubation was carried out at room temperature for 2 hr. The assay was terminated by filtration through a Whatinan GF/C filter (pre-soaked overnight with 0.5% polyethyleneimine). The filter was then washed six times with 1 mL ice cold buffer (50 mM Tris-HCl, pH 7.8, 0.9% NaCl), transferred to vials, and 5 mL of Scintiverse was added. Detection was performed on a Packard 31800 liquid scintillation analyzer (Packard Instrument Inc., Downer Grove, Ill.). Data obtained from the binding experiments were fitted to the equation %[$^3$H] NMS bound=100–[$100x^n/k(1+x^n/k)$], to obtain the Hill coefficient n, and then to the equation %[$^3$H] NMS bound=100–[$100x^n/IC_{50}/(1+x^n/IC_{50})$], to obtain the $IC_{50}$ values (x being the concentration of the tested compound). Based on the method of Cheng and Prusoff (8), $K_i$ was derived from the equation $K_i=IC_{50}/(1+L/K_d)$, where L is the concentration of the radio-ligand. $IC_{50}$ represents the concentration of the drug causing 50% inhibition of specific radioligand binding, and $K_d$ represents the dissociation constant of the radioligand receptor complex. Data were analyzed by a non-linear least-square curve-fitting procedure using Scientist software (MicroMath Inc., Salt Lake City, Utah).

Determination of $pA_2$ Values

Male guinea pigs weighing about 400 g were obtained from Harlan Inc. (Indianapolis, Ind.) and fasted overnight. Animals were sacrificed by decapitation, and the ileum (the region of 5 cm upward of the cecum) was isolated and removed, The ileum was cut into 2.5 cm pieces and suspended in an organ bath containing 30 mL of mixture of Tyrode's solution and 0.1 mM hexamethonium bromide. The organ bath was constantly aerated with oxygen and kept at 37° C. One end of the ileum strip was attached to a fixed support at the bottom of the organ bath, and the other end to an isometric force transducer (Model TRN001, Kent Scientific Corp., Conn.) operated at 2-10 g range. The ileum strip was kept at a 2 g tension, and carbachol was used as antagonist. The ileum contracted cumulatively upon the addition of consecutive doses of carbachol (10-20 µL of $2\times10^{-4}$-$2\times10^{-3}$ M in water solution). Contractions were recorded on a physiograph (Kipp & Zonen Flarbed Recorder, Holland). After the maximum response was achieved, the ileum was washed three times, and a fresh Tyrode's solution containing appropriate concentration of the antagonist (anticholinergic compound tested) was replaced. An equilibration time of 10 min was allowed for the antagonists before the addition of carbachol, In each experiment, 5 to 6 different concentrations were used, and a Schild plot was used to obtain the $pA_2$ values. Four trials were performed for each antagonist.

In Vivo Mydriatic Studies

The mydriatic effects of eight completely resolved zwitterionic isomers were compared to those of glycopyrrolate, tropicamide, (±) 3-(2-cyclopentyl-2-phenyl-2-hydroxyacetoxy)-1-(carboxymethyl)-1-methylpyrrolidinium inner salt [(±)-GA] and (2R) 3-(2-cyclopentyl-2-phenyl-2-hydroxyacetoxy)-1-(carboxymethyl)-1-methylpyrrolidinium inner salt [(2R)-GA] in rabbit eyes. Four healthy, male New-Zealand white rabbits weighting about 3.5 kg were used. 100 µL of compound in water solution (pH 6.5) at various concentrations were administered in the eyes. Compound solutions were applied to one eye, and water was applied to the other eye that served as control. Experiments were carried out in a light- and temperature-controlled room. At appropriate time intervals, the pupil diameters of both eyes were recorded. Per cent difference in pupil diameters between each time-point and zero time-point were calculated for both treated and control eyes and reported as mydriatic responses. Control eye dilations were monitored to determine whether systemic absorption had occurred or riot. The area under the mydriatic response-time curve ($AUC^{eff}$) was calculated by the trapezoidal rule, and it was used to compare the activity and duration of action of the tested compounds.

Statistical Analysis

Receptor binding affinities and $pA_2$ values were compared using student t-tests. Mydriatic activities (maximum response Rmax % and area under the effect curves $AUC_{eff}$) were compared using ANOVA. A significance level of P<0.05 was used in all cases.

RESULTS AND DISCUSSION

Synthesis

Five soft anticholinergic ester isomers and eight zwitterionic metabolite acid isomers were newly synthesized. The 2R diastereoisomers [Compounds (e), (f), (g), 8a, 8b, 9a and 9b] were obtained by the synthetic pathways described below.

Scheme 2

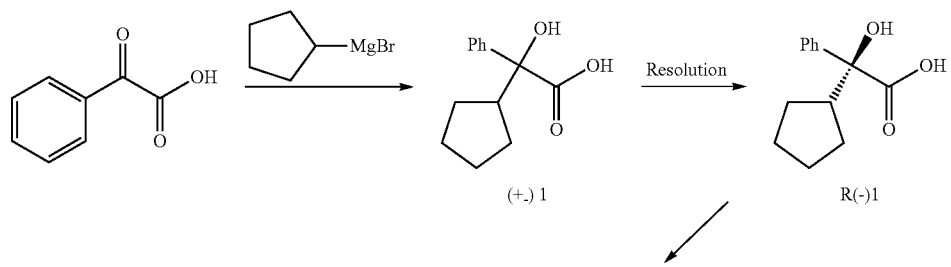

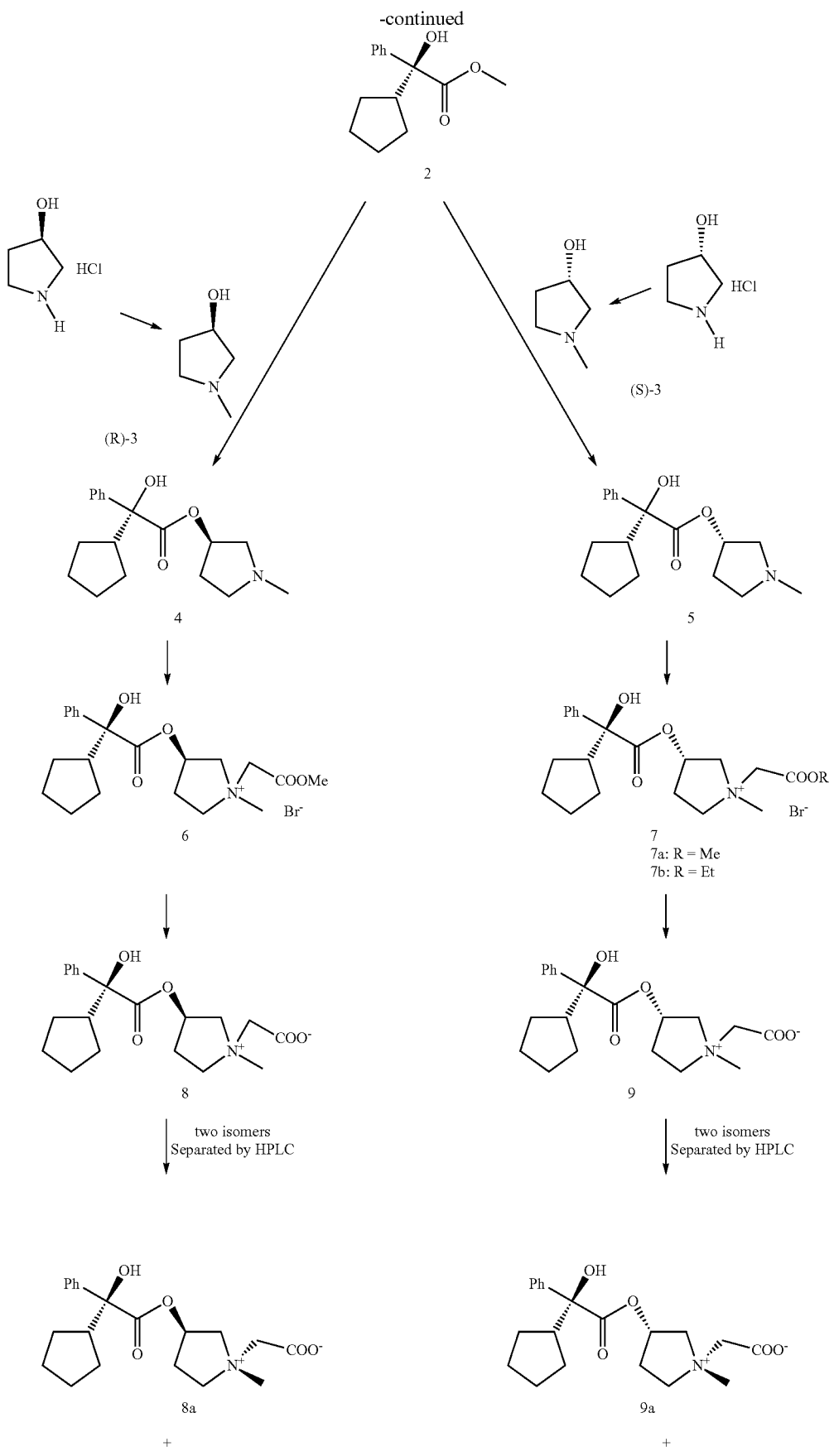

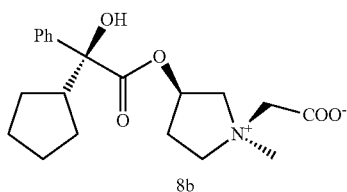

8b

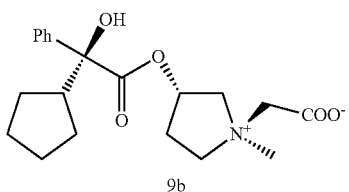

9b

As shown in Scheme 2, first the racemic cyclopentylmandelic acid 1 was synthesized with cyclopentylmagnesium bromide and benzoylformic acid. This racemic acid was resolved by repeated crystallization of the salts produced between this acid and (−)-strychnine. The left rotatory (−22.5″) optically pure free acid R(−)1 was recovered by basification of the salts with sodium hydroxide solution followed by acidification with hydrochloric acid. Methylation of R(−)1 with methyl iodide and potassium carbonate in DMF at room temperature yields methyl 2R(—) cyclopentylmandelate, R(−)2. Transesterfication of R(−)2 with R-3-hydroxy-N-methylpyrrolidine, (R)-3 (made from R-3-hydroxypyrrolidine with paraformaldehyde and formic acid), gave (3R)—N-methyl-3-pyrrolidinyl-2R-cyclopentylmandelate 4; or with S-3-hydroxy-N-methylpyrrolidine (S)-3 (made from S-3-hydroxypyrrolidine with paraformaldehyde and formic acid), gave (3S)—N-methyl-3-pyrrolidinyl-2R-cyclopentyl mandelate 5. Quarternization of 4 and 5 with methyl or ethyl bromoacetate in acetonitrile gave 6 [Compound (e)], 7a [Compound W], and 7b [Compound (g)]. Each of these has two diastereoisomers, due to the nitrogen chiral center, with a ratio of 2 to 1 (R:S=2:1) that was shown in 1H NMR spectra. Hydrolysis of 6 [Compound (e)] and 7a [Compound (f)] gave their zwitterionic inner salts 8 and 9. Each zwitterionic salt also possesses two diastereoisomers with a ratio of 2 to 1 that could be separated by HPLC to give zwitterionic isomers 8a, 8b & 9a and 9b. From 1H MAR, 8a, 8b, and 9a, 9b were evidenced to be pairs of diastereoisomers based on chiral nitrogen. To identify the absolute configuration of these isomers, 8b was chosen and dissolved in CDCl$_3$ for the investigation of nuclear overhauser effect (NOE). The 2D $^1$H—$^1$H NOESY spectrum showed that the methyl group on the nitrogen was at the same side as the hydrogen at the 3-position of pyrrolidinium ring. Accordingly, the configuration of the nitrogen should be the S form, and the absolute stereochemistry of 8b was proved to be (2R,1′R,3′S) 3-(2-cyclopentyl-2-phenyl-2-hydroxyacetoxy)-1-(carboxymethyl)-1-methylpyrrolidinium inner salt. Therefore, 8a was (2R,1′R,3′R) 3-(2-cyclopentyl-2-phenyl-2-hydroxyacetoxy)-1-(carboxymethyl)-1-methylpyrrolidinium inner salt; 9a was (2R, 1′R,3′S) 3-(2-cyclopentyl-2-phenyl-2-hydroxyacetoxy)-1-(carboxymethyl)-1-methylpyrrolidinium inner salt; and 9b was (2R,1′S,3′S) 3-(2-cyclopentyl-2-phenyl-2-hydroxyacetoxy)-1-(carboxymethyl)-1-methylpyrrolidinium inner salt.

Grover and coworkers previously reported [*J. Org. Chem.* 65: 6283-6287 (2000)] the highly stereoselective synthesis of (S)-cyclopentylmandelic acid in five steps starting with (S)-mandelic acid. Modification of their procedure afforded pure S(+)-cyclopentylmandelic acid in three steps with good yield. As depicted in Scheme 3, reaction of S(+)-mandelic acid with pivaldehyde in the presence of the catalyst trifluoromethanesulfonic acid gave the product of cis-(2S,5S)-2-(tert-butyl)-5-phenyl-1,3-dioxolan-4-one, 10, in about 90% yield. At −78° C., deprotonation of 10 with lithium bis(trimethylsilyl) amide followed by adding cyclopentyl bromide generated cis-(2S,5S)-2-(tert-butyl)-5-cyclopentyl-5-phenyl-1,3-dioxolan-4-one, 11. Base hydrolysis of 11 with potassium hydroxide, followed by acidification with hydrochloric acid provided the expected (S)-(+)-cyclopentylmandelic acid 12. After this step, the same procedures as for 8a, 8b, 9a and 9b including methylation, esterification, quaternization and hydrolyses were followed to give the final four zwitterionic isomers, (2S,1′R,3′R) 3-(2-cyclopentyl-2-phenyl-2-hydroxyacetoxy)-1-(carboxymethyl)-1-methylpyrrolidinium inner salt 18a [2S1′R3′R-GA]; (2S,1′S,3′R) 3-(2-cyclopentyl-2-phenyl-2-hydroxyacetoxy)-1-(carboxymethyl)-1-methylpyrrolidinium inner salt 1.8b [2S1′S3′R-GA]; (2S,1′R,3′S) 3-(2-cyclopentyl-2-phenyl-2-hydroxyacetoxy)-1-(carboxymethyl)-1-methylpyrrolidinium inner salt 19a [2S1′R3′S-GA]; and (2S,1′S,3′S) 3-(2-cyclopentyl-2-phenyl-2-hydroxyacetoxy)-1-(carboxymethyl)-1-methylpyrrolidinium inner salt 19b [2S1′S3′S-GA]. They were also characterized by NMR.

Scheme 3

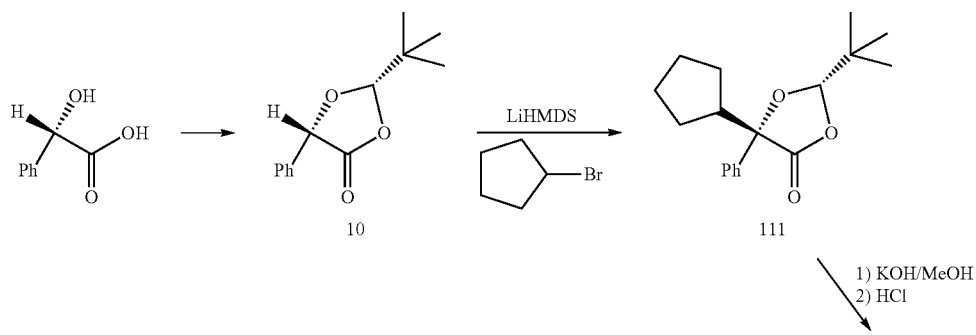

1) KOH/MeOH
2) HCl

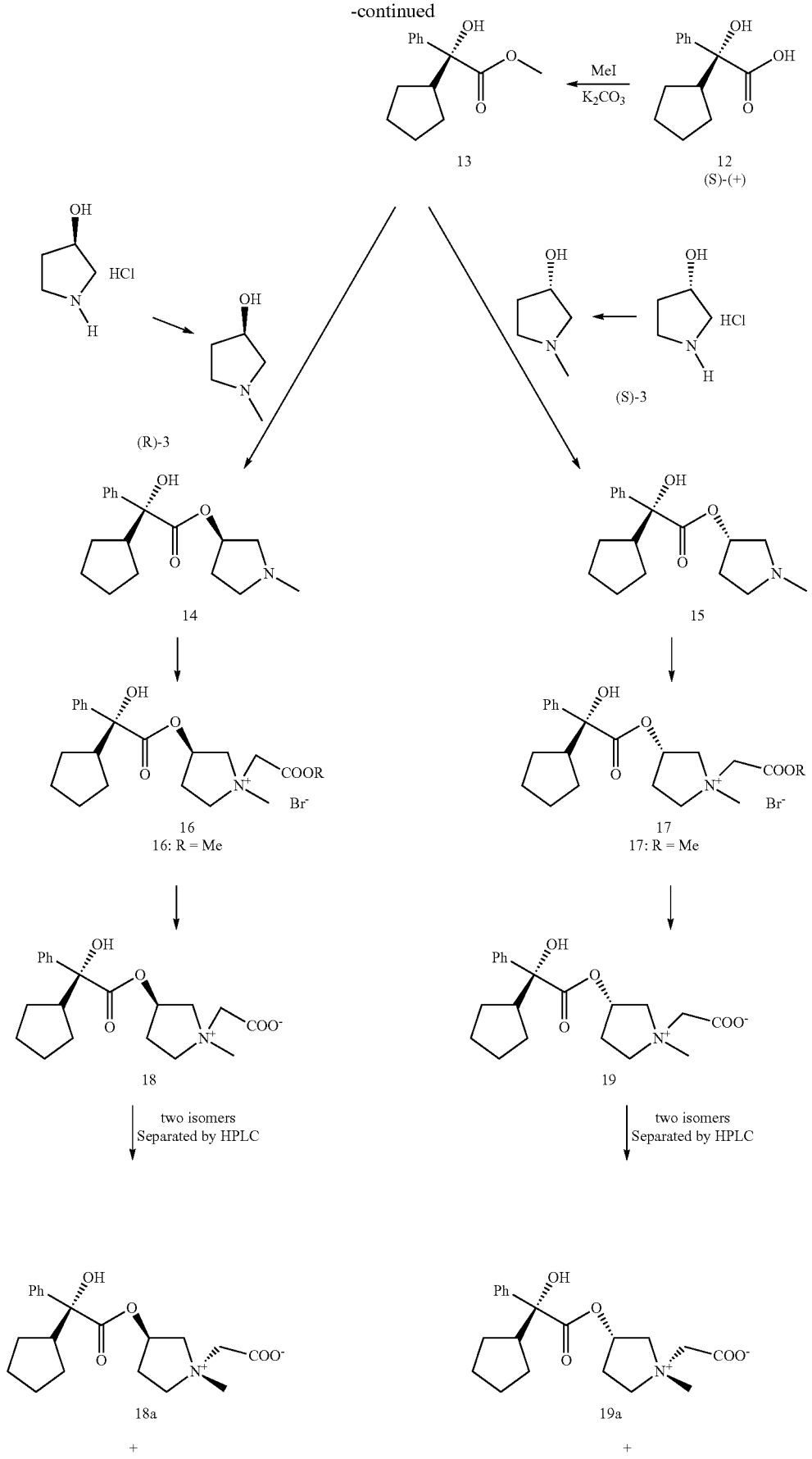

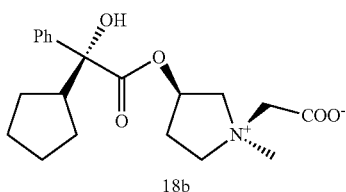

18b

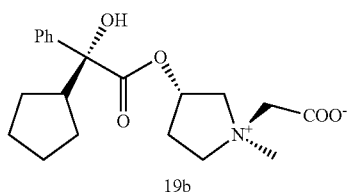

19b

Receptor Binding Studies The receptor binding affinities of soft analogs, $pK_i$, determined by radioligand binding assays using human cloned muscarinic receptor subtypes, $M_1$-$M_4$, are presented in Table 4.

methyl ester Compound (c) and the ethyl ester Compound (d)], racemic and 2R isomeric GA (the zwitterionic metabolite) as well as those of glycopyrrolate and N-methylscopolamine. $pK_i$ of the racemic forms, Compound (a) and Com-

TABLE 4

Receptor binding affinities, $M_3/M_2$ selectivities, and $pA_2$ values.

| Compound | Subtypes of cloned muscarinic receptors [a] | | | | Selectivity [b] | |
|---|---|---|---|---|---|---|
| | $M_1$ | $M_2$ | $M_3$ | $M_4$ | $M_3/M_2$ | $pA_2$ [c] |
| (a) [d] | 7.91 ± 0.05 | 7.79 ± 0.11 | 7.80 ± 0.10 | 8.29 ± 0.19 | 1.0 ± 0.0 | 7.90 ± 0.13 |
| | (1.02 ± 0.12) | (1.25 ± 0.08) | (1.17 ± 0.18) | (1.12 ± 0.05) | | |
| (b) [d] | 7.51 ± 0.17 | 7.32 ± 0.07 | 7.54 ± 0.15 | 7.94 ± 0.09 | 1.8 ± 0.7 | 7.36 ± 0.34 |
| | (0.91 ± 0.09) | (1.23 ± 0.06) | (1.18 ± 0.08) | (1.18 ± 0.09) | | |
| (±)-GA [d] | 6.19 ± 0.06 | 5.48 ± 0.13 | 5.84 ± 0.07 | 6.44 ± 0.06 | 2.4 ± 0.7 | 6.42 ± 0.30 |
| | (1.11 ± 0.06) | (1.02 ± 0.20) | (1.01 ± 0.07) | (0.84 ± 0.06) | | |
| (c) [e] | 8.89 ± 0.04 | 8.87 ± 0.05 | 9.00 ± 0.06 | 9.52 ± 0.01 | 1.4 ± 0.2 | 8.31 ± 0.05 |
| | (0.83 ± 0.11) | (1.10 ± 0.11) | (0.83 ± 0.01) | (0.83 ± 0.01) | | |
| (d) [e] | 8.67 ± 0.16 | 8.84 ± 0.34 | 8.74 ± 0.02 | 8.85 ± 0.13 | 1.1 ± 1.1 | 8.55 ± 0.16 |
| | (0.86 ± 0.08) | (0.92 ± 0.01) | (1.09 ± 0.15) | (0.89 ± 0.02) | | |
| 2R-GA [e] | 8.11 ± 0.16 | 7.48 ± 0.12 | 8.12 ± 0.10 | 8.23 ± 0.12 | 4.4 ± 0.3 | 7.20 ± 0.19 |
| | (1.12 ± 0.25) | (0.95 ± 0.11) | (0.80 ± 0.01) | (1.02 ± 0.10) | | |
| (e) [f] | 8.99 ± 0.04 | 9.01 ± 0.06 | 9.06 ± 0.14 | 9.45 ± 0.01 | 1.1 ± 0.1 | — |
| | (1.19 ± 0.12) | (1.03 ± 0.09) | (1.03 ± 0.18) | (1.52 ± 0.66) | | |
| (f) [f] | 8.50 ± 0.03 | 7.90 ± 0.04 | 8.60 ± 0.09 | 8.87 ± 0.09 | 5.0 ± 1.1 | — [h] |
| | (1.30 ± 0.20) | (1.07 ± 0.17) | (1.04 ± 0.27) | (1.08 ± 0.01) | | |
| (h) [f] | 7.23 ± 0.01 | 7.22 ± 0.03 | 6.99 ± 0.08 | 7.57 ± 0.01 | 0.6 ± 0.1 | — |
| | (0.98 ± 0.06) | (1.09 ± 0.18) | (1.15 ± 0.13) | (1.11 ± 0.03) | | |
| (i) [f] | 6.40 ± 0.05 | 6.47 ± 0.08 | 5.95 ± 0.02 | 6.39 ± 0.01 | 0.3 ± 0.0 | — |
| | (0.92 ± 0.09) | (0.99 ± 0.16) | (1.06 ± 0.03) | (1.44 ± 0.75) | | |
| (j) [f] | 8.68 ± 0.11 | 8.21 ± 0.10 | 8.64 ± 0.07 | 8.71 ± 0.38 | 2.8 ± 0.8 | — |
| | (1.21 ± 0.33) | (1.27 ± 0.11) | (1.33 ± 0.16) | (1.15 ± 0.03) | | |
| 8a [g] | 7.04 ± 0.09 | 6.43 ± 0.07 | 6.95 ± 0.04 | 7.00 ± 0.05 | 3.5 ± 0.2 | 6.32 ± 0.23 |
| | (0.97 ± 0.13) | (0.85 ± 0.21) | (1.06 ± 0.04) | (0.93 ± 0.01) | | |
| 8b [g] | 8.13 ± 0.06 | 7.63 ± 0.02 | 8.15 ± 0.02 | 8.33 ± 0.04 | 3.3 ± 0.0 | 7.45 ± 0.21 |
| | (1.25 ± 0.01) | (0.82 ± 0.15) | (0.84 ± 0.17) | (1.00 ± 0.06) | | |
| 9a [g] | 7.98 ± 0.01 | 7.39 ± 0.09 | 8.04 ± 0.01 | 8.15 ± 0.06 | 5.2 ± 0.7 | 7.33 ± 0.28 |
| | (1.02 ± 0.03) | (0.80 ± 0.22) | (0.96 ± 0.03) | (1.01 ± 0.06) | | |
| 9b [g] | 8.32 ± 0.04 | 7.64 ± 0.01 | 8.46 ± 0.12 | 8.56 ± 0.07 | 5.5 ± 1.1 | 7.15 ± 0.12 |
| | (1.01 ± 0.01) | (1.00 ± 0.04) | (0.80 ± 0.21) | (0.86 ± 0.06) | | |
| 18a [g] | 5.87 ± 0.04 | 5.65 ± 0.06 | 5.54 ± 0.16 | 5.79 ± 0.12 | 0.8 ± 0.1 | 5.14 ± 0.38 |
| | (1.06 ± 0.05) | (1.24 ± 0.07) | (1.02 ± 0.12) | (0.88 ± 0.04) | | |
| 18b [g] | 6.67 ± 0.06 | 6.35 ± 0.01 | 6.22 ± 0.05 | 6.47 ± 0.01 | 0.7 ± 0.0 | 5.69 ± 0.13 |
| | (1.08 ± 0.03) | (1.01 ± 0.01) | (1.04 ± 0.08) | (1.30 ± 0.28) | | |
| 19a [g] | <4.5 | <4.5 | <4.5 | <4.5 | — | <4 |
| | — | — | — | — | | |
| 19b [g] | 5.84 ± 0.06 | 5.61 ± 0.00 | 5.61 ± 0.09 | 5.85 ± 0.05 | 1.0 ± 0.2 | 5.03 ± 0.26 |
| | (1.13 ± 0.10) | (1.20 ± 0.02) | (1.03 ± 0.01) | (0.95 ± 0.18) | | |
| glycopyrrolate | 9.76 ± 0.05 | 9.19 ± 0.18 | 8.73 ± 0.05 | 9.90 ± 0.08 | 0.4 ± 0.2 | 8.57 ± 0.12 |
| | (1.37 ± 0.20) | (0.99 ± 0.11) | (1.14 ± 0.25) | (1.02 ± 0.01) | | |
| scopolamine methyl bromide | 9.69 ± 0.01 | 9.18 ± 0.21 | 9.29 ± 0.12 | 9.92 ± 0.21 | 1.3 ± 0.4 | 9.16 ± 0.19 |
| | (0.92 ± 0.10) | (1.02 ± 0.02) | (1.07 ± 0.01) | (0.90 ± 0.04) | | |

[a] Receptor binding at cloned human muscarinic receptors ($M_1$-$M_4$ subtypes); $pK_i$ data represent mean ± SD of 3 experiments, and the numbers in parentheses denote Hill slopes.
[b] $M_3/M_2$ affinity ratio (times)
[c] $pA_2$ values were determined on 4-6 ileum strips obtained from different animals, and data represent mean ± SD.
[d] Racemic forms.
[e] Isomers based on the chiral center 2.
[f] Isomers based on the chiral centers 2 & 3'.
[g] Isomers based on the chiral centers 2, 3', & 1'.
[h] Data not available or not detectable.

The $pK_i$ of newly synthesized isomers were compared with that of the racemic and 2R isomeric parent soft drugs [the pound (b), showed lower receptor binding affinities than their corresponding 2R isomers (7.8-8.3 vs. 8.7-9.5), confirming that stereospecificity is important at these receptors. The potencies of these 2R isomers are similar to those of glycopyrrolate (8.7-9.9) and N-methylscopolamine (9.2-9.9). Resolution of 2 and 3' chiral centers of racemic Compound (a) resulted in four stereoisomers, Compounds (e), (t), (h) and (i) with $pK_i$ values of 9.0-9.5, 7.9-8.9, 7.0-7.6 and 6.0-6.5, respectively. These numbers indicate that among the methyl ester isomers, not only 2R isomers are more potent than the corresponding 2S isomers, but also that 3'R isomers are more potent than 3'S isomers. The 2R3'S isomer of the ethyl ester, Compound (j), showed a $pK_i$ value of 8.2-8.7, the same as the 2R3'S isomer of the methyl ester, In the same table, the $M_3/M_2$ muscarinic-receptor subtype-selectivities were also calculated. Contrary to the previously reported 2R isomer of the methyl and ethyl esters, Compounds (c) and (d), that show no $M_3 1 M_2$ subtype selectivity, the 2R3'S isomers of the methyl and ethyl esters, Compounds (e) and (j), show significantly increased $M_3/M_2$ muscarinic-receptor subtype-selectivity (p<0.01, t-test assuming equal variances). The $M_3$ affinity was 5.0±1.1 times of $M_2$ affinity in the case of Compound (e), and 2.8±0.8 times in the case of Compound (j). This indicates that the configuration of chiral center 3' may play an important role in the safety profile of this type of soft anticholinergics.

The receptor-binding $pK_i$ of racemic (±) GA and isomeric 2R-GA obtained earlier are also shown in Table 4. In agreement with soft drug design principles that the acidic moiety formed by hydrolysis of the parent soft drug ester inactivates the drug, the zwitterions were found considerably less active than their corresponding parent esters, e.g. $pK_i$ of (±)GA, 5.5-6.4, vs. Compound (a), 7.8-8.3, and Compound (b), 7.3-7.9; and $pK_i$ of 2R-GA, 7.5-8.2, vs. Compound (c), 8.9-9.5, and Compound (d), 8.7-8.9 (3-4). As discussed previously, the zwitterionic metabolite retains some activity because the electronic distribution in its structures somewhat resembles those of the neutral, active anticholinergics, In this study, to obtain a better picture of the stereospecificity/stereoselectivity of this type of anticholinergic, the zwitterionic form was chosen as a model compound for the investigation, since the zwitterion GA, either in its racemic or its 2R isomeric form, was very soluble and stable in aqueous solutions (buffer or biological media, pH 6-8). In addition, 2R-GA has been found active at topical sites (e.g. in rabbit eyes), and could be excreted unchanged, rapidly through urine ($t_{1/2}$ 10-15 min after i.v. in rats). In Table 4, the $pK_i$ of the completely resolved eight isomers of ±GA, 2R1'R3S-GA, 2R1'S3'R-GA, 2R1'R3'S-GA, 2R1'S3'S-GA, 2S1R3'R-GA, 2S1'S3R-GA, 2S1'R3'S-GA, 2S1'S3'S-GA was in a wide range of 4.5-8.6. In all cases, the 2R isomers are more potent than the 2S isomers, and the 1'S isomers are more potent than the 1'R isomers, The comparative potencies for 3'R and 3'S isomers varied depending on the configuration of chiral center 2, e.g. 2R1'R3'S>2R1'R3'R and 2R1'S3'S>2R1'S3'R; but 2S1'R3'R> 2S1'R3'S and 2S1'S3'R>2S1'S3'S. Also, the same as previous methyl ester isomers, among 2R isomers of the acid, the 2R3'S isomers (2R1R3'S and 2R1'S3'S) showed highest $M_3/M_2$ muscarinic-receptor subtype-selectivities (5.2-5.5 times) followed by the 2R3'R isomers (2R1'R3'R and 2R1'S3'R, 3.3-3.5 times), The 2S isomers did not show any $M_3/M_2$ selectivity. Thus, the importance of the chiral center 2 and 3' configuration (2R3'S) on the $M_3/M_2$ selectivity of this type of anticholinergics has been demonstrated.

In order to show the comparative stereoselectivity (times) based on each chiral center, the ratio of binding activities of each corresponding paired isomers was calculated, and the results are shown in Table 5, The results displayed are comparative potencies (times) calculated from the receptor binding affinities, $pK_i$, in Table 4. The difference in receptor binding affinities between 2R and 2S isomers is significant (27 to 447 times for the methyl ester isomers, and 6 to 4467 times for zwitterion isomers). The 3'R isomers of the methyl ester (with chiral center I unresolved, 2R3'R & 2S3'R methyl esters) are more active (1.5 to 12.9 times) than their corresponding 3'S isomers (2R3'S & 2S3'S methyl esters). However, in the acid, the 3'S isomers were not always more active than the corresponding 3'R isomers, e.g. in 2R isomers, 3'S>3'R (2R1'R3'S>2R1'R3'R and 2R1'S3'S>2R1'S3'R) but in 2S isomers, 3'R>3'S (2S1'R3'R>2S1'R3'S and 2S1'S3R>2S1'S3'S). Also, there are more significant differences between 2R1'R3'S and 2R1'R3'R than between 2R1'S'3'S and 2R1'S3'R (8.7 to 14.1 times vs. 1.0 to 2.0 times), and between 2S1'R3'R and 2S1'R3'S than between 2S1'S3'R and 2S1'S3'S (11.0 to 23.4 times vs. 4.1 to 6.8 times). These results indicate that the activity based on chiral center 3' can be affected by the configuration of the other two chiral centers, 2 and 1'. When comparing all eight zwitterion isomers (with all three chiral centers resolved), it clearly shows that 1'S isomers were more active than the corresponding 1'R isomers in all cases (1.8-22.4 times).

TABLE 5

Comparative stereoselectivities[a]

| Compound | Subtypes of cloned muscarinic receptors[b] | | | | Description[f] |
|---|---|---|---|---|---|
| | $M_1$ | $M_2$ | $M_3$ | $M_4$ | |
| Methyl Esters | | | | | |
| 2R3'S/ 2S3'S[c] | 125.9 | 26.9 | 446.7 | 302.0 | 2R > 2S |
| 2R3'R/ 2S3'R[c] | 57.5 | 61.7 | 117.5 | 75.9 | |
| 2R3'R/ 2R3'S[d] | 3.1 | 12.9 | 2.9 | 3.8 | 3R > 3S |
| 2S3'R/ 2S3'S[d] | 6.8 | 5.6 | 11.0 | 1.5 | |
| Zwitterions | | | | | |
| 2R1'R3'R/ 2S1'R3'R[c] | 14.8 | 6.0 | 25.7 | 16.2 | 2R >> 2S |
| 2R1'S3'R/ 2S1'S3'R[c] | 28.8 | 19.1 | 85.1 | 72.4 | |
| 2R1'R3'S/ 2S1'R3'S[c] | 3020.0 | 776.2 | 3467.4 | 4466.8 | |
| 2R1'S3'S/ 2S1'S3'S[c] | 302.0 | 107.2 | 707.9 | 512.9 | |
| 2R1'R3'S/ 2R1'R3'R[d] | 8.7 | 9.1 | 12.3 | 14.1 | 3S > 3R |
| 2R1'S3'S/ 2R1'S3'R[d] | 1.5 | 1.0 | 2.0 | 1.7 | |
| 2S1'R3'R/ 2S1'R3'S[d] | 23.4 | 14.1 | 11.0 | 19.5 | 3R > 3S |
| 2S1'S3'R/ 2S1'S3'S[d] | 6.8 | 5.5 | 4.1 | 4.2 | |
| 2R1'S3'R/ 2R1'R3'R[e] | 12.3 | 15.8 | 15.8 | 21.4 | 1R < 1S |
| 2R1'S3'S/ 2R1'R3'S[e] | 2.2 | 1.8 | 2.6 | 2.6 | |
| 2S1'S3'R/ 2S1'R3'R[e] | 6.3 | 5.0 | 5.2 | 4.8 | |
| 2S1'S3'S/ 2S1'R3'S[e] | 21.9 | 12.9 | 12.9 | 22.4 | |

[a]Affinity ratio (times) between each two isomers based on each of the three different chiral centers.
[b]Receptor binding at cloned human muscarinic receptors ($M_1$-$M_4$ subtypes)
[c]Affinity ratio based on the chiral center 2.
[d]Affinity ratio based on the chiral center 3.
[e]Affinity ratio based on the chiral center 1.
[f]Concluded stereoselectivities In all cases, the Hill coefficients (n) were not very different from unity indicating that, in general, drug-receptor interactions obeyed the law of action and binding took place at only one site.

pA$_2$ Studies

The pA$_2$ values determined from guinea pig ileum contraction assays, which represent the negative logarithm of the molar concentration of the antagonist that produces a two-fold shift to the right in an agonist's concentration-response curve, are a classical functional study of anticholinergic affinity (at M$_3$ muscarinic receptors). For the soft anticholinergics of the present study, the pA$_2$ values obtained from ileum longitudinal contractions by using carbachol as agonist with the method of van Rossum [*Arch. Int. Pharcodyn.* 143: 299-330(1963)] are presented in Table 4. The pill values are in general, comparable to the pK$_i$ values obtained in the M$_3$ receptor binding studies. The pA$_2$ values of newly developed zwitterionic isomers significantly differed between 2R and 2S configurations (6.32 to 7.45 and <4 to 5.69, respectively, p<0.01, t-test assuming equal variances). Similar to the above reported 2R isomer (2R-GA), the pA$_2$ values of completely resolved 2R isomers (2R1'R3'R-GA, 2R1'S3'R-GA, 2R1'R3'S-GA, and 2R1'S3'S-GA) are 1 to 2 less than those of the corresponding 2R ethyl and methyl parent ester soft drugs, indicating a one to two order of magnitude less activity of these zwitterionic compounds. The retained moderate activity of some zwitterionic metabolite isomers is probably due to a spatially-close structures that resembles those of the neutral, active anticholinergics. In the active 2R isomers, while 2R1'R3'R-GA showed a lower value (6.32), all others showed a similar moderate contraction activity (about 7.15 to 7.45).

Mydriatic Activities

The mydriatic effects of the fully resolved eight zwitterionic isomers were compared to those of (±)GA, 2R-GA, glycopyrrolate and tropicamide in vivo in rabbits. Following a 100 µl topical administration, the mydriatic responses were recorded at appropriate time-intervals as % changes in pupil size. The maximum response (R$_{max}$, % change in pupil size at 30 min to 1 h after administration) and area under the response-time curve (AUC$^{eff}_{0-168h}$) are shown in Table 6.

TABLE 6

Maximum response (R$_{max}$, maximum % change in pupil size) and area under the response-time curve (AUC$_{eff}$) after topical administration (0.1 mL).[a]

| Compound | Conc. (%) | R$_{max}$ (%) | AUC$^{eff}_{0-168\,h}$ |
|---|---|---|---|
| (±)GA[b] | 0.01 | 1.85 ± 2.14 | 0.7 ± 0.9 |
|  | 1 | 45.37 ± 8.19 | 119 ± 34 |
| 2R-GA[b] | 0.01 | 31.00 ± 7.14 | 73 ± 24 |
|  | 0.1 | 50.34 ± 7.92 | 182 ± 40 |
| 2R1'R3'R-GA (8a) | 0.1 | 24.40 ± 8.33 | 89 ± 50 |
| 2R1'S3'R-GA (8b) | 0.1 | 51.79 ± 16.62 | 308 ± 106 |
| 2R1'R3'S-GA (9a) | 0.1 | 43.90 ± 7.63 | 216 ± 29 |
| 2R1'S3'S-GA (9b) | 0.1 | 47.32 ± 19.64 | 274 ± 134 |
| 2S1'R3'R-GA (18a) | 0.1 | 0.00 ± 0.00 | 0 ± 0 |
|  | 0.4 | 7.44 ± 0.60 | 11 ± 1 |
| 2S1'S3'R-GA 18(b) | 0.1 | 3.87 ± 4.49 | 13 ± 15 |
|  | 0.4 | 14.88 ± 1.19 | 37 ± 3 |
| 2S1'R3'S-GA 19(a) | 0.1 | 0.00 ± 0.00 | 0 ± 0 |
|  | 0.4 | 0.00 ± 0.00 | 0 ± 0 |
| 2S1'S3'S-GA 19(b) | 0.1 | 3.87 ± 4.49 | 13 ± 15 |
|  | 0.4 | 11.01 ± 3.81 | 28 ± 2 |
| glycopyrrolate[b] | 0.05 | 48.73 ± 12.66 | 2476 ± 847 |
|  | 0.1 | 52.95 ± 10.93 | 3732 ± 866 |
| tropicamide[b] | 0.5 | 44.64 ± 11.17 | 451 ± 121 |

[a]Data represent mean ± SD of four trials.
[b]Data adapted from other testing.

Figure 4:
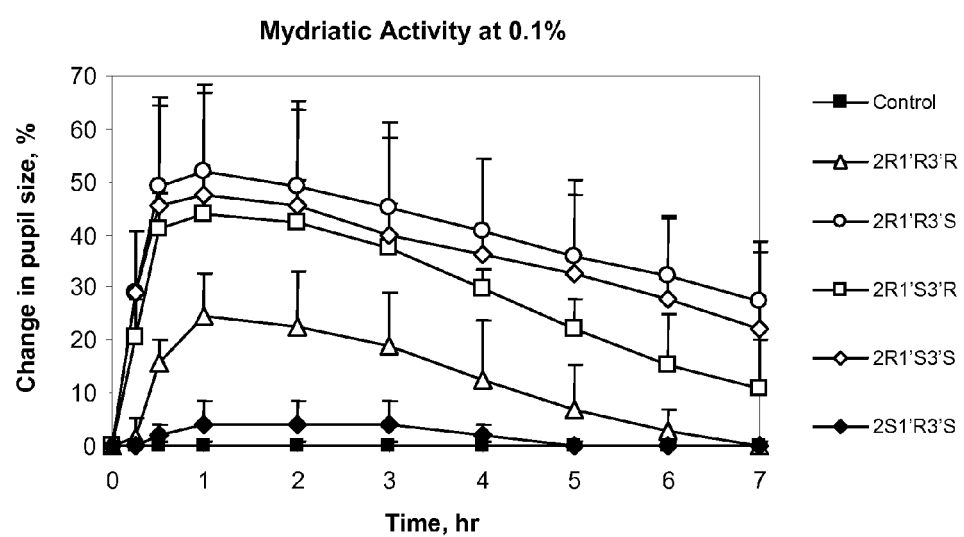
FIG. 4 is a graph of mydriatic activities of various zwitterionic isomers at 0.1% concentrations over a seven hour period.
Figure 5:
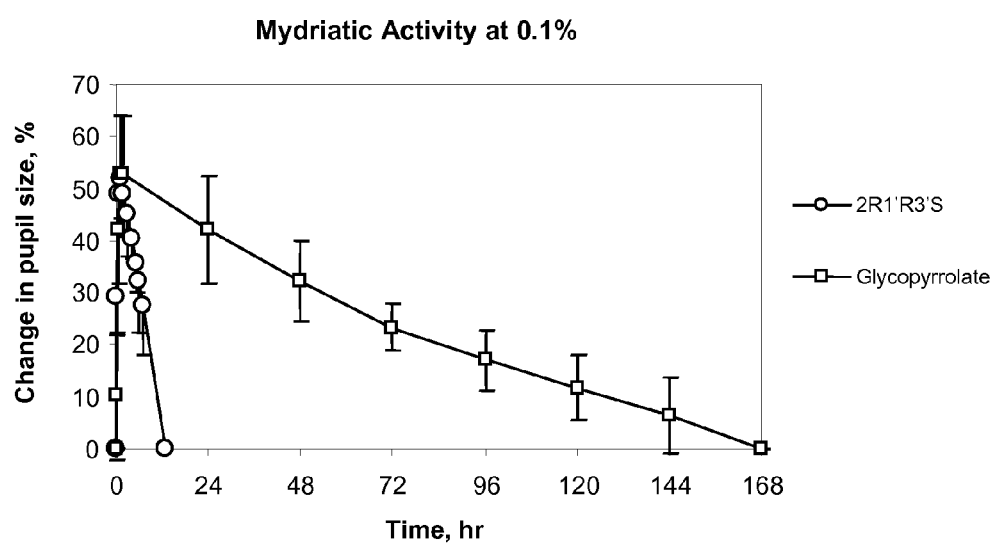
FIG. 5 is a graph comparing the mydriatic activity of the most active zwitterionic isomers with glycopyrrolate at 0.1% concentrations.

The results indicate that, as in the in vitro studies, the 2R isomers are much more potent than the 2S isomers (even when the 2S dose was increased to 0.4%); and 2R1'R3'R-GA is less potent than the other three 2R isomers. In FIG. 4, the activity-time profiles of four 2R and one 1'S isomers (the most active S isomer) at 0.1% are displayed. The pupil-dilating potency of the most potent three 2R isomers at a dose of 0.1% is similar to that of 0.05 to 0.1% of glycopyrrolate and 0.5% of tropicamide, however, their duration of actions was much shorter than that of the "hard" glycopyrrolate (AUC 200-300 vs. 2500, respectively), and somewhat shorter than that of tropicamide, in agreement with soft drug design principles. The activities of 2R1'S3'R-GA (the most active zwitterionic isomer) and glycopyrrolate lasted for 10 h and 144 h, respectively, as displayed in FIG. 5. These results indicate that a good pharmacological effect can be achieved by some 2R zwitterionic isomers, and these isomers can be rapidly eliminated from the body. Furthermore, the active 2R zwitterionic isomers did not cause any observable irritation reactions, such as eye-closing, lacrimation, mucous discharge as well as change in the intraocular pressure during the topical applications; and unlike other conventional anticholinergics, these 2R zwitterionic isomers did not induce dilation of the pupil in the contralateral (water-treated) eyes, indicating no or low systemic side-effects. Therefore, these soft drugs are safe, promising short acting anticholinergics with the possibility of largely reduced unwanted side effects.

Conclusion

Isomers of N-substituted soft anticholinergics based on glycopyrrolate, the methyl and ethyl esters, and their zwitterionic metabolite were synthesized and separated. Their pharmacological activities were evaluated in vitro and in vivo. The receptor binding (pK$_i$) results indicate that stereo-specificity and stereo-selectivity are very important in these soft anticholinergics. There were three chiral centers presented in the structure of these compounds. The most significant improvement of the receptor binding activity was observed in 2R configuration, followed by 1'S. The activities of 3'R and 3'S could be affected by the configurations of the other two chiral centers. The improvement of M$_3$1M$_2$ muscarinic-receptor subtype-selectivity was found most significant in 2R3'S configurations followed by 2R3R. The configuration of chiral center 1' showed no effect on M$_3$/M$_2$ muscarinic-receptor subtype-selectivity. Comparable results obtained from guinea pig ileum assays (pA$_2$), and rabbit mydriasis test on zwitterionic isomers further confirmed the stereo-specificity of these anticholinergics. The pharmacological potency of eight zwitterionic isomers was determined to be 2R1'S3'S=2R1'S3'R=2R1'R3'S>2R1'R3'R>2S1'S3'R>2S1'S3'S=2S1'R3'R>2S1'R3'S (student t-test, p<0.05). When topically administered (0.1%) in rabbit eyes, some 2R-zwitterion isomers (2R1'S3'S, 2R1'S3'R and 2R1'R3'S) showed similar mydriatic potencies to that of glycopyrrolate and tropicamide, however, their mydriatic effects were of considerably shorter duration, and they did not induce dilation of the pupil in the contralateral, water-treated eyes, indicating that, in agreement with their soft nature, they are locally active, but safe and have a low potential to cause systemic side effects. The usefulness and safety of these glycopyrrolate-based soft anticholinergics have been therefore further proved.

Further Synthesis and Biological Testing

A series of pure stereoisomeric soft glycopyrrolate analogues 3, 4 and 5 below was synthesized by using chiral intermediates and by careful separation of the stereoisomers formed during the last quaternization step of the synthesis. The stereochemistry of the products was elucidated by using various 1D and 2D NMR techniques. Anticholinergic activity of the new compounds was determined by receptor binding studies and further by performing tests on isolated organs and by in vivo tests. Receptor binding revealed that in the higher alkyl ester series the (2R,1'R,3'R) and the (2R,1'S,3'S) isomers were the compounds showing the highest receptor affinity; furthermore, it demonstrated the confines of the length of the alkyl chain. In vitro isolated organ experiments correlated well with the receptor binding results, and in vivo investigations indicated the soft character of the compounds.

One of the most effective anticholinergic compounds is glycopyrrolate [3-(2-cyclopentyl-2-phenyl-2-hydroxyacetoxy)-1,1-dimethylpyrrolidinium bromide, 1 below] containing a quaternary N-atom the charge of which prevents its crossing through lipid membranes and therefore, compared to e.g atropine, glycopyrrolate has reduced CNS-related side effects. The molecule contains two chiral centers: at position 2 of the acyl group and at position 3' of the pyrrolidinyloxy moiety and hence this compound can exist in the form of the four stereoisomers (2R,3'R), (2R,3'S), (2S,3'R), (2S,3'S). The marketed drug is a mixture of stereoisomers while the (2R, 3'R) form is known as Ritropirronium bromide.

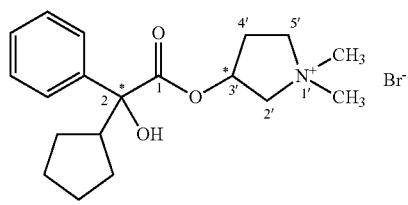

Glycopyrrolate

Soft analogues of glycopyrrolate such as compounds of formulas 2, 3 and 6 below containing three chiral centers (in addition to the two centers in the parent molecule the quaternary nitrogen bearing two different substituents is also asymmetric) have also been described above and have been shown to possess the expected soft character. This has been reflected by the relatively short duration of action and low systemic side effects. In addition, it has been shown above that enzymatic hydrolysis of the esters 2 and 3 yielded the corresponding zwitterionic acid 6 which is much less active in rats and is rapidly eliminated. The initially prepared soft analogues were either mixtures of all possible eight stereoisomers or mixtures of four stereoisomers containing the (R)-form of the cyclopentylmandeloyl unit while the remaining two chiral centers were in racemic forms.

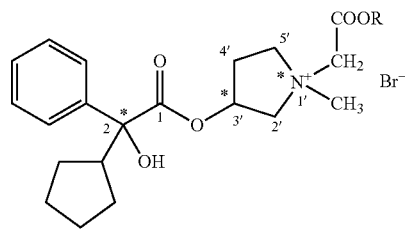

Soft analogues of Glycopyrrolate

| | R |
|---|---|
| 2 | methyl |
| 3 | ethyl |
| 4 | n-hexyl |
| 5 | n-octyl |
| 6 | H |

Considering the favorable biological test results of compounds 2 and 3 the question emerged whether any of the pure stereoisomers could have any advantage over the others or not. Therefore, the aim of the present work was to synthesize and test pure stereoisomers of the soft glycopyrrolate analogues 3, 4 and 5 and at the same time to study the influence of higher alkyl groups as R upon the extent and time course of anticholinergic activity. Thus, the primary target molecules were the pure stereoisomers of the hexyl esters 4 and octyl esters 5 with the proviso that the configuration of C-2 in the cyclopentylmandeloyl unit was fixed as (R) since literature data showed (R)-cyclopentylmandeloyl derivatives to be more active anticholinergics than their (S)-counterparts. This meant that only two chiral centers (N-1' and C-3' in the pyrrolidinyloxy moiety) and consequently only four stereoisomers had to be taken into consideration. In addition, for comparison, analogous pure stereoisomers of the ethyl esters 3 were also synthesized, Synthesis of the Pure Stereoisomers The target compounds were prepared by quaternization of the key intermediates 10 (see Scheme 4) with the bromoacetates 11, 12 and 13, respectively, wherein 10 was used either as a mixture of the (2R,3'S) and (2R,3'R) diastereomers (Method A) or as the individual diastereomers (Method B).

The diastereomeric mixture of compound 10 was prepared first by the known transesterification of (R)-methyl cyclopentylmandelate (8) with racemic 1-methyl-3-pyrrolidinol [(R, S)-(9)]. Later it was found that much higher yield could be reached by direct coupling of (R)-cyclopentylmandelic acid (7) with (R,S)-(9) under Mitsunobu conditions. On the other hand, the individual diastereomers of 10 were obtained via two different routes. Thus, transesterification of (R)-methyl cyclopentylmandelate (8) with (S)-1-methyl-3-pyrrolidinol [(S)-(9)] as above proceeded with retention of configuration at C-3' and yielded (2R,3'S)-10, On the other hand, direct coupling of (R)-cyclopentylmandelic acid (7) with the same (S)-(9) under Mitsunobu conditions (with inversion of configuration at C-3') led to (2R,3'R)-10.

Scheme 4 Synthetic route to compounds 3-5

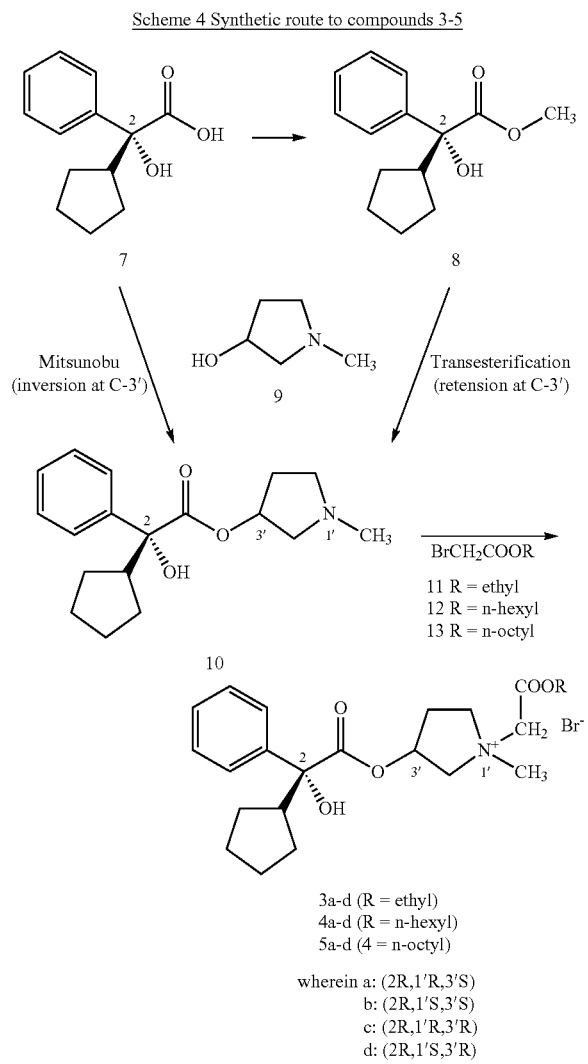

3a-d (R = ethyl)
4a-d (R = n-hexyl)
5a-d (4 = n-octyl)

wherein a: (2R,1'R,3'S)
b: (2R,1'S,3'S)
c: (2R,1'R,3'R)
d: (2R,1'S,3'R)

Next, in Method A, quaternization of the mixture of (2R, 3'S)-10 and (2R,3'R)-10 with the bromoacetates 12 and 13, respectively, giving rise to the formation of a new chiral center at N-1', led to mixtures of the four stereoisomeric target compounds 4a-d and 5a-d, respectively. The individual stereoisomers could be separated only partially by a combination of various chromatographic and crystallization methods (see Experimental below).

Isolation of the pure stereoisomers was simpler in the other approach: in Method B, quaternization of (2R,3'S)-10 with the bromoacetates 11 and 12, respectively, as above afforded only two stereoisomers, i.e. the (2R,1'R,3'S) and the (2R,1'S, 3'S) versions both of compounds 3 and 4, respectively, and separation of these components was achieved with less difficulty. On the other hand, in full analogy with the abovesaid, the final quaternization starting with (2R,3'R)-10 resulted in the formation of the other pair of isomers, i.e. the (2R,1'R,3'R) and the (2R,1'S,3'R) versions of the final products 3 and 4, respectively. Finally, from among the twelve target compounds (3a-d, 4a-d and 5a-d) two pairs of compounds, i.e. 3a+3b and also further 5a+5d were obtained as inseparable mixtures while all other stereoisomers could be isolated in pure state. Note that 3a-d are also referred to herein as Compounds (k), (l), (m) and (n), respectively; 4a-d are also referred to herein as Compounds (o), (p), (q) and (r), respectively; and 5a-d are also referred to herein as Compounds (s), (t), (u) and (v), respectively.

Structure Elucidation and Assignment of Stereochemistry

The structures and stereochemistry of the new target compounds were elucidated by detailed NMR studies and the purity of the samples was confirmed by HPLC. The assignment of the individual stereoisomers is illustrated below using the example of the four isomeric hexyl esters 4a-d. A complete $^1$H and $^{13}$C NMR signal assignment was achieved by applying $^1$H, $^{13}$C, DEPT, and two-dimensional $^1$H—COSY, $^1$H, $^1$H-TOCSY and $^1$H, $^{13}$C—HSQC correlation experiments. The characteristic $^1$H and $^{13}$C chemicals shifts are compiled in Table 7. Due to the high similarity of the chemical shifts of the isomers 4a-d, a simple differentiation of the structures was not possible, only the $^+$NCH$_3$ and $^+$NCH$_2$COOR chemical shifts exhibited characteristic differences. To reveal the stereochemistry, one-dimensional selective NOESY, two-dimensional ROESY and NOESY spectra were run, affording evidences of interprotonic distances less than 5 Å. The double arrows in Scheme 5 denote the detected relevant NOE $^1$H/$^1$H steric proximities.

TABLE 7

Characteristic $^1$H and $^{13}$C chemical shifts of isomers 4a-d in CDCl$_3$.

| | 4a [(o)] 2R, 1'R, 3'S | | 4b [(p)] 2R, 1'S, 3'S | | 4c [(q)] 2R, 1'R, 3'R | | 4d [(r)] 2R, 1'S, 3'R | |
|---|---|---|---|---|---|---|---|---|
| | $^1$H | $^{13}$C | $^1$H | $^{13}$C | $^1$H | $^{13}$C | $^1$H | $^{13}$C |
| 1 | — | 174.5 | — | 174.6 | — | 174.6 | — | 174.5 |
| 2 | — | 79.8 | — | 79.7 | — | 79.4 | — | 79.8 |
| 2'$_{cis}$ | 4.36 | 70.3 | 4.16 | 68.9 | 3.91 | 70.0 | 4.20 | 70.5 |
| 2'$_{trans}$ | 4.46 | | 4.68 | | 4.55 | | 4.38 | |
| 3' | 5.52 | 73.1 | 5.57 | 73.4 | 5.55 | 73.3 | 5.53 | 73.1 |
| 4'$_{cis}$ | 2.06 | 31.5 | 1.96 | 30.1 | 2.24 | 29.6 | 2.25 | 30.1 |
| 4'$_{trans}$ | 2.79 | | 2.93 | | 3.05 | | 2.88 | |
| 5'$_{cis}$ | 4.08 | 65.0 | 4.03 | 65.1 | 4.17 | 65.1 | 4.20 | 65.3 |
| 5'$_{trans}$ | 4.18 | | 4.39 | | 4.44 | | 4.34 | |
| NCH$_3$ $_{cis}$ | — | | 3.24 | 50.7 | 3.03 | 50.6 | — | |
| NCH$_3$ $_{trans}$ | 3.69 | 51.9 | — | | — | | 3.69 | 51.9 |
| NCH$_2$ $_{cis}$ | 4.74; 4.86 | 62.8 | — | | — | | 4.52; 4.69 | 62.9 |
| NCH$_2$ $_{trans}$ | — | | 5.16; 5.20 | 63.8 | 5.08; 5.19 | 63.7 | — | |
| Ph$_{ipso}$ | | 141.4 | | 141.1 | | 140.8 | | 141.2 |
| Ph$_{ortho}$ | 7.59 | 126.1 | 7.57 | 126.0 | 7.58 | 126.0 | 7.59 | 126.0 |
| Ph$_{meta}$ | 7.34 | 128.5 | 7.36 | 128.6 | 7.37 | 128.6 | 7.36 | 128.6 |
| Ph$_{para}$ | 7.27 | 128.2 | 7.30 | 128.2 | 7.27 | 128.0 | 7.27 | 128.0 |
| HC—C-2 | 2.87 | 46.8 | 2.96 | 46.1 | 2.93 | 45.6 | 2.89 | 46.8 |

Scheme 5 Stereochemistry of isomers 4a-d [Cpds (o), (p), (q) and (r), respectively]

4a:

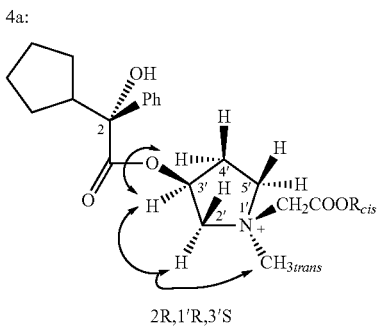

2R,1'R,3'S

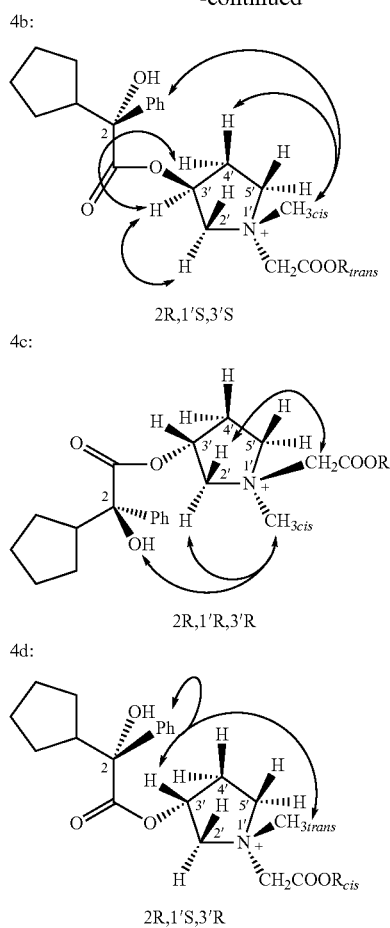

Selective irradiation of the $^+NCH_3$ signal in 4b resulted in NOE intensity enhancement at the and at the ortho hydrogen signals, which unambiguously proved the 1'S configuration and at the same time, the depicted preferred conformation of the 0-acyl moiety. Irradiation of the $NCH_3$ signal in 4a marked out only the hydrogen atom $H_{trans}$-2', located on the same side of the pyrrolidine ring. In the case of compound 4d, the appearance of a strong $^+NCH_3/H$-3' cross peak in the ROESY spectrum gave evidence of the 1'S configuration, whereas the H-3'/$H_{ortho}$ response revealed the conformation of the O-acyl group.

In compound 4c due to the unfavourable signal overlapping (e.g. $^+NCH_3$ and H-4'$_{trans}$), the two-dimensional measurement does not work. Here, the one-dimensional selective NOESY was utilized again. Irradiating the $H_{ortho}$ hydrogen atoms a small, but significant NOE was observed at the $^+NCH_3$ signal, which is in accordance with the depicted configuration and conformation.

Due to the pseudorotation of the pyrrolidine ring and the high flexibility of the compounds 4a-d, conformational averaged structures are expected. Despite this, the anomalous upheld shift of the $^+NH_3$ signals (3.24 and 3.03 ppm) can be explained by the well known anisotropic shielding effect of the aromatic ring, wherein the hydrogen atoms located above the plane of the aromatic ring show smaller chemical shifts. The smaller chemical shifts of the $NCH_2$ (cis) hydrogens in 4a (4.74; 4.86) and 4d (4.52; 4.69) are in accord with the relative steric arrangement. Preference of the conformations of compounds 4a-d, where the aromatic ring is oriented towards the nitrogen atom, is in accord with the stabilization of the positive charge on the nitrogen by the n-system of the phenyl group.

Biology: Evaluation of the Anticholinergic Activity

Receptor Binding

Evaluation of the affinity of the soft glycopyrrolate analogues 3a-d, 4a-d and 5a-d above for muscarinic receptors was carried out using [$^3$H]QNB as ligand and rat cortical membrane preparation as a source of the receptor. The affinity (summarized in Table 8) of these compounds for the muscarinic receptors (mainly $M_1$ in this preparation) was found one or two orders of magnitude lower than those of the reference compounds glycopyrrolate (Ki=0.8 nM) and atropine (Ki=1.9 nM) but the instant compounds were still strong antagonists of the muscarinic receptor, The nature of the interaction was characterized by the steep Hill slope, the value of which was close to unity indicating the antagonistic action. The difference between the effects of the pure stereoisomers was seen most clearly within the hexyl series as in this case all the four possible stereoisomers were isolated in pure state. The compounds 4b (2R,1'S,3'S) and 4c (2R,1'R, 3'R) were equally, approximately four-fold, more active than 4a (2R,1'R,3'S) or 4d (2R,1'S,3'R). The same tendency was clear in case of the less active octyl series (5b, 5c), even though the other two isomers (5a+5d) were tested as a mixture. The above (2R,1'S,3'S) and (2R,1'R,3'R) compounds contain the larger quaternizing group ($CH_2COOR$) in trans position to the cyclopentylmandeloyloxy moiety and this fact suggests that the sterically less crowded nature of these isomers may contribute to the higher receptor affinity, in contrast with the sterically more crowded cis isomers.

TABLE 8

Receptor binding strength of the glycopyrrolate analogues

| Compound | Ki (nM), Average ± SD | Hill slope |
|---|---|---|
| 3a + 3b [(k) + (l)] | 65 ± 8 | −0.96 ± 0.09 |
| 3c [(m)] | 16 ± 1 | −0.93 ± 0.08 |
| 3d [(n)] | 16 ± 1 | −1.07 ± 0.02 |
| 4a [(o)] | 67 ± 9 | −1.22 ± 0.08 |
| 4b [(p)] | 13 ± 1 | −1.19 ± 0.05 |
| 4c [(q)] | 15 ± 1 | −1.24 ± 0.04 |
| 4d [(r)] | 58 ± 5 | −1.15 ± 0.05 |
| 5a + 5d [(s) + (v)] | 303 ± 7 | −1.20 ± 0.08 |
| 5b [(t)] | 60 ± 5 | −1.22 ± 0.11 |
| 5c [(u)] | 68 ± 6 | −1.26 ± 0.06 |

On the other hand, in the ethyl ester series the isomers 3c (2R,1'R,3'R) and 3d (2R,1'S,3'R), i.e. the compounds wherein the cyclopentylmandeloyloxy moiety is attached to the pyrrolidine ring in the α-position, have higher affinity indicating that in this case the steric position of the smaller $CH_2COOEt$ group has less influence upon receptor affinity.

The effect of the length of the alkyl chain in the ester group upon the receptor binding seemed to be negligible up to 6 carbon moiety but when the longer chain was used this already affected receptor binding (compare the whole hexyl and octyl series).

Ex Vivo Experiments with Isolated Organs

Determination of the $pA_2$ values in guinea pig trachea and ileum assay resulted in the expected results. In line with the receptor binding experiments in both of the isolated organ preparations, atropine and glycopyrrolate were more active (Table 9) than the instant selected glycopyrrolate analogues chosen to represent compounds with markedly different receptor affinities. The ethyl and hexyl side chain containing compounds (3c and 4b) were practically equally effective while the octyl chain containing esters showed weaker activity.

TABLE 9 pA$_2$ values in two types of isolated organ experiments*

| Antagonist | Trachea | | Ileum | |
|---|---|---|---|---|
| | pA$_2$ | Slope ± S.E. | pA$_2$ | Slope ± S.E. |
| Atropine | 8.85 | 0.98 ± 0.02$^a$ | 8.52 | 0.96 ± 0.30$^a$ |
| Glycopyrrolate | 9.43 | 1.53 ± 0.07$^a$ | 9.66 | 1.03 ± 0.37$^a$ |
| 3c [(m)] | 8.12 | 1.54 ± 0.18$^a$ | 8.48 | 0.76 ± 0.08$^a$ |
| 4b [(p)] | 8.21 | 1.14 ± 0.10$^a$ | 8.14 | 1.31 ± 0.67$^a$ |
| 5a + 5d [(s) + (v)] | 7.23 | 0.79 ± 0.07 | 6.64 | 1.03 ± 0.37$^a$ |

*data are presented of mean estimates in tissue samples from four animals
$^a$deviation from unity is not significant (P > 0.05)

In Vivo Experiments
Carbachol Induced Bradycardia in the Rat

Figure 6:
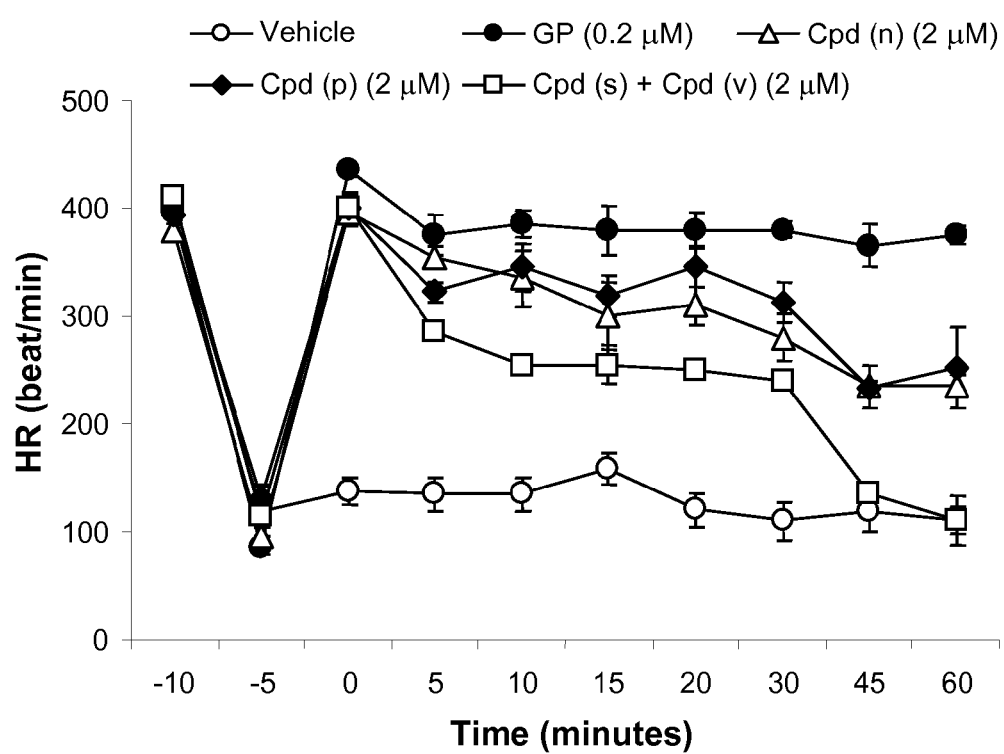
FIG. 6 is a graph of the heart rate in beats per minute versus time in minutes showing the protection effect of different anticholinergics on carbachol-induced bradycardia in anesthetized rats (mean±SD; n=3-5), including ethyl, n-hexyl and n-octyl esters.

The bradycardia protective effect of the selected new compounds was comparable both to their receptor binding affinity and their activity in the isolated organ experiments, In line with this, their in vivo activity (FIG. 6) was lower than that of glycopyrrolate (GP) but more importantly their duration of action was notably shorter than that of the parent compound, indicating their potential soft character.

Experimental
Chemistry

Melting points were determined on a Boetius microscope and are uncorrected. Purity of the compounds was tested on TLC plates (silica gel, Merck). The spots were visualized under UV light and/or by exposure to iodine vapours. NMR spectra were recorded in CDCl$_3$, DMSO-d$_6$ or CD$_3$OD solutions using a Bruker Avarice 500 spectrometer, operating at 500/125 MHz ($^1$H/$^{13}$C). Chemical shifts are given on the δ-scale and were referenced to TMS. Pulse programs for the 1D and 2D NMR experiments were taken from the Bruker software library. For structure elucidation and NMR signal assignment $^1$H, $^{13}$C, DEPT-135, selective 1D-NOESY, $^1$H,$^1$H—COSY, $^1$H,$^1$H-TOCSY, $^1$H,$^{13}$C—HSQC, $^1$H,$^{13}$C-$^1$HMBC, $^1$H,$^1$H—ROESY and $^1$H,$^1$H—NOESY spectra were recorded.

Analytical HPLC of compounds 3, 4 and 5 was performed using a Waters (Milford, Mass.) HPLC system consisting of a model 510 isocratic pump working at 1 ml/min flow rate, a WISP programmable autoinjector with 10 μl injection volume and a model 486 single channel variable wavelength UV detector with 220 nm preset wavelength. The applied HPLC stationary phase was a Prontosil 120 C18 AQ 5 μm column with 150*4 mm geometry. Column temperature: 40° C. The optimal mobile phase was a mixture of 30 mM ammonium acetate/MeOH/acetonitrile, in a ratio of 55/17.5/27.5 (v/v/v) for compounds 3, in a ratio of 34/16/55 (v/v/v) for compounds 4 and in a ratio of 18/20/60 (v/v/v) for compounds 5. The enantiomeric purity of 2-cyclopentylmandelic acid (7) was determined by chiral ligand exchange chromatography on a Nucleosil Chiral-15 μM, 250*4 mm chiral HPLC column. The mobile phase was 0.5 mM CuSO$_4$/acetonitrile 97/3 (v/v), flow rate: 1 nil/min, column temperature: 60° C., detection wavelength: 220 nm. The retention time of the individual enantiomers was 13.5 min (R) and 15.5 min (S), respectively. The observed selectivity was 1.18.

(R)-2-Cyclopentylmandelic acid [(R)-(7)] was obtained by resolution of the racemic acid with (−)-cinchonidine, (R)-methyl 2-cyclopentylmandelate [(R)-(8)] was prepared as described in the art while (R,S)- and (S)-1-methyl-3-pyrrolidinol, respectively [(R,S)- and (S)-(9), respectively], were synthesized in two steps starting with (R,S)- and (S)-malic acid, respectively, as previously described. Ethyl bromoacetate (11) was purchased from Aldrich while the homologous n-hexyl (12) and n-octyl bromoacetates (13) were prepared by reaction of the corresponding alcohol with bromoacetyl bromide. Found values of elemental analyses agreed with calculated values within the range of ±1%.

Preparation of the Quaternized Target Compounds 3, 4 and 5
Method A

A mixture of (2R,3'R)-10 and (2R,3'S)-10 (1.0 mM), together with the alkylating agent 12 or 13 (2.0 mM) in acetonitrile (12 ml) was stirred for 2 hours at room temperature. After completion of the reaction, the solvent was evaporated and the products were isolated as given below in the description of the individual compounds.

Method B

A mixture of (2R,3'R)-10 or (2R,3'S)-10 (0.3 mM) and the alkylating agent 11 or 12 (0.6 mM) in acetonitrile (5 ml) was allowed to react and the crude product was isolated as described under Method A above.

(2R,1'R,3'S) 3-(2-Cyclopentyl-2-phenyl-2-hydroxyacetoxy)-1-(ethoxycarbonylmethyl)-1-methylpyrrolidinium bromide (3a) [Compound (k)] and (2R,1'S, 3'S) 3(2-cyclopentyl-2-phenyl-2-hydroxyacetoxyl)-1-ethoxycarbonyloxymethyl)-1-methylpyrrolidinium bromide (3b) [Compound (l)]

Method B above was followed starting with (2R,3'S)-10. The crude product was purified by silica gel chromatography eluting with chloroform-methanol 9:1 and 3a and 3b were isolated as an inseparable mixture. Yield: 54%, mp. 163° C., ratio 3a/3b ($^1$H-NMR): 4:1.

3a NMR (CDCl$_3$) δ 3.68 (3H, s, NCH$_3$), 4.78 d, NCH$_2$), 4.89 (1H, d, NCH$_2$), 5.55 (1H, m, H-3); 3b $^1$H NMR (CDCl$_3$) δ 3.27 (3H, s, NCH$_3$), 5.26 (1H, d, NCH$_2$), 5.30 (1H, d, NCH$_2$), 5.51 (1H, m, H-3).

(2R,1'R,3'R) 3-(2-Cyclopentyl-2-phenyl-2-hydroxyacetoxy)-1-(ethoxycarbonylmethyl)-1-methylpyrrolidinium bromide (3c) [Compound (m)] and (2R,1'S, 3'R) 3-(2-cyclopentyl-2-phenyl-2-hydroxyacetoxy)-1-(ethoxycarbonylmethyl-methylpyrrolidinium bromide (3d) [Compound (n)]

Method B above was followed starting with (2R,3'R)-10 and the products 3c and 3d were separated by silica gel chromatography of the crude product eluting with chloroform-methanol 9:1.

3c: yield: 19%, mp. 98° C., purity (HPLC): 93%.

$^1$H NMR (CDCl$_3$) δ 1.29 (3H, t, CH$_3$CH$_2$O), 2.24 (1H, m, H$_c$-4'), 2.94 (1H, m, HC—C-2), $\overline{3.02}$ (3H, s, NCH$_3$), 3.07 (1H, m, H$_t$-4'), 3.88 (1$\overline{H}$, m, H$_c$-2'), 4.13 (1H, m, H$_c$-5'), 4.23 (2H, q, CH$_3$CH$_2$O), 4.46 (1H, m, H$_t$-5'), 4.56 (1H, m, H$_t$-2'), 5.10 (1H, d, $\overline{NCH_2}$), 5.22 (1H, d, NCH$_2$), 5.56 (1H, m, H-3'), 7.28 (1H, t, Ph$_p$), 7.37 (2H, t, Ph$_m$), 7.58 (2H, d, Ph$_o$).

3d: yield: 28%, mp. 70° C., purity (HPLC): 96%.

$^1$H NMR (CDCl$_3$) δ 1.33 (3H, t, CH$_3$CH$_2$O), 2.24 (1H, m, H$_c$-4'), 3.66 (3H, s, NCH$_3$), 4.65 (1$\overline{H}$, d, NCH$_2$), 4.74 (1H, d, NCH$_2$), 5.54 (1H, m, H-3'), 7.27 (1H, t, Ph$_p$), 7.35 (2H, t, Ph$_m$), 7.59 (2H, d, Ph$_o$).

(2R,1'R,3'S) 3(2-Cyclopentyl-2-phenyl-2-hydroxyacetoxy)-1-(n-hexyloxycarbonylmethyl)-1-methylpyrrolidinium bromide (4a) [Compound (o)] and (2R,1'S,3'S) 3-(2-cyclopentyl-2-phenyl-2-hydroxyacetoxy)-1-(n-hexyloxycarbonylmethyl)-1-methylpyrrolidinium bromide (4b) [Compound (p)]

Method B above was followed starting with (2R,3'S)-10 and the products 4a and 4b were separated by silica gel chromatography of the crude product eluting with chloroform-methanol 9:1.

4a: yield: 18%, mp. 146° C., purity (HPLC): 93%.
4b: yield: 23%, mp. 125-128° C. purity (HPLC): 96%.
For NMR data of 4a-b see above.

(2R,1'R,3'R) 3-(2-Cyclopentyl-2-phenyl-2-hydroxyacetoxy)-1-(n-hexyloxycarbonylmethyl)-1-methylpyrrolidinium bromide (4c) [Compound (q)] and (2R,1'S,3'R) 3-(2-cyclopentyl-2-phenyl-2-hydroxyacetoxy-1-(n-hexyloxycarbonylmethyl)-1-methylpyrrolidinium bromide (4d) [Compound (r)]

Method B above was followed starting with (2R,3'R)-10 and the products 4c and 4d were separated by silica gel chromatography of the crude product eluting with chloroform-methanol 9:1.

4c: yield: 20%, mp, 138° C., purity (HPLC): 98%.
4d: yield: 55%, mp. 116° C., purity (HPLC): 95%.
For NMR data of 4c-d see above.

As an alternative, upon preparing compounds 4a-d by following Method A above, the products 4 h and 4c could be isolated in pure state as described below while 4a and 4d were obtained in the form of an inseparable mixture. Thus, the crude product was triturated with ethyl acetate to give the mixture 4a+4d [Compounds (o) and (r)]; as a solid, yield: 42%. The mother liquor was concentrated to dryness and the residue was purified by column chromatography on silica gel eluting with chloroform-methanol 9:1. Subsequently compounds 4b (yield: 12%) [Compound (p)]; and 4c (yield: 6%) [Compound (q)] were separated by preparative thin layer chromatography developing with chloroform-methanol 9:1.

(2R,1'R,3'S) 3-(2-Cyclopentyl-2-phenyl-2-hydroxyacetoxy)-1-(n-octyloxycarbonylmethyl)-1-methylpyrrolidinium bromide (5a) [Compound (s)], (2R,1'S,3'S) 3-(2-cyclopentyl-2-phenyl-2-hydroxyacetoxy)-1-(n-octyloxycarbonylmethyl)-1-methylpyrrolidinium bromide (5b) [Compound (t)], (2R, 1'R,3'R) 3-(2-Cyclopentyl-2-phenyl-2-hydroxyacetoxy)-1-(n-octyloxycarbonylmethyl)-1-methylpyrrolidinium bromide (5c) [Compound (u)] and (2R,1'S,3'R), 3-(2-cyclopentyl-2-phenyl-2-hydroxyacetoxy)-1-(n-octyloxycarbonylmethyl)-1-methylpyrrolidinium bromide (5d) [Compound (v)]

By following Method A above and purification of the crude product by silica gel column chromatography eluting with chloroform-methanol 9:1 the compounds 5a and 5d [Compound (s) and (v)] were obtained in the form of a mixture inseparable by TLC and HPLC, On the other hand, 5b [Compound (t)] and 5c [Compound (u)] could be separated by a final preparative thin layer chromatography, developing with chloroform-methanol 9:1.

Mixture of 5a and 5d: yield: 47%, ratio 5a/5d ($^1$H-NMR): 1:1.

5a $^1$H NMR (CDCl$_3$) δ 2.10 (1H, m, H$_c$-4'), 3.64 or 3.67 (3H, s, NCH$_3$), 4.71 (1H, d, NCH$_2$), 4.81 (1H, d, NCH$_2$); 5d $^1$H NMR (CDCl$_3$) δ 2.28 (1H, m, H$_c$-4') 3.64 or 3.67 (3H, s, NCH$_3$), 4.54 (1H, d, NCH$_2$), 4.67 (1H, d, NCH$_2$).

5b: yield: 10%, mp. 30° C., purity (HPLC): 86%.
$^1$H NMR (CDCl$_3$) δ 0.90 (3H, t, CH$_3$CH$_2$), 2.00 (1H, m, H$_c$-4'), 2.93 (1H, m, HC—C-2 and 1$\overline{H}$, m, H$_t$-4'), 3.27 (3H, s, NCH$_3$), 4.10 (1H, m, $\overline{H_c}$-5'), 4.18 (2H, t, CH$_3$CH$_2$), 4.18 (1H, m, H$_c$-2'), 4.29 (1H, m, H$_t$-5'), 4.58 (1H, m, $\overline{H_t}$-2'), 5.16 (2H, s, br, NCH$_2$), 5.56 (1H, m, H-3'), 7.27 (1H, t, Ph$_p$), 7.35 (2H, t, Ph$_m$), 7.57 (2H, d, Ph$_o$).

5c: yield: 7.5%, purity (HPLC): 93%.
5c $^1$H NMR (CDCl$_3$) δ 0.89 (3H, t, CH$_3$CH$_2$), 2.28 (1H, m, 1H$_c$-4'), 2.93 (1H, m, HC—C-2), 2.$\overline{53}$ (3H, s, NCH$_3$), 3.05 (1H, m, 3.86 (1H, m, $\overline{H_c}$-2'), 4.12 (1H, m, H$_c$-5') 4.16 (2H, t, CH$_3$CH$_2$), 4.30 (1H, m, H$_t$-5'), 4.50 (1H, m, H$_t$-2'), 4.97 (1H, d, N$\overline{CH}_2$), 5.10 (1H, d, NCH$_2$), 5.58 (1H, m, H-3'), 7.27 (1H, t, Ph$_p$), 7.38 (2H, t, Ph$_m$), 7.59 (2H, d, Ph$_o$).

Mixture of (2R,3'R) and (2R,3'S) 3-(2-Cyclopentyl-2-phenyl-2-hydroxracetoxy)-1-methylpyrrolidine [(2R,3'R)-10 and (2R,3'S)-10]

A solution of diisopropyl azodicarboxylate (1.5 mM) in tetrahydrofuran (1 ml) was added dropwise to a mixture of (R)-7 (1.5 mM), (R,S)-9 (1.64 mM) and triphenylphosphine (1.5 mM) in tetrahydrofuran (4 ml) at room temperature. The reaction mixture was stirred at room temperature for 2 hours and the solvent was removed in vacuo. The residue was suspended in ethyl acetate and extracted with 1N hydrochloric acid. The aqueous solution was made alkaline with 5N aqueous sodium hydroxide, followed by extraction with ether. The organic layer was dried over magnesium sulfate and concentrated in vacuo giving the title compound as a colorless oil, Yield: 87%, purity (HPLC): 97% (total area of two unresolved peaks).

1:1 mixture of (2R,3'R)-10 and (2R,3'S)-10:
$^1$H NMR (CDCl$_3$) δ 2.35 and 2.39 (3H, s, NCH$_3$), 2.56 and 2.68 (1H, m, H$_c$-2'), 2.94 (1H, m, HC—C-2), 3.75 (1H, s, HO—C-2), 5.24 (1H, m, 11-3), 7.27$\overline{(1H}$, t, Ph$_p$), 7.36 (2H, t, $\overline{Ph}_m$), 7.67 (2H, d, Ph$_o$).

(2R,3'S) 3-(2-Cyclopentyl-2-phenyl-2-hydroxyacetoxy)-1-methylpyrrolidine

The methyl ester (R)-(8) was submitted to transesterification with (S)-9 by following the known method of Franko and Lunsford. Yield: 28%, purity (HPLC): 97%.
$^1$H NMR (CDCl$_3$) δ 2.39 (3H, s, NCH$_3$), 2.68 (1H, m, H$_c$-2'), 2.94 (1H, m, HC—C-2), 3.79 (1H, s, br, HO—C-2), 5.24 (1H, m, H-3'), 7.$\overline{27}$ (1H, t, Ph$_p$), 7.35 (2H, t, $\overline{Ph}_m$), 7.67 (2H, d, Ph$_o$).

(2R,3'R) 3-(2-Cyclopentyl-2-phenyl-2-hydroxyacetoxy)-1-methylpyrrolidine (2R,3'R)-10

(R)-(7) was coupled with (S)-9 under Mitsunobu conditions as described above under 3.1.1.7. Yield: 49%, purity (HPLC): 95%.
$^1$H NMR (CDCl$_3$) δ 2.34 (3H, s, NCH$_3$), 2.93 (1H, m, HC—C-2), 3.78 (1H, m, HO—C-2), 5.23 (1H, m, H-3'), 7.27 $\overline{(1H}$, t, Ph$_p$), 7.34 (2H, t, $\overline{Ph}_m$), 7.67 (2H, d, Ph$_o$).

Biology: Test Methods
Receptor Binding Assay

The binding of [$^3$H]quinuclidinyl benzylate ([$^3$H]QNB; Amersham, 42.0 Ci/mmol) to muscarinic receptors was measured according to the method of Yamamura and Snyder (1974), with some modifications, as described previously by Barlocco et al. (1997). Briefly, male Sprague-Dawley rats (180-220 g) were decapitated and cerebral cortices removed, discarding the white matter. Pooled tissue was homogenized in 10 volumes of ice-cold 50 mM Tris-HCl buffer (pH 7.4) by using a motor driven glass homogenizer. The homogenate was centrifuged at 4° C. and 30,000 g for 10 mm. The pellet was washed twice with the same butler by resuspension, followed by centrifugation at 4° C. and 30,000 g for 10 min. The final pellet was resuspended in 10 volumes of Tris-HCl buffer and stored at −20° C. before use. Protein content was determined by the method of Bradford (1976) using bovine serum albumin as the standard.

In all binding experiments, membranes (0.25 mg/ml protein), radioligand and competing drugs were incubated in a final volume of 1 ml of 50 mM Tris-HCl buffer (pH 7.4) for 60 min at 25° C. For saturation studies, membranes were incubated with 0.01-2 nM [$^3$H]QNB. In competition experiments, the final concentration of the radioligand was 0.2 nM and competing drugs were given in S concentrations. Non-specific binding was determined with 1 µM atropine. The incubation was terminated by rapid vacuum filtration over Whatman GF/B filters using a Brandel Cell Harvester. Samples were washed immediately with 3×4 ml ice-cold Tris-HCl buffer and placed in 6 ml scintillation fluid. Radioactivity was estimated by liquid scintillation counting.

Data are the mean±S.E.M. of at least three experiments run in duplicate. GraphPad Prism 3.0 (GraphPad Software Inc., San Diego, Calif., USA) was used to perform linear and non-linear regression analysis of the data. Saturation binding parameters ($K_d$ and $B_{max}$) were determined by linear regression analysis of the transformed saturation binding data. Competition binding isotherms were analyzed by non-linear regression to derive estimates of the $IC_{50}$ values and Hills slopes. $IC_{50}$ values were converted to $K_i$ values according to the equation of Cheng and Prusoff (1973).

Guinea Pig Trachea and Ileum Assay (pA$_2$ Value Determination)

Tracheal preparations were made as described previously in details by Preuss and Goldie (1999). Briefly: tracheas were isolated from male Dunkin-Hartley guinea pigs (280-300 g) and the ring preparations (2-3 mm in width) were suspended under 500 me resting tension in an organ bath containing Krebs' bicarbonate buffer aerated with 95% $O_2$/5% $CO_2$. Changes in isometric tension were measured by a force displacement transducer (Experimetria, Budapest, Hungary) coupled to a Watanabe recorder. Cumulative concentration-effect curves were constructed to carbachol in the absence or presence of the antagonists. In each animal two preparations were used as time control (i.e., repeated carbachol curves in the absence of any antagonist) the remaining two preparations were used to test responses in the presence of two different concentrations of the antagonist.

Antagonists were added to the organ bath 30 min prior to commencement of the agonist concentration versus effect curves. Schild plots were constructed for the antagonists against carbachol and pA$_2$ values as well as slope estimates were obtained.

The ileum longitudinal muscle strips with adhering myenteric plexus were also prepared from male guinea-pigs (200-400 g). A segment of small intestine (8-10 cm) 10 cm proximal to the ileo-coecal valve was dissected. The longitudinal muscle strip was obtained by mounting segments of the whole ilea on a 1 ml pipette and gently tearing away the outer longitudinal muscle layer with a cotton swab. Longitudinal muscle strips were cut into 3-4 cm pieces. The strips were mounted in an organ bath containing Tyrode solution at 37° C. under a resting tension of 500 mg. Contractions were recorded isometrically with the same strain gauge system as above and registered on the Watanabe type polygraph. The tissues were left to equilibrate for 30 min. Dose-response curves to the agonist were constructed by addition of acetylcholine in increasing concentrations. The doses were given at 10 min intervals with 1 min contact time. After a 40 min equilibration period, the preparations were incubated with the antagonist for 20 min, and a second concentration-response curve to acetylcholine was constructed. The agonist (Ach) was non-cumulatively added at 10 min intervals (concentration range: $10^{-10}$ to $10^{-5}$ M). Antagonists were applied in the concentration range of $10^{-8}$ to $10^{-5}$ M, depending on the individual test compound, Responses were measured as changes in isometric tension and calculated as a percentage of the maximum response attained in the initial concentration-response curve. Determination of antagonist potencies was done by constructing Schild double logarithmic plot of log (DR-1) versus-log M concentrations of the antagonist, and the slope of the plot was computed. If the slopes of the plots were not significantly different from unity, the interaction was accepted as competitive in nature, and antagonist potencies were expressed as pA$_2$ values (Arunlakshana & Schild, 1959). If the slopes of the plots were significantly different from unity, the method of Ariens & Van possum (1957) was used to determine pD' values for characterization of non-competitive antagonism. Statistical significance was assessed by ANOVA followed by Dunnett test.

Antagonistic Effect on Carbachol Induced Bracycardia

The experimental procedure described previously in detail by Juhasz et al. (1998) was followed. Male Sprague-Dawley rats, weighing 300-350 g were anesthetized with sodium pentobarbital (50 mg/kg i.p.). Baseline electrocardiography (ECG) recordings were performed after 15 min stabilization periods. Needle electrodes were inserted subcutaneously into the limbs of the anesthetized rats and were joined to a Watanabe recorder. Recording of the heart rate (1/min) was taken before, during and after the administration of any of the compounds until basic ECG parameters returned to baseline at a paper speed of 25 mm/sec. All drugs were administered by direct injection into the jugular vein. Anticholinergic drugs were administered in the approximate pharmacodynamic equivalent doses (0.2, 2.0 umol/kg) at 0 time, while carbachol (5-8 ug/kg) was injected at −5, 5, 10, 15, 20, 30, 45, 60 min.

Synthesis and Biological Testing of Tiotropium Derivatives
Structure of the Compounds

[Compound (w)]

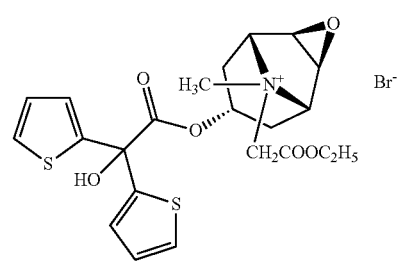

Tiotropium ethyl ester derivative derivative

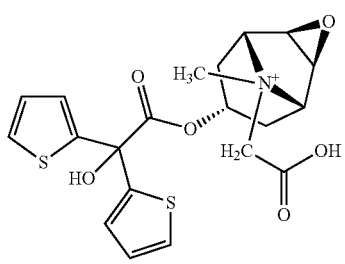

[Compound (aa)]

Tiotropium zwitterion b) Synthesis of a New Tiotropium Analog

By following the inactive metabolite approach, a metabolically sensitive ester function was introduced into the tiotropium molecule resulting in a new soft anticholinergic analog. Intermediate XIII was prepared by the known Grignard reaction of dimethyl oxalate with 2-thienylmagnesium bromide (XII, see Scheme 6 below). Compound XIII was then submitted to known transesterification with scopine (XIV) catalyzed by sodium metal giving the corresponding ester XV. Finally, quaternization with ethyl bromoacetate gave the target compound II (R=Et).

2-Thienylmagnesium bromide was prepared in the usual manner from magnesium and 2-bromothiophene in ether. Scopine (XIV) was obtained from scopolamine hydrobromide by treatment with sodium borohydride in ethanol in moderate yield as described in GB 1,469,781 (1974).

Scheme 6

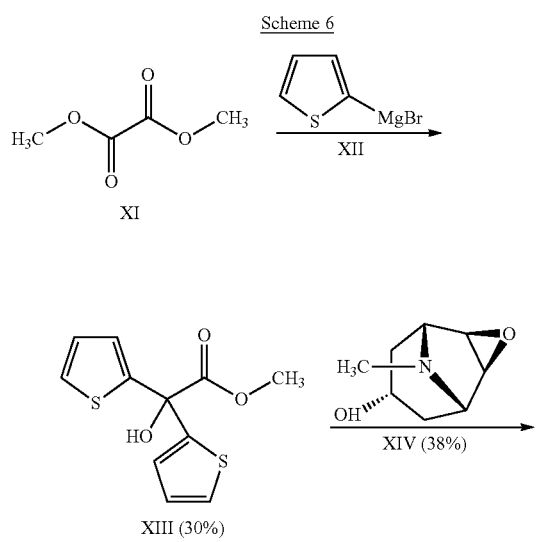

XIII (30%)

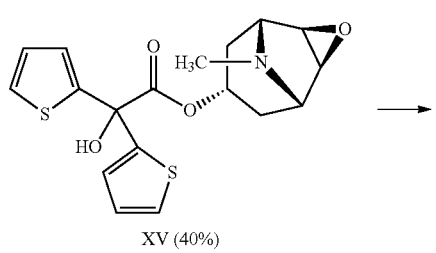

XV (40%)

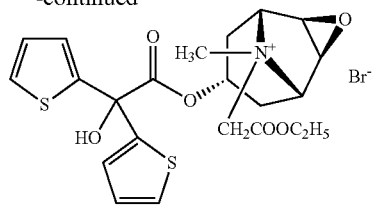

II (R = Et)
(70%)
Compound (w)

The above synthesis of the soil; tiotropium bromide analog leads to a single isomer in a yield of 70%. Tlc indicated no further new component in the reaction mixture of the final quaternisation step and it could be shown by NMR (two dimensional ROESY technique) that the ethoxycarbonylmethyl group is in proximity to the oxirane ring. This finding is somewhat surprising as the other isomer with N-methyl pointing toward the oxirane ring would be sterically less crowded.

Stereochemistry of Compound (w) obtained by two-dimensional ROESY experiment:

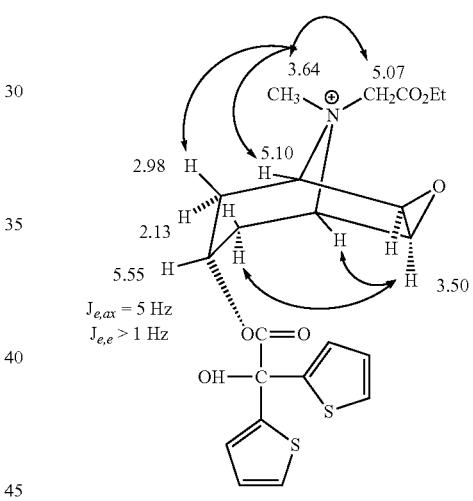

The numbers denote $^1$H chemical shifts and coupling constants, the double arrows indicate steric proximities, Preparation of 6β,7β-epoxy-3β-hydroxy-8-ethoxycarbonylmethyl-8-methyl-1αH,5αH-tropanium bromide, di-2-thienylglycolate, Compound (w)

The scopine ester, represented by formula XV in Scheme 6 above, was prepared as described above, or by conventional methods as described in EP418716 (equivalent to U.S. Pat. No. 5,610,163). Then the scopine ester (70 mg, 0.18 ml) is dissolved in 2 ml of acetone. Ethyl bromocetate (150 microliters, 0.45 mM) is added and the mixture is allowed to react at 20° C. for eight days. The solvent is evaporated in vacuo, 8 ml of water is added and the organic material is extracted with chloroform. The desired quaternary salt is in the aqueous phase and is obtained by lyophilization. Yield 70 mg (70%). Melting point: 115° C. Thin layer chromatography on $Al_2O_3$: $R_f$=0.3($CHCl_3$—$CH_3OH$, 4:1) (3 times 4 ml). The product, Compound (w), has the structural formula II shown in Scheme 6 above.

Preparation of 6β,7β-epoxy-3β-hydroxy-8-methyl-8-(2,2,2-trichloroethoxycarbonylmethyl-1αH, 5αH-tropanium bromide, di-2-thienylglycolate, Compound (x)

To the scopine ester XV (0.5 mM) in 3 ml of anhydrous acetonitrile, 1.5 mM of trichloroethyl bromoacetate was added. The mixture was stirred under argon for three days and the acetonitrile was removed under reduced pressure. To the oily residue, 15 ml of water was added and extracted with chloroform (3 times 5 ml). The aqueous solution was lyophilized to give the product as a white solid. Yield 257 mg (79%). Melting point 105° C., $R_f$=0.65 ($CHCl_3$—$CH_3OH$, 4:1). The product has the structural formula:

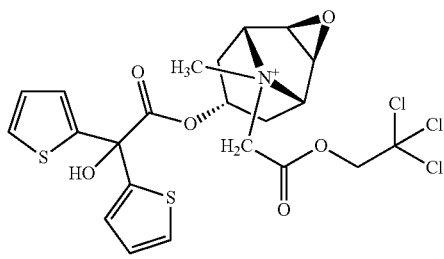 [SMILES: C[N+]1(CC(=O)OCC(Cl)(Cl)Cl)[C@@H]2C[C@@H](OC(=O)C(O)(c3cccs3)c3cccs3)C[C@H]1[C@@H]1O[C@@H]12]

Preparation of 6β,7β-epoxy-3β-hydroxy-8-carboxymethyl-8-methyl-1αH,5αH-tropanuim, di-2-thienylglycolate inner salt, Compound (aa)

A suspension 0.35 mM Compound (x) and Zn dust (0.6 mM) in acetic acid (1.5 ml) was stirred for 3 hours. To that mixture, water (2 ml) and chloroform (2 ml) were added and filtered. The solvents were evaporated in vacuo, 3 ml of water was added and the solution was lyophilized. The crude product was dissolved in methanol (2 ml) and purified by chromatography on Sephadex The resulting oil was dissolved in methanol (2 ml) and precipitated with ethyl acetate (1 ml) to give the solid product, Compound (aa). Yield 67 mg (38%), melting point 158-165° C. (decomp). $R_f$=0.45 ($CHCl_3$—$CH_3OH$ 4:1) on aluminum oxide. The product has the structural formula:

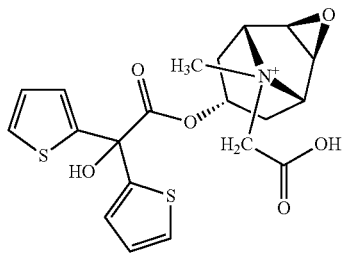 [SMILES: C[N+]1(CC(=O)O)[C@@H]2C[C@@H](OC(=O)C(O)(c3cccs3)c3cccs3)C[C@H]1[C@@H]1O[C@@H]12]

Pharmacology
1: Receptor Binding Assay

Evaluation of the affinity of the compound was made using [$^3$H]QNB as ligand and rat cortical membrane preparation as a source of the receptor. The ethyl ester Compound (w) bound to the muscarinic receptors (mainly $M_1$ in this preparation) with high affinity (Table 10) although this affinity was several-fold lower than those of the reference compounds. The steep Hill slope close to unity indicates the antagonistic nature of its action.

TABLE 10

Affinities of tiotropium ethyl ester derivative [Compound (w)] and reference compounds for muscarinic receptors

| Compounds | $K_i$ (nM) | Hill Slope | Number of exps. |
|---|---|---|---|
| Atropine | 1.9 ± 0.2 | −1.10 ± 0.04 | 4 |
| Glycopyrrolate | 0.8 ± 0.10 | −1.07 ± 0.03 | 4 |
| Compound (w) | 7.2 ± 0.5 | −1.00 ± 0.04 | 4 |

The $K_i$ values are for inhibition of [$^3$H]QNB binding to rat brain cortex membranes.
Values are the mean ± S.E.M. of at least three experiments run in duplicate.

2: Experiments with Isolated Organ

In isolated organ experiments the measurement of antimuscarinic effect of Compound (w) was carried out using guinea pig tracheal ring preparations, where smooth muscle contraction is mediated primarily by muscarinic $M_3$ cholinoceptors although activation of $M_2$-receptors also plays a role in the developing contraction. Compound (w) showed excellent activity in this test; it was more active than atropine and only slightly less effective than ipratropium bromide (Table 11).

TABLE 11

Schild-plot analysis of the antagonism against carbachol in isolated tracheal rings of guinea pigs.

| Antagonist | $pA_2$ | Slope ± S.E. |
|---|---|---|
| atropine | 8.85 | 0.98 ± 0.02[a] |
| ipratropium Br | 9.18 | 1.11 ± 0.14[a] |
| Compound (w) | 8.82 | 1.03 ± 0.08[a] |

Data are presented of mean estimates in tissue from four animals
$pA_2$: the abscissa intercept of the Schild-plot drawn
[a]Indicates slope estimates not significantly different (P > 0.05) from unity.

Figure 7:
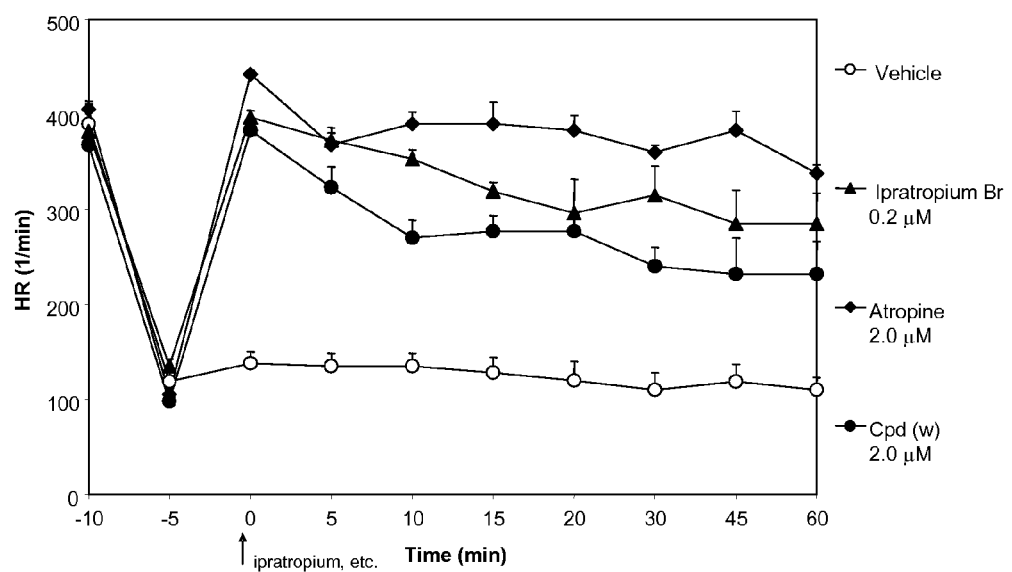
FIG. 7 is a graph of the heart rate in beats per minute versus time in minutes showing the protective effect of different anticholinergics, including Compound (w), on carbachol-induced bradycardia is anesthetized rats (n=3-6).

3. Determination of the Antagonistic Effect of Anticholinergic Agents on Charbachol Induced Bradycardia in Anesthetized Rats Intravenous administration of the cholinomimetic carbachol causes sinus bradycardia (increasing the PP cycle and RR cycle length of the ECG) in anesthetized rats. This effect, which is mediated mainly by muscarinic $M_2$ receptors, can be prevented by prior administration of anticholinergic agent. The bradycardia protective effect of Compound (w) was compared to those of atropine and ipratropium bromide in this system. See FIG. 7. Compound (w) was less active than an equimolar dose of atropine, and was slightly less active than a 10-fold lower dose of ipratropium bromide indicating that Compound (w) may have lower affinity for $M_2$ than $M_1$ or $M_3$ muscarinic receptors. See FIG. 7.

Examination of the Time Course of the Anticholinergic Effect of Compound (w) and Compound (aa) in Electrically Stimulated Guinea Pig Trachea Experimental Procedures:

The procedure described by Takahashi T. et al., (Am J Respir Crit Care Med, 150:1640-1645, 1994) was used with slight modifications.

Male Dunkin-Hartley guinea pigs (300-500 g) were exterminated; the tracheas were rapidly removed, and placed in oxygenated normal Krebs buffer solution. The epithelium was removed and the trachea was spirally cut into 15 mm long strips. Two strips from one animal were prepared and suspended between parallel stainless steel wire field electrodes in 10-ml organ baths containing buffer solution, which was continually gassed by a 95% $O_2$ and 5% $CO_2$ mixture. The tissues were allowed to equilibrate for 1 h with frequent washing, under a resting tension of 1.0 g.

Indomethacin $10^{-5}$(M) was present throughout the studies to block the formation of endogenous prostaglandins. Before the experiment, capsaicin ($10^{-5}$M) was added and washed out 30 min after the pre-treatment to deplete endogenous tachykinins. Tissues were also pretreated with propranolol $10^{-6}$M) 10 min before the experiment to inhibit the effects of endogenous catecholamines.

Isometric contractile responses were measured using force-displacement transducers (Experimetria, Hungary) connected to a Watanabe polygraph. A stimulator (CRS-ST-01-04, Experimetria) provided biphasic square-wave impulses with a supramaximal voltage of 40 V at source and 0.5 ms duration. Stimulations were applied at a frequency of 4 Hz for 15 sec followed by a 100 sec resting interval. After at least four stable responses of equal magnitude were obtained, the antagonist (submaximal dose) was introduced and was left in the system until the maximal effect of the drug was observed. Thereafter the test drug was washed out. Further stimulations were delivered for at least 6 additional hours or until the responses returned to about 50% of the original responses. Appropriate time controls were run in parallel for all studies.

Statistical Analysis

Contractile responses were expressed as the percentage of the own maximal contraction. The time for offset $t_{1/5}$ or $t_{1/2}$ of action was defined as the time from washout of the test antagonist to attainment of 20 or 50% recovery of cholinergic responses.

Figure 8:
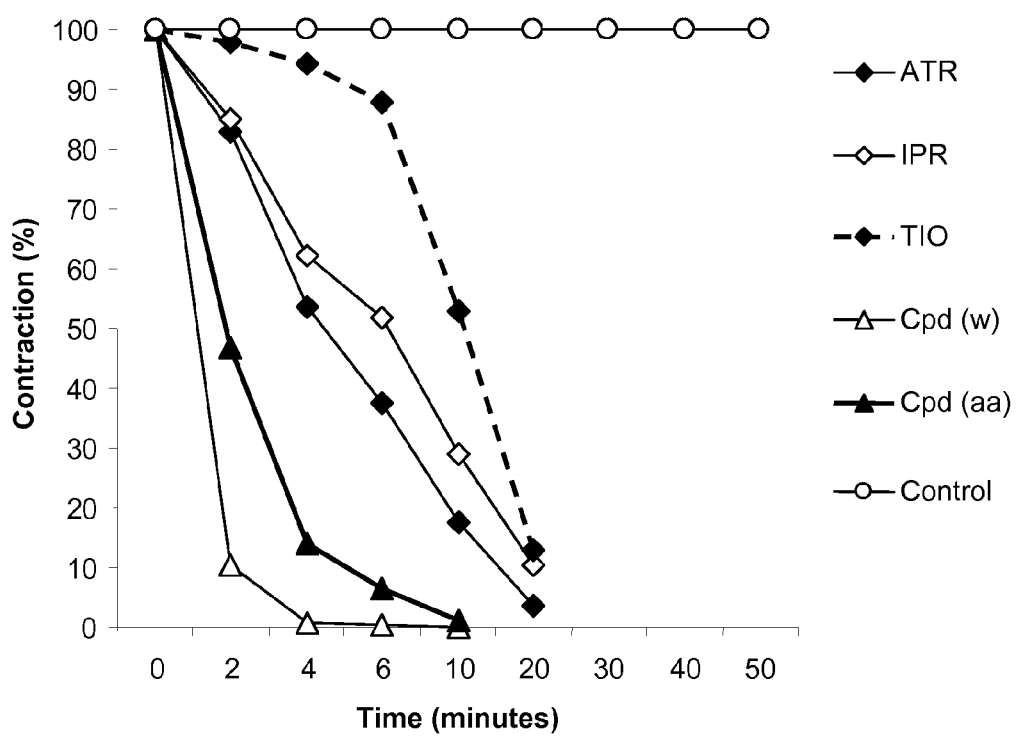
FIG. 8 is a graph showing the time course of action of different anticholinergics, including Compounds (w) and (aa), on electrically stimulated guinea pig trachea.
Figure 9:
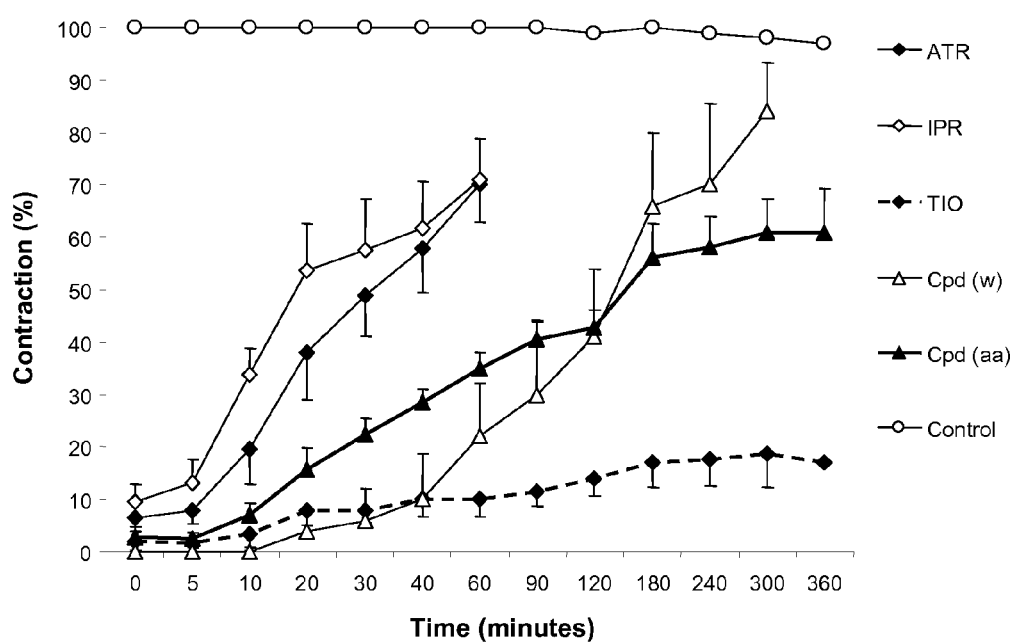
FIG. 9 is a graph showing the time course of the effect of different anticholingerics including Compounds (w) and (aa), after wash out of the test drug on electrically stimulated guinea pig trachea.

Results:

Typical tracings were obtained during the experiments. Continuous, stable, long-lasting contraction is achieved with electrical stimulation. Upon the addition of anticholinergic agents the inhibition develops with varying speed, and the inhibitory effect of the compounds last for very different periods after the washout. In FIG. 8, the time course of action of the different anticholinergic compounds is shown; calculated results are summarized in Table 12, In FIG. 9, the time course of the inhibition of the examined compounds are displayed; the results calculated from this data are summarized in Table 13.

The differences between the on and off rates of the Compounds (w) and (aa) are very notable.

TABLE 12

Time course of action of different anticholinergics
in electrically stimulated guinea pig tracheal strips

| Compound | $t_{1/5}$ onset (min) | $t_{1/2}$ onset (min) |
|---|---|---|
| Atropine | 2.5 | 4.6 |
| Ipratropium Br | 3.0 | 7.0 |
| Tiotropium | 8.0 | 12 |
| Cpd (w) | 0.6 | 1.2 |
| Cpd (aa) | 0.9 | 2.0 |

TABLE 13

Time course of recovery from inhibition after washing
out of different anticholinergics in electrically
stimulated guinea pig tracheal strips

| Compound | $t_{1/5}$ offset (min) | $t_{1/2}$ offset (min) |
|---|---|---|
| Atropine | 10 | 31 |
| Ipratropium Br | 6.5 | 19 |
| Tiotropium | >360 | >360 |
| Cpd (w) | 60 | 130 |
| Cpd (aa) | 27 | 140 |

Investigation of the Anticholinergic Action of Compounds in Acetylcholine Induced Bronchoconstriction in Anesthetized Guinea Pigs Experimental Procedure Male Hartley guinea pigs (320±120 g) (Charles River) were housed under standard conditions. Guinea pigs were anesthetized with urethane (2 g/kg, intraperitoneally), the trachea was cannulated and the animal was respired using a small animal respiratory pump (Harvard Apparatus LTD, Kent UK). Respiratory hack pressure was measured and recorded using a rodent lung function recording system (MUMED, London UK). For drug administration the right jugular vein was cannulated. Following the surgical preparation guinea pigs were allowed to stabilize for 20 minutes. Ten minutes before acetylcholine administration the animals were disconnected from the ventilator and either the vehicle (10 mg lactose) or different amounts of the drug (suspended in the same amount of vehicle) were administered intratracheally. The trachea was reconnected to the ventilator and changes in pulmonary mechanics were followed. Acetylcholine (10 µg/kg) was administered intravenously in every 10 minutes six times.

Results

Figure 10:
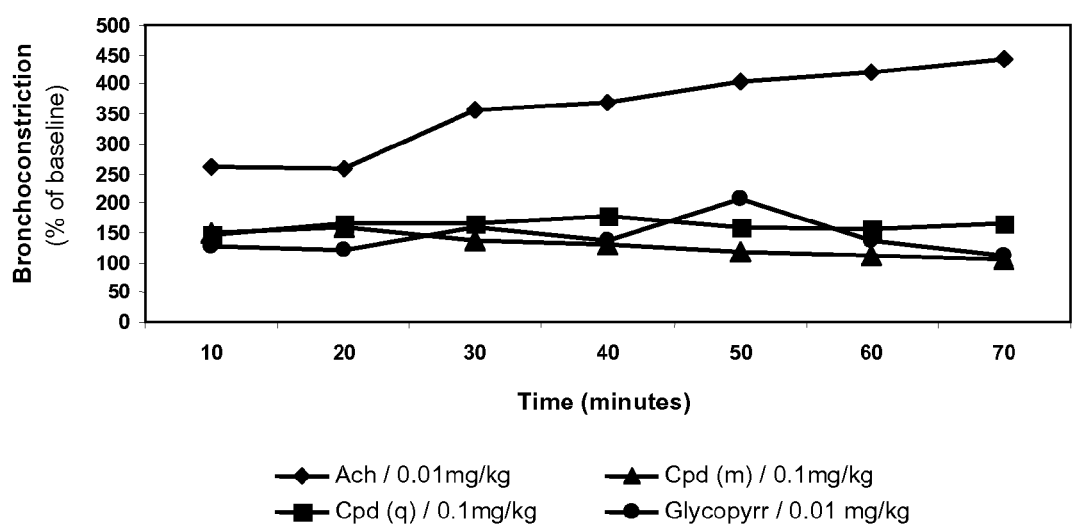
FIG. 10 is a graph of bronchoconstriction (% of baseline) versus time for acetylcholine-induced bronchoconstriction in anesthetized guinea pigs for Compounds (q) and (m) and glycopyrrolate at selected dosages.

Compounds (q) and (m) of the invention and glycopyrrolate all exhibited a protective effect on the acetylcholine-induced bronchoconstriction provoked in this test. Glycopyrrolate was administered at a dose of 0.01 mg/kg, while Compounds (q) and (in) were administered at a dose of 0.1 mg/kg. See FIG. 10.

This test is a model for asthma, chronic obstructive pulmonary disorder and other obstructive respiratory tract disorders in which the effectiveness of the compounds of formulas (Ia) and (Ib) can be evaluated.

Test for Bronchodilatory Effect of inhaled Test Compounds in Balb/c Mice

Female BALB/c mice, weight range 19-22 g, are obtained, for example from Charles River Laboratories (Kingston, N.C.). They receive food and water ad libitum.

Compounds for aerosol administration are prepared in sterile Dulbecco's Phosphate Buffered Saline. Mice are placed in a carousel-style, nose only, exposure chamber and allowed to inhale aerosols for five minutes, using an ICN SPAG-2 nebulizer. This nebulizer generates a mean aerosol particle size of 1.3 microns at a rate of approximately 0.25 ml/minute.

Ten minutes and 36 hours later, the mice are moved to whole body plethysmograph chambers. Bronchoconstriction is induced in the mice by administration of an 80 mg/ml methacholine (MC) aerosol into the plethysmograph chambers for 5 minutes. The mice are allowed to inhale an aerosol containing 80 mg/ml methacholine following inhalation treatment with DPBS vehicle (Dulbecco's Phosphate Buffered Saline), or 80 mg/ml methacholine following inhalation treatment with test compound. The average enhanced pause (Penh, lung resistance), corresponding to airflow resistance, is determined and statistically analyzed using Kruskal-Wallis one way ANOVA. In order to determine the baseline, saline aerosol (without methacholine) is also separately administered to the mice.

This procedure is a model for inhalation treatment of asthma, chronic obstructive pulmonary disorder and other obstructive respiratory tract disorders in which the effectiveness of the compounds of formulas (Ia) or (Ib) can be tested.

Test for Frequency of Micturition in Female Sprague-Dawley Rats

Ten female Sprague-Dawley rats having a mean weight of about 245-285 g are anesthetized with urethane (1.2 g/k, sc.). A midline incision is performed to expose the bladder and a 230 catheter is inserted into the bladder dome for the measurement of intravesical pressure. A non-stop transvesical cystometrogram, as described in *J. Pharmacological. Methods,* 15, pp. 157-167 (1986), is used, at a filling rate of 0.216 ml/min. of saline, to access the filling and voiding characteristics of the bladder. Through the continuous cystometry method thus afforded, consecutive micturition can be recorded. Test compound is given at intravenous doses after the initial baseline micturition sequence is reliably measured for approximately 12 min. From these recordings, the absolute values in maximum pressure obtained and the frequency of micturition is measured. A dose response curve illustrating the effect of test compound on the absolute micturition pressures in the range of 1-50 mg/kg can be obtained. This procedure is a model for overactive bladder (OAB) in which the compounds of the formulas (Ia) and (Ib) can be tested.

The following Examples illustrate numerous formulations suitable for administering the compounds of formula (Ia) and (Ib) to treat various conditions responsive to treatment with an anticholinergic agent. In these Examples, percentages are by weight unless otherwise indicated.

EXAMPLES OF PHARMACEUTICAL FORMULATIONS

Example 1

| Tablets | per tablet |
|---|---|
| Compound of formula (Ia) or (Ib), e.g. Compound (d) or (m) or (w) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

Example 2

| Tablets | per tablet |
|---|---|
| Compound of formula (Ia) or (Ib), e.g. Compound (d) or (m) or (w) | 80 mg |
| lactose | 55 mg |
| corn starch | 190 mg |
| microcrystalline cellulose | 35 mg |
| polyvinylpyrrolidone | 15 mg |
| sodium-caroxymethyl starch | 23 mg |
| magnesium stearate | 2 mg |
| | 400 mg |

The finely ground active substance, some of the corn starch, lactose, microcrystaline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

Example 3

| Ampule solution | |
|---|---|
| Compound of formula (Ia) or (Ib), e.g. Compound (d) or (m) or (w) | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampules which are then sterilized and sealed by fusion. The ampules contain 5 mg, 25 mg and 50 mg of active substance.

Example 4

| Metering aerosol | |
|---|---|
| Compound of formula (Ia) or (Ib), e.g. Compound (d) or (m) or (w) | 0.005 |
| Sorbitan trioleate | 0.1 |
| Monofluorotrichloromethane and difluorodichloromethane | 2:3 ad 100 |

The suspension is transferred into a conventional aerosol container with a metering valve. Preferably, 50 µl of suspension are delivered per spray. The active substance may also be metered in higher doses if desired (e.g. 0.02% by weight).

Example 5

| Solutions (in mg/100 ml) | |
|---|---|
| Compound of formula (Ia) or (Ib), e.g. Compound (d) or (m) or (w) | 333.3 mg |
| Formoterol fumarate | 333.3 mg |
| Benzalkonium chloride | 10.0 mg |
| EDTA | 50.0 mg |
| HCl(ln) | ad pH 3.4 |

This solution may be prepared in the usual manner.

Example 6

| Powder for inhalation | |
|---|---|
| Compound of formula (Ia) or (Ib), e.g. Compound (d) or (m) or (w) | 6 µg |
| Formoterol fumarate | 6 µg |
| Lactose monohydrate | ad 25 mg |

The powder for inhalation is produced in the usual way by mixing the individual ingredients together.

Example 7

| Powder for inhalation | |
|---|---|
| Compound of formula (Ia) or (Ib), e.g. Compound (d) or (m) or (w) | 10 µg |
| Lactose monohydrate | ad 5 mg |

The powder for inhalation is produced in the usual way by mixing the individual ingredients together.

Further Formulations Obtained Analogously to Methods Known in the Art

A: Inhalable Powders

Example 8

| Ingredients | µg per capsule |
|---|---|
| Compound of formula (Ia) or (Ib), e.g. Compound (d) or (m) or (w) | 100 |
| budesonide | 200 |
| lactose | 4700 |
| Total | 5000 |

Example 9

| Ingredients | µg per capsule |
|---|---|
| Compound of formula (Ia) or (Ib), e.g. Compound (d) or (m) or (w) | 100 |
| fluticasone propionate | 125 |
| lactose | 4775 |
| Total | 5000 |

Example 10

| Ingredients | µg per capsule |
|---|---|
| Compound of formula (Ia) or (Ib), e.g. Compound (d) or (m) or (w) | 100 |
| mometasone furoate × $H_2O$ | 250 |
| lactose | 4650 |
| Total | 5000 |

Example 11

| Ingredients | µg per capsule |
|---|---|
| Compound of formula (Ia) or (Ib), e.g. Compound (d) or (m) or (w) | 100 |
| ciclesonide | 250 |
| lactose | 4650 |
| Total | 5000 |

Example 12

| Ingredients | µg per capsule |
|---|---|
| Compound of formula (Ia) or (Ib), e.g. Compound (d) or (m) or (w) | 50 |
| budesonide | 125 |
| lactose | 4825 |
| Total | 5000 |

Example 13

| Ingredients | µg per capsule |
|---|---|
| Compound of formula (Ia) or (Ib), e.g. Compound (d) or (m) or (w) | 50 |
| fluticasone propionate | 200 |
| lactose | 4750 |
| Total | 5000 |

Example 14

| Ingredients | µg per capsule |
|---|---|
| Compound of formula (Ia) or (Ib), e.g. Compound (d) or (m) or (w) | 75 |
| mometasone furoate × $H_2O$ | 250 |
| lactose | 4675 |
| Total | 5000 |

Example 15

| Ingredients | µg per capsule |
|---|---|
| Compound of formula (Ia) or (Ib), e.g. Compound (d) or (m) or (w) | 75 |
| ciclesonide | 250 |
| lactose | 4675 |
| Total | 5000 |

Example 16

| Ingredients | μg per capsule |
|---|---|
| Compound of formula (Ia) or (Ib), e.g. Compound (d) or (m) or (w) | 100 |
| ST-126 | 250 |
| lactose | 4650 |
| Total | 5000 |

Example 17

| Ingredients | μg per capsule |
|---|---|
| Compound of formula (Ia) or (Ib), e.g. Compound (d) or (m) or (w) | 50 |
| ST-126 | 125 |
| lactose | 4825 |
| Total | 5000 |

Example 18

| Ingredients | μg per capsule |
|---|---|
| Compound of formula (Ia) or (Ib), e.g. Compound (d) or (m) or (w) | 100 |
| loteprednol etabonate | 200 |
| lactose | 4700 |
| Total | 5000 |

Example 19

| Ingredients | μg per capsule |
|---|---|
| Compound of formula (Ia) or (Ib), e.g. Compound (d) or (m) or (w) | 100 |
| etiprednol dichloroacetate | 200 |
| lactose | 4700 |
| Total | 5000 |

Example 20

| Ingredients | μg per capsule |
|---|---|
| Compound of formula (Ia) or (Ib), e.g. Compound (d) or (m) or (w) | 100 |
| loteprednol etabonate | 125 |
| lactose | 4775 |
| Total | 5000 |

Example 21

| Ingredients | μg per capsule |
|---|---|
| Compound of formula (Ia) or (Ib), e.g. Compound (d) or (m) or (w) | 50 |
| etiprednol dichloroacetate | 125 |
| lactose | 4825 |
| Total | 5000 |

Example 22

| Ingredients | μg per capsule |
|---|---|
| Compound of formula (Ia) or (Ib), e.g. Compound (d) or (m) or (w) | 100 |
| loteprednol etabonate | 200 |
| $\Delta^1$ - cortienic acid methyl ester | 200 |
| lactose | 4500 |
| Total | 5000 |

Example 23

| Ingredients | μg per capsule |
|---|---|
| Compound of formula (Ia) or (Ib), e.g. Compound (d) or (m) or (w) | 100 |
| loteprednol etabonate | 200 |
| $\Delta^1$ - cortienic acid | 200 |
| lactose | 4500 |
| Total | 5000 |

Example 24

| Ingredients | μg per capsule |
|---|---|
| Compound of formula (Ia) or (Ib), e.g. Compound (d) or (m) or (w) | 100 |
| loteprednol etabonate | 125 |
| $\Delta^1$ - cortienic acid or $\Delta^1$ - cortienic acid methyl ester | 125 |
| lactose | 4650 |
| Total | 5000 |

Example 25

| Ingredients | μg per capsule |
|---|---|
| Compound of formula (Ia) or (Ib), e.g. Compound (d) or (m) or (w) | 50 |
| loteprednol etabonate | 125 |

-continued

| Ingredients | μg per capsule |
| --- | --- |
| Δ¹ - cortienic acid or Δ¹ - cortienic acid methyl ester | 125 |
| lactose | 4700 |
| Total | 5000 |

B. Propellant-Containing Aerosols for Inhalation
(wherein TG 134a is 1,1,1,2-tetrafluoroethane and
TG 227 is 1,1,1,2,3,3,3-heptafluoropropane)

Example 26

Suspension Aerosol

| Ingredients | % by weight |
| --- | --- |
| Compound of formula (Ia) or (Ib), e.g. Compound (d) or (m) or (w) | 0.050 |
| budesonide | 0.4 |
| soya lecithin | 0.2 |
| TG 134a:TG227 (2:3) | to 100 |

Example 27

Suspension Aerosol

| Ingredients | % by weight |
| --- | --- |
| Compound of formula (Ia) or (Ib), e.g. Compound (d) or (m) or (w) | 0.020 |
| fluticasone propionate | 0.3 |
| isopropyl myristate | 0.1 |
| TG 227 | to 100 |

Example 28

Suspension Aerosol

| Ingredients | % by weight |
| --- | --- |
| Compound of formula (Ia) or (Ib), e.g. Compound (d) or (m) or (w) | 0.020 |
| mometasone furoate × H₂O | 0.6 |
| isopropyl myristate | 0.1 |
| TG 227 | to 100 |

Example 29

Suspension Aerosol

| Ingredients | % by weight |
| --- | --- |
| Compound of formula (Ia) or (Ib), e.g. Compound (d) or (m) or (w) | 0.020 |
| ciclesonide | 0.4 |
| isopropyl myristate | 0.1 |
| TG 134a:TG227 (2:3) | to 100 |

Example 30

Suspension Aerosol

| Ingredients | % by weight |
| --- | --- |
| Compound of formula (Ia) or (Ib), e.g. Compound (d) or (m) or (w) | 0.039 |
| ciclesonide | 0.4 |
| absolute ethanol | 0.5 |
| isopropyl myristate | 0.1 |
| TG 134a:TG227 (2:3) | to 100 |

Example 31

Solution Aerosol

| Ingredients | % by weight |
| --- | --- |
| Compound of formula (Ia) or (Ib), e.g. Compound (d) or (m) or (w) | 0.039 |
| fluticasone propionate | 0.2 |
| absolute ethanol | 0.5 |
| isopropyl myristate | 0.1 |
| TG 134a:TG227 (2:3) | to 100 |

Example 32

Solution Aerosol

| Ingredients | % by weight |
| --- | --- |
| Compound of formula (Ia) or (Ib), e.g. Compound (d) or (m) or (w) | 0.039 |
| mometasone furoate × H₂O | 0.6 |
| absolute ethanol | 0.5 |
| isopropyl myristate | 0.1 |
| TG 134a:TG227 (2:3) | to 100 |

Example 33

Solution Aerosol

| Ingredients | % by weight |
| --- | --- |
| Compound of formula (Ia) or (Ib), e.g. Compound (d) or (m) or (w) | 0.039 |
| ciclesonide | 0.4 |
| absolute ethanol | 0.5 |
| isopropyl myristate | 0.1 |
| TG 134a:TG227 (2:3) | to 100 |

Example 34

Solution Aerosol

| Ingredients | % by weight |
| --- | --- |
| Compound of formula (Ia) or (Ib), e.g. Compound (d) or (m) or (w) | 0.039 |
| ST-126 | 0.6 |
| absolute ethanol | 0.5 |
| isopropyl myristate | 0.1 |
| TG 134a:TG227 (2:3) | to 100 |

Example 35

Solution Aerosol

| Ingredients | % by weight |
| --- | --- |
| Compound of formula (Ia) or (Ib), e.g. Compound (d) or (m) or (w) | 0.039 |
| ST-126 | 0.4 |
| absolute ethanol | 0.5 |
| isopropyl myristate | 0.1 |
| TG 134a:TG227 (2:3) | to 100 |

Example 36

| Ingredients | % by weight |
| --- | --- |
| Compound of formula (Ia) or (Ib), e.g. Compound (d) or (m) or (w) | 0.05 |
| loteprednol etabonate | 0.4 |
| soya lecithin | 0.2 |
| TG 134a:TG227 (2:3) | to 100 |

Example 37

| Ingredients | % by weight |
| --- | --- |
| Compound of formula (Ia) or (Ib), e.g. Compound (d) or (m) or (w) | 0.020 |
| loteprednol etabonate | 0.3 |
| isopropyl myristate | 0.1 |
| TG 227 | to 100 |

Example 38

| Ingredients | % by weight |
| --- | --- |
| Compound of formula (Ia) or (Ib), e.g. Compound (d) or (m) or (w) | 0.020 |
| etiprednol dichloracetate | 0.4 |
| isopropyl myristate | 0.1 |
| TG 227 | to 100 |

Example 39

| Ingredients | % by weight |
| --- | --- |
| Compound of formula (Ia) or (Ib), e.g. Compound (d) or (m) or (w) | 0.020 |
| loteprednol etabonate | 0.4 |
| isopropyl myristate | 0.1 |
| TG 134a:TG227 (2:3) | to 100 |

Example 40

| Ingredients | % by weight |
| --- | --- |
| Compound of formula (Ia) or (Ib), e.g. Compound (d) or (m) or (w) | 0.039 |
| loteprednol etabonate | 0.4 |
| absolute ethanol | 0.5 |
| isopropyl myristate | 0.1 |
| TG 134a:TG227 (2:3) | to 100 |

Example 41

| Ingredients | % by weight |
| --- | --- |
| Compound of formula (Ia) or (Ib), e.g. Compound (d) or (m) or (w) | 0.05 |
| loteprednol etabonate | 0.4 |
| $\Delta^1$-cortienic acid or $\Delta^1$-cortienic acid methyl ester | 0.4 |
| soya lecithin | 0.2 |
| TG134a:TG227 (2:3) | to 100 |

Example 42

| Ingredients | % by weight |
|---|---|
| Compound of formula (Ia) or (Ib), e.g. Compound (d) or (m) or (w) | 0.02 |
| loteprednol etabonate | 0.3 |
| $\Delta^1$- cortienic acid or $\Delta^1$- cortienic acid methyl ester | 0.3 |
| isopropyl myristate | 0.1 |
| TG227 | to 100 |

Example 43

| Ingredients | % by weight |
|---|---|
| Compound of formula (Ia) or (Ib), e.g. Compound (d) or (m) or (w) | 0.04 |
| loteprednol etabonate | 0.4 |
| $\Delta^1$- cortienic acid or $\Delta^1$- cortienic acid methyl ester | 0.4 |
| isopropyl myristate | 0.1 |
| TG 227 | to 100 |

Example 44

| Ingredients | % by weight |
|---|---|
| Compound of formula (Ia) or (Ib), e.g. Compound (d) or (m) or (w) | 0.02 |
| loteprednol etabonate | 0.4 |
| $\Delta^1$- cortienic acid or $\Delta^1$- cortienic acid methyl ester | 0.4 |
| isopropyl myristate | 0.1 |
| TG134a:TG227 (2:3) | to 100 |

Example 45

| Ingredients | % by weight |
|---|---|
| Compound of formula (Ia) or (Ib), e.g. Compound (d) or (m) or (w) | 0.039 |
| loteprednol etabonate | 0.4 |
| $\Delta^1$- cortienic acid or $\Delta^1$- cortienic acid methyl ester | 0.4 |
| absolute ethanol | 0.5 |
| isopropyl myristate | 0.1 |
| TG134a:TG227 (2:3) | to 100 |

C. Ophthalmic Formulations

Example 46

| EYE DROPS | |
|---|---|
| Compound of formula (Ia) or (Ib), e.g. Compound (d) or (m) or (w) | 0.05% w/v |
| Tween 80 | 2.5% w/v |
| Ethanol | 0.75% w/v |
| Benzalkonium chloride | 0.02% w/v |
| Phenyl ethanol | 0.25% w/v |
| Sodium chloride | 0.60% w/v |
| Water for injection | q.s. 100 volumes |

Example 47

| EYE DROPS | |
|---|---|
| Compound of formula (Ia) or (Ib), e.g. Compound (d) or (m) or (w) | 0.04% w/v |
| Tween 80 | 2.5% w/v |
| Ethanol | 0.75% w/v |
| Benzalkonium chloride | 0.02% w/v |
| Phenyl ethanol | 0.25% w/v |
| Sodium chloride | 0.60% w/v |
| Water for injection | q.s. 100 volumes |

Example 48

| EYE DROPS | |
|---|---|
| Compound of formula (Ia) or (Ib), e.g. Compound (d) or (m) or (w) | 0.035% w/v |
| Povidone | 0.6% w/v |
| Benzalkonium chloride | 0.02% w/v |
| Sodium edetate U.S.P. | 0.10% w/v |
| Glycerin U.S.P. | 2.5% w/v |
| Tyloxapol U.S.P. | 3.0% w/v |
| Sodium chloride | 0.3% w/v |
| Sodium γ-aminobutyrate | 1.0% w/v |
| Sterile distilled water | q.s. 100 volumes |

The ingredients listed above are combined, then the is checked and, if necessary, adjusted to 5.0-5.5 by basifying with sodium hydroxide or acidifying with hydrochloric acid.

Yet other compositions of the invention can be conveniently formulated using known techniques.

While this description has been couched in terms of various preferred or exemplary embodiments, the skilled artisan will appreciate that various modifications, substitutions, omissions and changes may be made without departing from the spirit thereof Accordingly, it is intended that the scope of the foregoing be limited only by the broadest statements herein and by the scope of the following claims, including equivalents thereof.

What is claimed is:

1. A method for eliciting an anticholinergic response in a subject in need of same, comprising administering to said subject an anticholinergically effective amount of a compound having the formula:

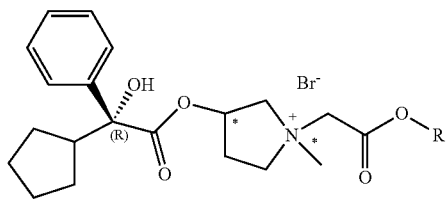

wherein R is methyl or ethyl; and wherein each asterisk marks a chiral center; said compound having the R, S or RS stereoisomeric configuration at each chiral center unless specified otherwise, or being a mixture thereof.

2. A method as claimed in claim 1 for reducing or inhibiting the development of, or alleviating the symptoms of, chronic obstructive pulmonary disease or asthma in a subject in need thereof, comprising administering to said subject an anticholinergically effective amount of a compound having the formula:

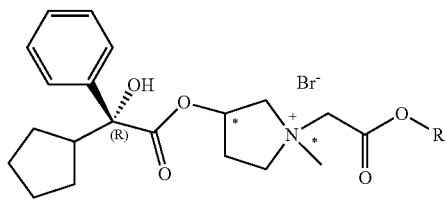

wherein R is methyl or ethyl; and wherein each asterisk marks a chiral center; said compound having the R, S or RS stereoisomeric configuration at each chiral center unless specified otherwise, or being a mixture thereof.

3. A method as claimed in claim 1 for inducing mydriasis in the eye(s) of a subject in need thereof, comprising topically applying to the eye(s) of said subject a mydriatically effective amount of a compound having the formula:

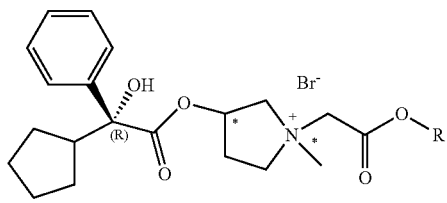

wherein R is methyl or ethyl; and wherein each asterisk marks a chiral center; said compound having the R, S or RS stereoisomeric configuration at each chiral center unless specified otherwise, or being a mixture thereof.

4. A method as claimed in claim 1 for alleviating the symptoms of overactive bladder in a subject in need thereof, comprising administering to said subject an anticholinergically effective amount of a compound having the formula:

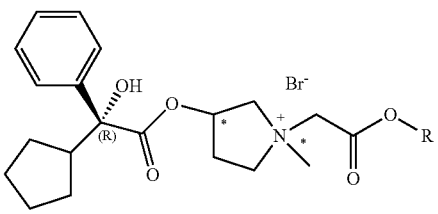

wherein R is methyl or ethyl; and wherein each asterisk marks a chiral center; said compound having the R, S or RS stereoisomeric configuration at each chiral center unless specified otherwise, or being a mixture thereof.

5. A method as claimed in claim 1 for eliciting an antiperspirant effect in a subject in need thereof, comprising topically applying to said subject an antiperspirant effective amount of a compound having the formula:

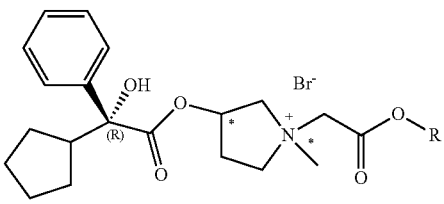

wherein R is methyl or ethyl; and wherein each asterisk marks a chiral center; said compound having the R, S or RS stereoisomeric configuration at each chiral center unless specified otherwise, or being a mixture thereof.

6. The method as claimed in claim 1, wherein the compound is:
3-(2-cyclopentyl-2-phenyl-2-hydroxyacetoxy)-1-(methoxycarbonylmethyl)-1-methylpyrrolidinium bromide;
3-(2-cyclopentyl-2-phenyl-2-hydroxyacetoxy)-1-(ethoxycarbonylmethyl)-1-methylpyrrolidinium bromide;
(2R) 3-(2-cyclopentyl-2-phenyl-2-hydroxyacetoxy)-1-(methoxycarbonylmethyl)-1-methylpyrrolidinium bromide;
(2R) 3-(2-cyclopentyl-2-phenyl-2-hydroxyacetoxy)-1-(ethoxycarbonylmethyl)-1-methylpyrrolidinium bromide;
(2R,3'R) 3-(2-cyclopentyl-2-phenyl-2-hydroxyacetoxy)-1-(methoxycarbonylmethyl)-1-methylpyrrolidinium bromide;
(2R,3'S) 3-(2-cyclopentyl-2-phenyl-2-hydroxyacetoxy)-1-(methoxycarbonylmethyl)-1-methylpyrrolidinium bromide;
(2R,3'S) (2R,3'R) 3-(2-cyclopentyl-2-phenyl-2-hydroxyacetoxy)-1-(ethoxycarbonylmethyl)-1-methylpyrrolidinium bromide;
(2R,3'S) 3-(2-cyclopentyl-2-phenyl-2-hydroxyacetoxy)-1-(ethoxycarbonylmethyl)-1-methylpyrrolidinium bromide;
(2R,1'R,3'S) 3-(2-cyclopentyl-2-phenyl-2-hydroxyacetoxy-1-(ethoxycarbonylmethyl)-1-methylpyrrolidinium bromide;
(2R,1'S,3'S) 3-(2-cyclopentyl-2-phenyl-2-hydroxyacetoxy)-1-(ethoxycarbonylmethyl)-1-methylpyrrolidinium bromide;
(2R,1'R,3'R) 3-(2-cyclopentyl-2-phenyl-2-hydroxyacetoxy)-1-(ethoxycarbonylmethyl)-1-methylpyrrolidinium bromide; or (2R,1'S,3'R) 3-(2-cyclopentyl-2-phenyl-2-hydroxyacetoxy)-1-(ethoxycarbonylmethyl)-1-methylpyrrolidinium bromide.

7. The method as claimed in claim 1, wherein the compound is:
   (a) 3-(2-cyclopentyl-2-phenyl-2-hydroxyacetoxy)-1-(methoxycarbonylmethyl)-1-methylpyrrolidinium bromide;
   (b) 3-(2-cyclopentyl-2-phenyl-2-hydroxyacetoxy)-1-(ethoxycarbonylmethyl)-1-methylpyrrolidinium bromide;
   (c) (2R) 3-(2-cyclopentyl-2-phenyl-2-hydroxyacetoxy)-1-(methoxycarbonylmethyl)-1-methylpyrrolidinium bromide; or
   (d) (2R) 3-(2-cyclopentyl-2-phenyl-2-hydroxyacetoxy)-1-(ethoxycarbonylmethyl)-1-methylpyrrolidinium bromide.

8. A method for eliciting an anticholinergic response selected from the group consisting of a mydriatic response and an antiperspirant response in a subject in need of same, comprising administering to said subject's eye(s) or skin, respectively, an anticholinergically effective amount of a compound having the formula:

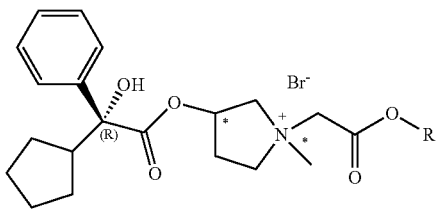

wherein R is methyl or ethyl; and wherein each asterisk marks a chiral center; said compound having the R, S or RS stereoisomeric configuration at each chiral center unless specified otherwise, or being a mixture thereof.

9. The method as claimed in claim 2, wherein the compound is:
   3-(2-cyclopentyl-2-phenyl-2-hydroxyacetoxy)-1-(methoxycarbonylmethyl)-1-methylpyrrolidinium bromide;
   3-(2-cyclopentyl-2-phenyl-2-hydroxyacetoxy)-1-(ethoxycarbonylmethyl)-1-methylpyrrolidinium bromide;
   (2R) 3-(2-cyclopentyl-2-phenyl-2-hydroxyacetoxy)-1-(methoxycarbonylmethyl)-1-methylpyrrolidinium bromide;
   (2R) 3-(2-cyclopentyl-2-phenyl-2-hydroxyacetoxy)-1-(ethoxycarbonylmethyl)-1-methylpyrrolidinium bromide;
   (2R,3'R) 3-(2-cyclopentyl-2-phenyl-2-hydroxyacetoxy)-1-(methoxycarbonylmethyl)-1-methylpyrrolidinium bromide;
   (2R,3'S) 3-(2-cyclopentyl-2-phenyl-2-hydroxyacetoxy)-1-(methoxycarbonylmethyl)-1-methylpyrrolidinium bromide;
   (2R,3'R) 3-(2-cyclopentyl-2-phenyl-2-hydroxyacetoxy)-1-(ethoxycarbonylmethyl)-1-methylpyrrolidinium bromide;
   (2R,3'S) 3-(2-cyclopentyl-2-phenyl-2-hydroxyacetoxy)-1-(ethoxycarbonylmethyl)-1-methylpyrrolidinium bromide;
   (2R,1'R,3'S) 3-(2-cyclopentyl-2-phenyl-2-hydroxyacetoxy)-1-(ethoxycarbonylmethyl)-1-methylpyrrolidinium bromide;
   (2R,1'S,3'S) 3-(2-cyclopentyl-2-phenyl-2-hydroxyacetoxy)-1-(ethoxycarbonylmethyl)-1-methylpyrrolidinium bromide;
   (2R,1'R,3'R) 3-(2-cyclopentyl-2-phenyl-2-hydroxyacetoxy)-1-(ethoxycarbonylmethyl)-1-methylpyrrolidinium bromide; or
   (2R,1'S,3'R) 3-(2-cyclopentyl-2-phenyl-2-hydroxyacetoxy)-1-(ethoxycarbonylmethyl)-1-methylpyrrolidinium bromide.

10. The method as claimed in claim 2, wherein the compound is:
   (a) 3-(2-cyclopentyl-2-phenyl-2-hydroxyacetoxy)-1-(methoxycarbonylmethyl)-1-methylpyrrolidinium bromide;
   (b) 3-(2-cyclopentyl-2-phenyl-2-hydroxyacetoxy)-1-(ethoxycarbonylmethyl)-1-methylpyrrolidinium bromide;
   (c) (2R) 3-(2-cyclopentyl-2-phenyl-2-hydroxyacetoxy)-1-(methoxycarbonylmethyl)-1-methylpyrrolidinium bromide; or
   (d) (2R) 3-(2-cyclopentyl-2-phenyl-2-hydroxyacetoxy)-1-(ethoxycarbonylmethyl)-1-methylpyrrolidinium bromide.

11. The method as claimed in claim 3, wherein the compound is:
   3-(2-cyclopentyl-2-phenyl-2-hydroxyacetoxy)-1-(methoxycarbonylmethyl)-1-methylpyrrolidinium bromide;
   3-(2-cyclopentyl-2-phenyl-2-hydroxyacetoxy)-1-(ethoxycarbonylmethyl)-1-methylpyrrolidinium bromide;
   (2R) 3-(2-cyclopentyl-2-phenyl-2-hydroxyacetoxy)-1-(methoxycarbonylmethyl)-1-methylpyrrolidinium bromide;
   (2R) 3-(2-cyclopentyl-2-phenyl-2-hydroxyacetoxy)-1-(ethoxycarbonylmethyl)-1-methylpyrrolidinium bromide;
   (2R,3'R) 3-(2-cyclopentyl-2-phenyl-2-hydroxyacetoxy)-1-(methoxycarbonylmethyl)-1-methylpyrrolidinium bromide;
   (2R,3'S) 3-(2-cyclopentyl-2-phenyl-2-hydroxyacetoxy)-1-(methoxycarbonylmethyl)-1-methylpyrrolidinium bromide;
   (2R,3'R) 3-(2-cyclopentyl-2-phenyl-2-hydroxyacetoxy)-1-(ethoxycarbonylmethyl)-1-methylpyrrolidinium bromide;
   (2R,3'S) 3-(2-cyclopentyl-2-phenyl-2-hydroxyacetoxy)-1-(ethoxycarbonylmethyl)-1-methylpyrrolidinium bromide;
   (2R,1'R, 3'S) 3-(2-cyclopentyl-2-phenyl-2-hydroxyacetoxy)-1-(ethoxycarbonylmethyl)-1-methylpyrrolidinium bromide;
   (2R,1S,3'S) 3-(2-cyclopentyl-2-phenyl-2-hydroxyacetoxy)-1-(ethoxycarbonylmethyl)-1-methylpyrrolidinium bromide;
   (2R,1'R,3'R) 3-(2-cyclopentyl-2-phenyl-2-hydroxyacetoxy)-1-(ethoxycarbonylmethyl)-1-methylpyrrolidinium bromide; or
   (2R,1'S,3'R) 3-(2-cyclopentyl-2-phenyl-2-hydroxyacetoxy)-1-(ethoxycarbonylmethyl)-1-methylpyrrolidinium bromide.

12. The method as claimed in claim 4, wherein the compound is:
   (a) 3-(2-cyclopentyl-2-phenyl-2-hydroxyacetoxy)-1-(methoxycarbonylmethyl)-1-methylpyrrolidinium bromide;

(b) 3-(2-cyclopentyl-2-phenyl-2-hydroxyacetoxy)-1-(ethoxycarbonylmethyl)-1-methylpyrrolidinium bromide;
(c) (2R) 3-(2-cyclopentyl-2-phenyl-2-hydroxyacetoxy)-1-(methoxycarbonylmethyl)-1-methylpyrrolidinium bromide; or
(d) (2R) 3-(2-cyclopentyl-2-phenyl-2-hydroxyacetoxy)-1-(ethoxycarbonylmethyl)-1-methylpyrrolidinium bromide.

13. The method as claimed in claim 4, wherein the compound is:
3-(2-cyclopentyl-2-phenyl-2-hydroxyacetoxy)-1-(methoxycarbonylmethyl)-1-methylpyrrolidinium bromide;
3-(2-cyclopentyl-2-phenyl-2-hydroxyacetoxy)-1-(ethoxycarbonylmethyl)-1-methylpyrrolidinium bromide;
(2R) 3-(2-cyclopentyl-2-phenyl-2-hydroxyacetoxy)-1-(methoxycarbonylmethyl)-1-methylpyrrolidinium bromide;
(2R) 3-(2-cyclopentyl-2-phenyl-2-hydroxyacetoxy)-1-(ethoxycarbonylmethyl)-1-methylpyrrolidinium bromide;
(2R,3'R) 3-(2-cyclopentyl-2-phenyl-2-hydroxyacetoxy)-1-(methoxycarbonylmethyl)-1-methylpyrrolidinium bromide;
(2R,3'S) 3-(2-cyclopentyl-2-phenyl-2-hydroxyacetoxy)-1-(methoxycarbonylmethyl)-1-methylpyrrolidinium bromide;
(2R,3'R) 3-(2-cyclopentyl-2-phenyl-2-hydroxyacetoxy)-1-(ethoxycarbonylmethyl)-1-methylpyrrolidinium bromide;
(2R,3'S) 3-(2-cyclopentyl-2-phenyl-2-hydroxyacetoxy)-1-(ethoxycarbonylmethyl)-1-methylpyrrolidinium bromide;
(2R,1'R,3'S) 3-(2-cyclopentyl-2-phenyl-2-hydroxyacetoxy)-1-(ethoxycarbonylmethyl)-1-methylpyrrolidinium bromide;
(2R,1'S,3'S) 3-(2-cyclopentyl-2-phenyl-2-hydroxyacetoxy)-1-(ethoxycarbonylmethyl)-1-methylpyrrolidinium bromide;
(2R,1'R,3'R) 3-(2-cyclopentyl-2-phenyl-2-hydroxyacetoxy)-1-(ethoxycarbonylmethyl)-1-methylpyrrolidinium bromide; or
(2R,1'S,3'R) 3-(2-cyclopentyl-2-phenyl-2-hydroxyacetoxy)-1-(ethoxycarbonylmethyl)-1-methylpyrrolidinium bromide.

14. The method as claimed in claim 4, wherein the compound is:
(a) 3-(2-cyclopentyl-2-phenyl-2-hydroxyacetoxy)-1-(methoxycarbonylmethyl)-1-methylpyrrolidinium bromide;
(b) 3-(2-cyclopentyl-2-phenyl-2-hydroxyacetoxy)-1-(ethoxycarbonylmethyl)-1-methylpyrrolidinium bromide;
(c) (2R) 3-(2-cyclopentyl-2-phenyl-2-hydroxyacetoxy)-1-(methoxycarbonylmethyl)-1-methylpyrrolidinium bromide; or
(d) (2R) 3-(2-cyclopentyl-2-phenyl-2-hydroxyacetoxy)-1-(ethoxycarbonylmethyl)-1-methylpyrrolidinium bromide.

15. The method as claimed in claim 5, wherein the compound is:
3-(2-cyclopentyl-2-phenyl-2-hydroxyacetoxy)-1-(methoxycarbonylmethyl)-1-methylpyrrolidinium bromide;
3-(2-cyclopentyl-2-phenyl-2-hydroxyacetoxy)-1-(ethoxycarbonylmethyl)-1-methylpyrrolidinium bromide;
(2R) 3-(2-cyclopentyl-2-phenyl-2-hydroxyacetoxy)-1-(methoxycarbonylmethyl)-1-methylpyrrolidinium bromide;
(2R) 3-(2-cyclopentyl-2-phenyl-2-hydroxyacetoxy)-1-(ethoxycarbonylmethyl)-1-methylpyrrolidinium bromide;
(2R,3'R) 3-(2-cyclopentyl-2-phenyl-2-hydroxyacetoxy)-1-(methoxycarbonylmethyl)-1-methylpyrrolidinium bromide;
(2R,3'S) 3-(2-cyclopentyl-2-phenyl-2-hydroxyacetoxy)-1-(methoxycarbonylmethyl)-1-methylpyrrolidinium bromide;
(2R,3'R) 3-(2-cyclopentyl-2-phenyl-2-hydroxyacetoxy)-1-(ethoxycarbonylmethyl)-1-methylpyrrolidinium bromide;
(2R,3'S) 3-(2-cyclopentyl-2-phenyl-2-hydroxyacetoxy)-1-(ethoxycarbonylmethyl)-1-methylpyrrolidinium bromide;
(2R,1'R,3'S) 3-(2-cyclopentyl-2-phenyl-2-hydroxyacetoxy)-1-(ethoxycarbonylmethyl)-1-methylpyrrolidinium bromide;
(2R,1'S,3'S) 3-(2-cyclopentyl-2-phenyl-2-hydroxyacetoxy)-1-(ethoxycarbonylmethyl)-1-methylpyrrolidinium bromide;
(2R,1'R,3'R) 3-(2-cyclopentyl-2-phenyl-2-hydroxyacetoxy)-1-(ethoxycarbonylmethyl)-1-methylpyrrolidinium bromide; or
(2R,1S,3'R) 3-(2-cyclopentyl-2-phenyl-2-hydroxyacetoxy)-1-(ethoxycarbonylmethyl)-1-methylpyrrolidinium bromide.

16. The method as claimed in claim 5, wherein the compound is:
(a) 3-(2-cyclopentyl-2-phenyl-2-hydroxyacetoxy)-1-(methoxycarbonylmethyl)-1-methylpyrrolidinium bromide;
(b) 3-(2-cyclopentyl-2-phenyl-2-hydroxyacetoxy)-1-(ethoxycarbonylmethyl)-1-methylpyrrolidinium bromide;
(c) (2R) 3-(2-cyclopentyl-2-phenyl-2-hydroxyacetoxy)-1-(methoxycarbonylmethyl)-1-methylpyrrolidinium bromide; or
(d) (2R) 3-(2-cyclopentyl-2-phenyl-2-hydroxyacetoxy)-1-(ethoxycarbonylmethyl)-1-methylpyrrolidinium bromide.

17. The method as claimed in claim 8, wherein the compound is:
3-(2-cyclopentyl-2-phenyl-2-hydroxyacetoxy)-1-(methoxycarbonylmethyl)-1-methylpyrrolidinium bromide;
3-(2-cyclopentyl-2-phenyl-2-hydroxyacetoxy)-1-(ethoxycarbonylmethyl)-1-methylpyrrolidinium bromide;
(2R) 3-(2-cyclopentyl-2-phenyl-2-hydroxyacetoxy)-1-(methoxycarbonylmethyl)-1-methylpyrrolidinium bromide;
(2R) 3-(2-cyclopentyl-2-phenyl-2-hydroxyacetoxy)-1-(ethoxycarbonylmethyl)-1-methylpyrrolidinium bromide;
(2R,3'R) 3-(2-cyclopentyl-2-phenyl-2-hydroxyacetoxy)-1-(methoxycarbonylmethyl)-1-methylpyrrolidinium bromide;
(2R,3'S) 3-(2-cyclopentyl-2-phenyl-2-hydroxyacetoxy)-1-(methoxycarbonylmethyl)-1-methylpyrrolidinium bromide;
(2R,3'R) 3-(2-cyclopentyl-2-phenyl-2-hydroxyacetoxy)-1-(ethoxycarbonylmethyl)-1-methylpyrrolidinium bromide;

(2R,3'S) 3-(2-cyclopentyl-2-phenyl-2-hydroxyacetoxy)-1-(ethoxycarbonylmethyl)-1-methylpyrrolidinium bromide;

(2R,1'R,3'S) 3-(2-cyclopentyl-2-phenyl-2-hydroxyacetoxy)-1-(ethoxycarbonylmethyl)-1-methylpyrrolidinium bromide;

(2R,1'S,3'S) 3-(2-cyclopentyl-2-phenyl-2-hydroxyacetoxy)-1-(ethoxycarbonylmethyl)-1-methylpyrrolidinium bromide;

(2R,1'R,3'R) 3-(2-cyclopentyl-2-phenyl-2-hydroxyacetoxy)-1-(ethoxycarbonylmethyl)-1-methylpyrrolidinium bromide; or (2R,1'S,3'R) 3-(2-cyclopentyl-2-phenyl-2-hydroxyacetoxy)-1-(ethoxycarbonylmethyl)-1-methylpyrrolidinium bromide.

18. The method as claimed in claim 8, wherein the compound is:
  (a) 3-(2-cyclopentyl-2-phenyl-2-hydroxyacetoxy)-1-(methoxycarbonylmethyl)-1-methylpyrrolidinium bromide;
  (b) 3-(2-cyclopentyl-2-phenyl-2-hydroxyacetoxy)-1-(ethoxycarbonylmethyl)-1-methylpyrrolidinium bromide;
  (c) (2R) 3-(2-cyclopentyl-2-phenyl-2-hydroxyacetoxy)-1-(methoxycarbonylmethyl)-1-methylpyrrolidinium bromide; or
  (d) (2R) 3-(2-cyclopentyl-2-phenyl-2-hydroxyacetoxy)-1-(ethoxycarbonylmethyl)-1-methylpyrrolidinium bromide.

\* \* \* \* \*